United States Patent
Vasdev et al.

(10) Patent No.: US 10,259,800 B2
(45) Date of Patent: Apr. 16, 2019

(54) METHOD OF FLUORINATION USING IODONIUM YLIDES

(71) Applicant: The General Hospital Corporation, Boston, MA (US)

(72) Inventors: Neil Vasdev, Cambridge, MA (US); Benjamin H. Rotstein, Somerville, MA (US); Huan Steven Liang, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 25 days.

(21) Appl. No.: 15/166,063

(22) Filed: May 26, 2016

(65) Prior Publication Data

US 2017/0121300 A1 May 4, 2017

Related U.S. Application Data

(60) Provisional application No. 62/248,060, filed on Oct. 29, 2015.

(51) Int. Cl.
| | | |
|---|---|---|
| C07D 319/08 | (2006.01) | |
| C07D 319/06 | (2006.01) | |
| C07D 413/12 | (2006.01) | |
| C07D 405/12 | (2006.01) | |

(52) U.S. Cl.
CPC ......... *C07D 319/08* (2013.01); *C07D 319/06* (2013.01); *C07D 405/12* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 5,106,407 | A | 4/1992 | Relenyi et al. |
| 9,434,699 | B2 | 9/2016 | Vasdev et al. |
| 2008/0015365 | A1 | 1/2008 | Sato et al. |
| 2012/0123120 | A1 | 5/2012 | Satyamurthy et al. |
| 2015/0252007 | A1 | 9/2015 | Vasdev et al. |
| 2016/0362375 | A1 | 12/2016 | Vasdev et al. |

FOREIGN PATENT DOCUMENTS

| | | |
|---|---|---|
| EP | 0145653 | 6/1985 |
| EP | 0160322 | 11/1985 |
| JP | H10101653 | 4/1998 |
| WO | WO2010/117435 | 10/2010 |
| WO | WO 2013/184484 | 12/2013 |

OTHER PUBLICATIONS

Basuli, Falguni. A First Synthesis of 18F-radiolabeled lapatinib: a potential tracer for positron emission tomographic imaging of ErbB1/ErbB2 tyrosine kinase activity. Journal of Labelled Compounds and Radiopharmaceuticals. (2011), 54, 633-636.*
Yagi, Yusuke. The synthesis of [18F]pitavastatin as a tracer for hOATP using the Suzuki coupling. Organic and Biomolecular Chemistry. 2015, 13, 1113-1121.*
The MICAD Research Team. 6-[18F]Fluoro-L-m-tyrosine. May 22, 2006 [Updated Sep. 6, 2006]. In: Molecular Imaging and Contrast Agent Database (MICAD) [Internet]. Bethesda (MD): National Center for Biotechnology Information (US); pp. 1-8.*
Abreu et al. , "New enantioselective method for hydration of alkenes using cyclodextrins as phase transfer catalyst," Tetrahedron, 2005, 61: 11986-11990.
Allwood et al., "Metal-Free Coupling of Saturated Heterocyclic Sulfonylhydrazones with Boronic Acids," J. Org Chem, 2014, 79:328-338.
Ametamey et al., "Molecular Imaging with PET," Chem. Rev., 2008, 108: 1501-1516.
Bhattacharyya et al., "Reductive Amination with Zinc Borohydride. Efficient, Safe Route to Fluorinated Benzylamine," Synth Comm, 1997, 27:4265-4274.
Brooks et al., "Late-stage [18F]Fluorination: New Solutions to Old Problems," Chem. Sci., Dec. 2014, 5:4545-4553.
Calderwood et al.,"Synthesis of 18F-Arenes from Spirocyclic Iodonium(III) Ylides via Continuous-Flow Microfluidics," J Fluor. Chem., Oct. 2015, 178: 249-253.
Campbell and Ritter, "Modern carbon-fluorine bond forming reactions for aryl fluoride synthesis," Chem. Rev., Jan. 2015, 115:612-633.
Cardinale et al., "Iodonium ylides for one-step, no-carrier-added radiofluorination of electron rich arenes, exemplified with 4-(([18F]fluorophenoxy)-phenylmethyl)piperidine NET and SERT ligands," RSC Adv., 2014, 4: 17293-17299.
Cooper et al., "Oxidation Reactions Using Urea-Hydrogen Peroxide; A Safe Alternative to Anhydrous Hydrogen Peroxide," Synlett, 1990, 533-35.
Crawford et al., "Pharmacokinetic benefits of 3,4-dimethoxy substitution of a phenyl ring and design of isosteres yielding orally available cathepsin K inhibitors," J Med. Chem., Oct. 2012, 55:8827-8837.
Dohl, "Recycling and catalytic Approaches for the Development of a Rare-Metal-Free Synthetic Method Using Hypervalent Iodine Reagent," Chem. Pharm. Bull., 2010, 58(2):135-42.
Gao et al., "Metal-Free Oxidative Fluorination of Phenols with [18F]Fluoride," Angew. Chem. Int. Ed., 2012, 51:6733-6737.
Ichiishi et al, "Copper-Catalyzed [18F]Fluorination of (Mesityl)(aryl)iodonium Salts," Org. Lett. , 2014, 16: 3224-3227.
Iiniuma et al, Simple and Practical Method for Preparation of [(Diacetoxy)iodo]arenes with Iodoarenes and m-Chloroperoxybenzoic Acid, Synlett, 2012, 23:2663-2666.
International Preliminary Report on Patentability in International Application No. PCT/US2015/019278, dated Sep. 22, 2016.
International Search Report and Written Opinion issued in PCT/US2015/19278 dated Jun. 11, 2015 (14 pp.).
Jacobson et al., "18F-Labeled Single-Stranded DNA Aptamer for PET Imaging of Protein Tyrosine Kinase-7 Expression," J. Nucl. Med., Nov. 2015, 56( 11): 1780-5.
Jiang, et al., "A Convenient Synthesis of Novel Meldrum's Acid C60 Fullerene Derivatives," Chin. J Chem., Jan. 2007, 25: 86-89.

(Continued)

*Primary Examiner* — Samantha L Shterengarts

(74) *Attorney, Agent, or Firm* — Fish & Richardson P.C.

(57) ABSTRACT

A process for fluorination of aromatic compounds employing iodonium ylides and applicable to radiofluorination using $^{18}F$ is described. Processes, intermediates, reagents and radiolabelled compounds are described.

20 Claims, 1 Drawing Sheet

(56) References Cited

OTHER PUBLICATIONS

Kuik et al., "In vivo biodistribution of no-carrier-added 6-18F-fluoro-3,4-dihydroxy-L-phenylalanine (18F-DOPA), produced by a new nucleophilic substitution approach, compared with carrier-added 18F-DOPA, prepared by conventional electrophilic substitution," J Nucl Med, Jan. 2015, 56: 106-112.
Lee et al., "A Fluoride-derived Electrophilic Late-Stage Fluorination Reagent for PET Imaging," Science, Nov. 2011, 334:639-642.
Lee et al., "Nickel-mediated oxidative fluorination for PET with aqueous [18F] fluoride," J Am. Chem. Soc., Oct. 2012, 134: 17456-17458.
Li et al., "Aminopyridyl/Pyrazinyl Spiro [indoline-3,4'-piperidine]-2-ones as Highly Selective and Efficacious c-Met/ALK Inhibitors," ACS Med. Chem. Lett., Jul. 2013, 4:806-810.
McKillop et al., "Further Functional Group Oxidations using Sodium Perborate," Tetrahedron, 1989, 45(11):3299-3306.
Miller et al., "Synthesis of 11C, 18F, 15O, and 13N Radiolabels for Positron Emission Tomography," Angew. Chem. Int. Ed, Nov. 2008, 47: 8998-9033.
Moon et al., "Facile aromatic radiofluorination of [18F]flumazenil from dialyliodonium salts with evaluation of their stability and selectivity," Org. Biomol. Chem., 2011, 9: 8346-8355.
Mu et al., "18F-Radiolabeling of Aromatic Compounds Using Triarylsulfonium Salts,"Eur. J Org. Chem., Feb. 2012, 2012:889-892.
Pike and Aigbirhio, "Reactions of Cyclotron-produced [18F]Fluoride with Diaryliodonium Salts—a Novel Single-step Route to No-carrier-added [18]Fluoroarenes," J Chem. Soc. Chem. Commun., 1995, 2215-2216.
Roosen et al., "Outer-Sphere Direction in Iridium C—H Borylation," J. Am. Chem. Soc., 2012, 134: 11 350-11353.
Ross et al., "Nucleophilic 18F-fluorination of heteroaromatic iodonium salts with no-carrier-added [18F]fluoride," J Med. Chem. Soc., Jun. 2007, 129: 8018-8025.
Rostein et al., "Mechanistic studies and radiofluorination of structurally diverse pharmaceuticals with spirocyclic iodonium(III) ylides," Chem. Sci. , 2016, 7: 4407-4417.
Rotstein et al., "Spirocyclic hypervalent iodine(III)-mediated radiofluorination of non-activated and hindered aromatics," Nat. Commun., Jul. 2014, 5: 4365-4371.
Sander et al., "Sulfonium Salts as Leaving Groups for Aromatic Labelling of Drug-like Small Molecules with Fluorine-18," Sci. Rep., Apr. 2015, 5: 9941-9945.
Saxena et al., "Synthesis of some substituted pyrazinopyridoindoles and 3D QSAR studies along with related compounds: piperazines, piperidines, pyrazinoisoquinolines, and diphenhydramine, and its semi-rigid analogs as antihistamines (H1)," Bioorg. Med Chem., Dec. 2006, 14:8249-8258.
Stephenson et al., "Iodonium Ylide—Mediated Radiofluorination of 18F-FPEB and Validation for Human Use," J Nuc. Med., 2015, 56, 489-492.
Tredwell et al., "A General Copper-Mediated Nucleophilic 18F Fluorination of Arenes," Angew. Chem. Int. Ed., 2014, 53:7751-7755.
Wang et al., "Ortho-Stabilized 18F-Azido Click Agents and their Application in PET Imaging with Single-Stranded DNA Aptamers," Angew. Chem. Int. Ed., 2015, 54: 12777-12781.
Ye et al., "Straightforward Syntheses of Hypervalent Iodine (III) reagents Mediated by Selectfluor," Org. Lett., 2004, 7(18): 3962.
Zagulyaeva et al., "A General and Convenient Preparation of [Bis(trifluoroacetoxy)iodo] perfluoroalkanes and [Bis(trifluoroacetoxy)iodo)arenes by Oxidation of Organic Iodides Using Ozone and Trifluoroacetic Acid," J. Org. Chem., 2010, 75(6):2119-2122 (abstract).
Cardinale et al., "Simplified synthesis of aryliodonium ylides by a one-pot procedure," Tetrahedron Letters, Feb. 2013, 54: 2067-2069.
Extended European Search Report in Application No. 15757966.5, dated Jul. 10, 2017, 7 pages.
Yusubov et al., Applications of iodonium salts and iodonium ylides as precursors for nucleophilic fluorination in Positron Emission Tomography, ARKIVOC—Reviews and Accounts, Jan. 2013, 364-395.
Yusubov et al., "Iodonium salts in organic synthesis,"ARKIVOC—Reviews and Accounts, Jan. 2011, 370-409.
Lin et al., "Synthesis-Guided Structure Revision of the Sarcodonin, Sarcovioli, and Hydnellin Natural Product Family," J. Org. Chem, 2011, 76: 1013-1030.
Neiland et al., "Synthesis of 4- and 6-methyl derivatives of 5,7-dioxo( 4H,6H)-1,3-dithiolo[ 4,5-d]pyrimidine based on methylbarbitIrric acid; spectral characteristics and acidity constants," Khimiya Geterotsiklicheskikh Soedinenii, 1993, 1526-1533.
Neilands, "Synthesis and X-Ray Crystal Structure of a Novel Tetrathiafulvalene Dimethyl[2,4-dioxo(1H,3H)pyrimido]tetrathiafulvalene, able to form Intermolecular Hydrogen Bonds of Nucleic Acid Base-pair Type," J. Chem. Soc., Chem. Comm, 1995, 325-326.
Office Action in European Application No. 15757966.5, dated Jun. 11, 2018, 5 pages.
Schank and Lick, "Ozonolytic Fragmentation of Phenyliodonium Betha-Diketonates; A Convenient Synthesis of Unsolvated Vic-Triketones," Synthesis, May 1983, 5: 392-395.

* cited by examiner

METHOD OF FLUORINATION USING IODONIUM YLIDES

CROSS-REFERENCE TO RELATED APPLICATIONS

This application claims the benefit of U.S. Provisional Application Ser. No. 62/248,060, filed Oct. 29, 2015, the disclosure of which is incorporated herein by reference in its entirety.

TECHNICAL FIELD

This disclosure relates to iodonium ylide compounds, and more particularly to iodonium ylide useful for promoting radiofluorination reactions.

BACKGROUND

Radiofluorination of arenes, particularly non-activated or sterically hindered positions, with fluorine-18 remains a major challenge and a key limitation for the development of new radiotracers for in vivo imaging with positron emission tomography (PET) (see e.g., Miller et al., Angew. Chem. Int. Ed. 2008, 47:8998-9033).

Taking into consideration its convenient half-life (109.8 min), $^{18}$F is, with carbon-11, among the most desirable nuclides for small molecule PET radiotracers for imaging and quantification of biological processes, such as receptor expression and occupancy, metabolic activity, and cellular proliferation (see e.g., Ametamey et al., Chem. Rev. 2008, 108, 1501-1516).

Increased availability of cyclotron-produced ($^{18}$O(p,n)$^{18}$F) no-carrier-added [$^{18}$F]fluoride for radiosynthesis has promoted the routine production of validated and target-selective PET radiopharmaceuticals suitable for pathology research, disease diagnosis, and drug development. Formation of $^{18}$F—$C_{sp^3}$ bonds using [$^{18}$F]fluoride is generally much more facile than aryl radiofluorination, and can be achieved by nucleophilic displacement using primary or secondary alkyl electrophiles with [$^{18}$F]fluoride. Nucleophilic aromatic substitution ($S_NAr$) using nitroarene, aryl halide, or aryltrimethylammonium salt precursors is a pragmatic strategy for radiofluorination of activated (i.e., electron-deficient) arenes, but is of limited utility for non-activated or deactivated (i.e., electron-rich and/or sterically hindered) substrates. Similarly electrophilic radiofluorination using carrier-added [$^{18}$F]F$_2$ or the rarely utilized Balz-Schiemann and Wallach reactions using [$^{18}$F]fluoride are incapable of producing structurally complex products in high specific activity.

A host of more selective radiofluorination methods for non-activated arenes has been developed with [$^{18}$F]fluoride (see e.g., Brooks et al., Chem. Sci. 2014, 5:4545-4553; and Campbell et al., Chem. Rev. 2015, 115:612-633) including oxidative strategies (see e.g., Gao et al., Angew. Chem. Int. Ed. 2012, 51:6733-6737) and transition metal-mediated reactions (see e.g., Lee et al., Science. 2011, 334:639-642; Lee et al., J. Am. Chem. Soc. 2012, 134:17456-17458; Tredwell et al., Angew. Chem. Int. Ed. 2014, 53:7751-7755; Ichiishi et al., Org. Let. 2014, 16:3224-3227). While these methods have demonstrated innovative reactivity, aside from hypervalent iodonium-mediated methods, they have not been deployed in validated radiopharmaceutical syntheses for clinical imaging applications and appear to engender technical challenges that are preventing their routine use.

Hypervalent iodonium and sulfonium precursors offer metal-free radiofluorination with varying levels of reactivity and selectivity (see e.g., Pike et al., J. Chem. Soc. Chem. Commun., 1995, 2215-2216; Ross et al., J. Am. Chem. Soc., 2007, 129, 8018-8025; International Patent Application No. WO 2010/117435; Cardinale et al., RSCAdv., 2014, 4, 17293-17299; Rotstein et al., Nat. Commun., 2014, 5, 4365-4371; Mu et al., Eur. J. Org. Chem., 2012, 889-892; and Sander et al., Sci. Rep., 2015, 5, 9941-9945). Of these, diaryl iodonium salt precursors have been the most well-established alternative to $S_NAr$ in the preparation of $^{18}$F-labeled compounds (see e.g., Moon et al., Org. Biomol. Chem., 2011, 9, 8346-8355; and Kuik et al., J. Nucl. Med., 2015, 56, 106-112). To achieve high regioselectivity, arenes such as anisole and thiophene are often used as directing groups based on electronic discrimination, with the incoming [$^{18}$F] fluoride intended for less electron-rich arenes (see e.g., Ross et al., J. Am. Chem. Soc., 2007, 129, 8018-8025). In the presence of a copper catalyst, the regioselectivity of diaryliodonium salts during radiofluorination can be controlled with high selectivity (see e.g., Ichiishi et al., Org. Lett., 2014, 16, 3224-3227).

Recently, spirocyclic iodonium ylides were described as arene radiofluorination precursors for hindered and non-activated substrates (see e.g., Rotstein et al., Nat. Commun., 2015, 5, 4365-4371). Iodonium ylides present several advantages for radiofluorination over diaryliodonium salts, foremost being the lack of a counterion and an auxiliary arene. As a result, iodonium ylides can be readily prepared and purified by flash chromatography and radiofluorination can be expected to proceed with high specific activity from [$^{18}$F]fluoride with complete regioselectivity. Cardinale, et al., RSC Advances, 2014, 4(33), 17293-299 and U.S. Pat. Appl. Publ. Ser. No. 2015/0252007A1 iodonium ylides that can be used for fluorination, including radiofluorination of aromatic compounds.

While the utility of these precursors has been demonstrated for synthesis of radiopharmaceuticals (see e.g., Stephenson et al., J. Nuc. Med., 2015, 56, 489492) and bioconjugation reagents (see e.g. Want et al., Angew. Chem. Int. Ed., 2015, 54, 12777-12781; Jacobson et al., J. Nucl. Med., 2015, 56(11), 1780-5; and Calderwood et al., J. Fluor. Chem., 2015, 178, 249-253) the underlying characteristics of these radiofluorination reactions, including mechanism and auxiliary substitution effects, remained uncertain and represented a major hurdle to further advance these reactions in drug labeling and radiotracer development.

SUMMARY

The present disclosure provides a method for radiofluorination that allows $^{18}$F-aromatic fluorides (including heteroaromatic fluorides) to be prepared in high radiochemical yields. The method uses a spirocyclic hypervalent iodine (III)-mediated radiofluorination strategy, based on iodonium ylides. The method involves stable, easily purified precursors and is readily implemented with standard workup procedures. The method provides excellent regioselectivity and allows the incorporation of $^{18}$F into a wide array of aromatic compounds, including non-activated aromatic compounds (including heteroaromatic compounds). The versatility of the method makes it suitable for routine radiopharmaceutical production.

Accordingly, the present disclosure provides, inter alia, a process for fluorodeiodination of an aromatic iodide compound comprising:

(a) oxidizing an aromatic iodide compound (Ar—I) to form an iodonium compound;
(b) reacting the iodonium compound with a compound of formula (A):

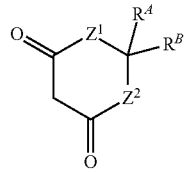

A to form an iodonium ylide;
(c) reacting the iodonium ylide with a fluoride source to form an aromatic fluoride compound (Ar—F), wherein the variables are as defined below.

In some embodiments, the fluoride source is a source of fluorine-18, particularly [$^{18}$F]-fluoride such as In some embodiments, said fluoride source is tetraalkylammonium [$^{18}$F]fluoride. In some embodiments, the [$^{18}$F]fluoride is a tetraalkylammonium [$^{18}$F]fluoride such as tetraethylammonium [$^{18}$F]fluoride. When the fluoride source is a source of fluorine-18, the process provides for nucleophilic radiofluorination of the aromatic iodine compound.

In some embodiments, the compound of Formula A can be one of the following compounds:

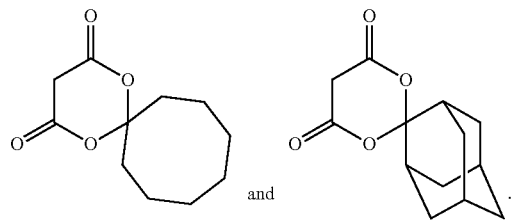 [SMILES: O=C1CC(=O)OC2(CCCCCCC2)O1 ; O=C1CC(=O)OC2(O1)C1CC3CC(C1)CC2C3]

The present disclosure further provides a compound of Formula D:

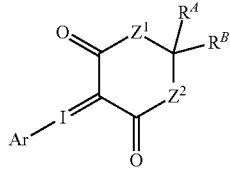

D wherein the variables are as defined below.

In some embodiments, the compound of Formula D can be a compound according to the following formulae:

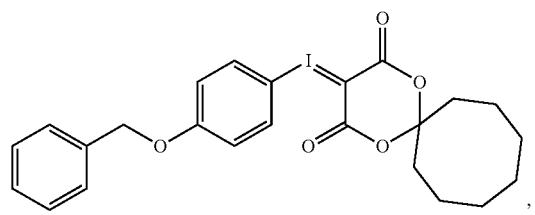

-continued

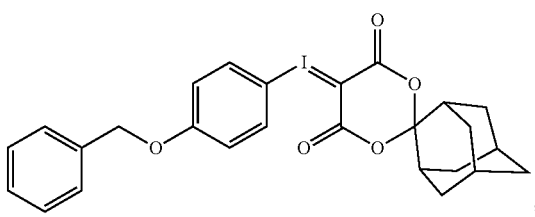

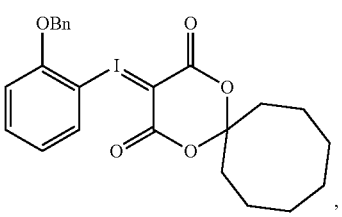

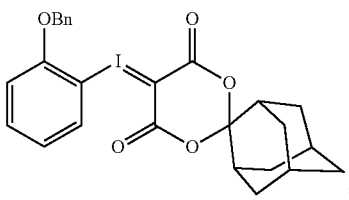

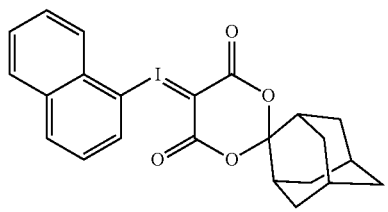

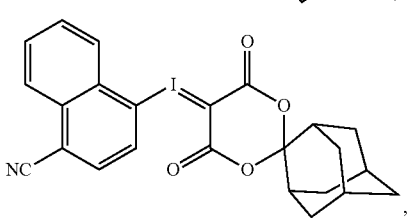

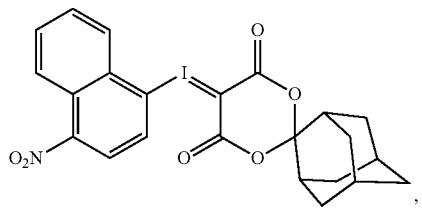

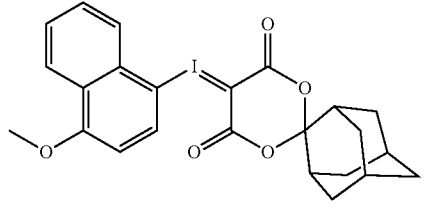

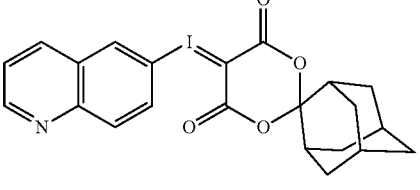

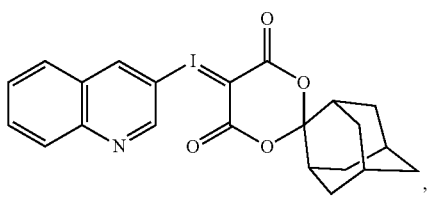,
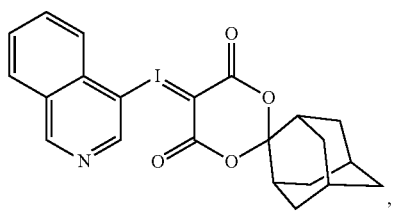,
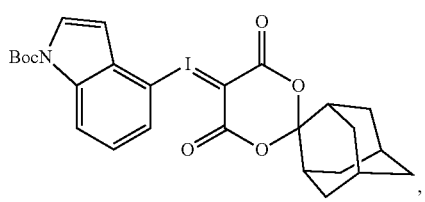,
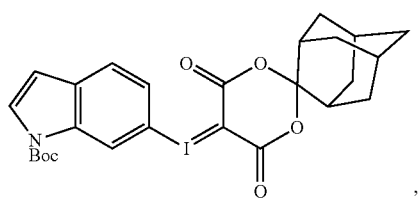,
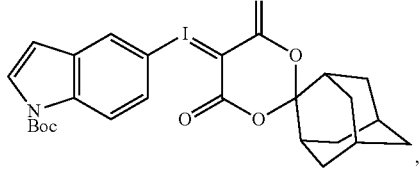,
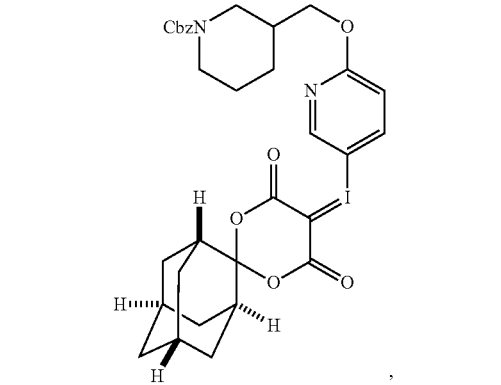,
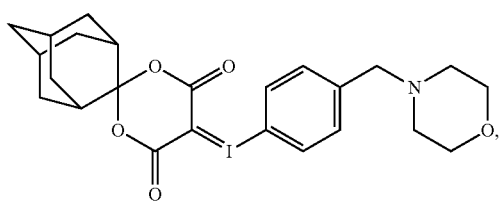,
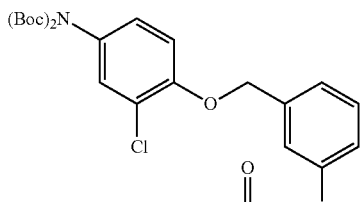,
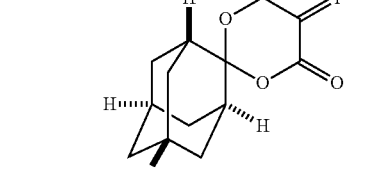,
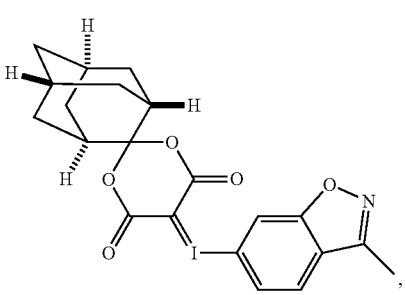,
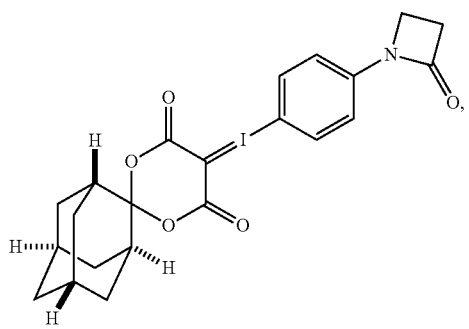,
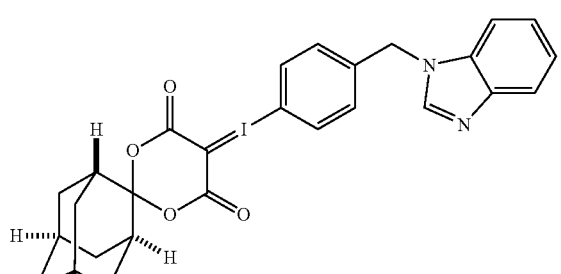,
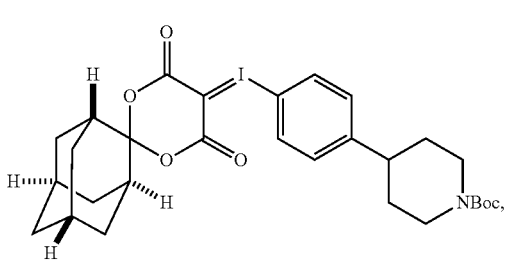,

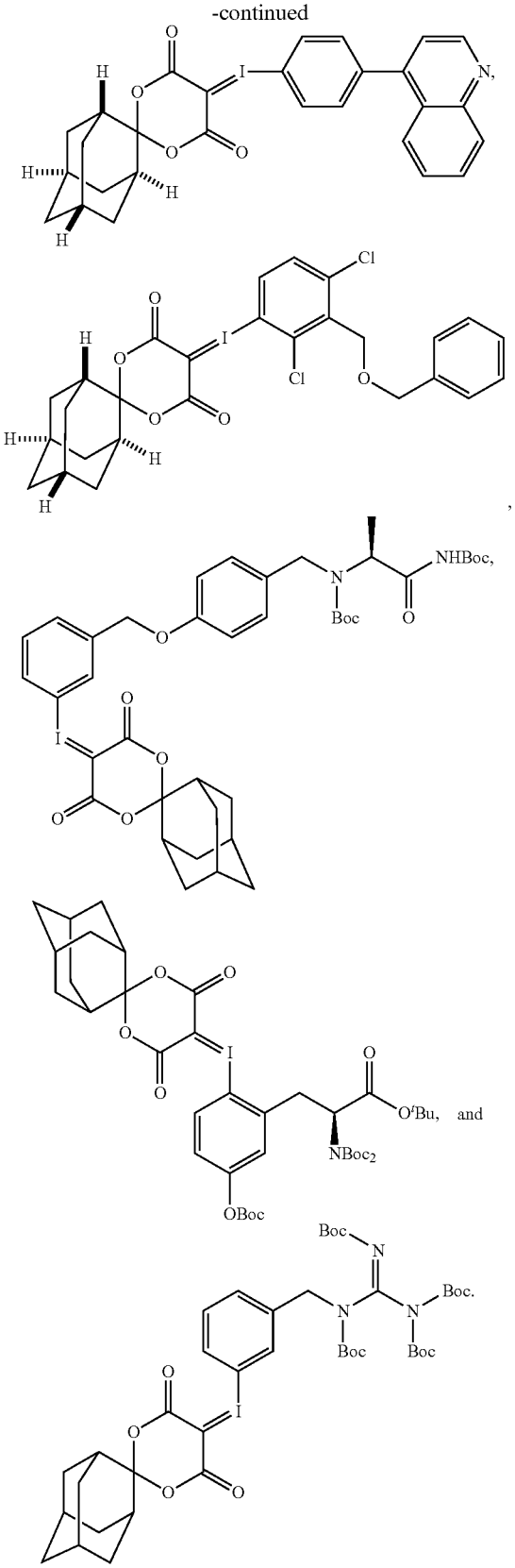

Although methods and materials similar or equivalent to those described herein can be used in the practice or testing of the inventions described herein, suitable methods and materials are described below. All publications, patent applications, patents, and other references mentioned herein are incorporated by reference in their entirety. Where the first page number of a reference is given in a citation, it is to be understood that reference is being made to the entire article cited. In case of conflict, the present specification, including definitions, will control. In addition, the materials, methods, and examples are illustrative only and not intended to be limiting.

Other features and advantages will be apparent from the following detailed description, and from the claims.

DETAILED DESCRIPTION

The present disclosure describes benchmarked theoretical studies of iodonium(III) fluoride intermediates, which help to explain the high reactivity and selectivity of iodonium(III) ylides for radiofluorination, and thermostability studies and reaction monitoring by NMR, which provides insight into the advantages of a new class of adamantyl spirocyclic auxiliaries. Using these precursors, the practical radiosyntheses of drug fragments, as well as [$^{18}$F]safinamide and two clinically relevant radiopharmaceuticals, 6-[$^{18}$F]fluoro-meta-tyrosine and meta-[$^{18}$F]fluorobenzylguanidine is described.

Figure 1:
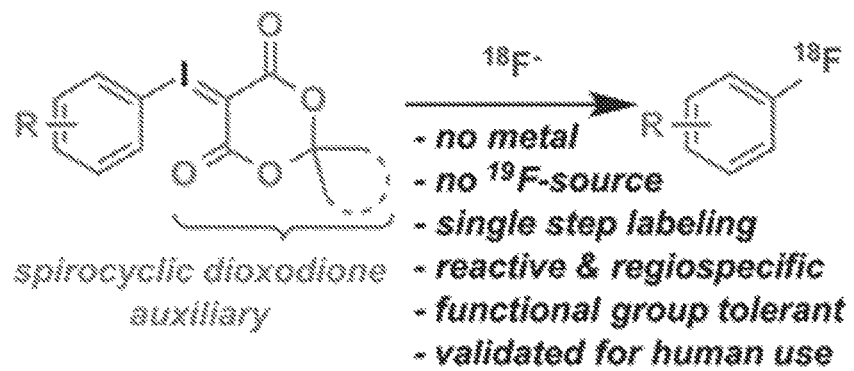
FIG. 1 is a chemical scheme showing a hypervalent iodine(III)-mediated radiofluorination strategy, based on spirocyclic iodonium ylides.

The present disclosure provides a hypervalent iodine(III)-mediated radiofluorination strategy, based on iodonium ylides, preferably spirocyclic iodonium ylides (FIG. 1). The technique affords $^{18}$F-aryl fluorides in high radiochemical yields. The technique involves stable, easily purified precursors and is readily implemented with standard workup procedures. The conceptual advantages of excellent regioselectivity and viability of incorporation of $^{18}$F into a wide array of aromatic compounds including non-activated aromatic compounds makes this methodology suitable for routine radiopharmaceutical production.

Figure 2:
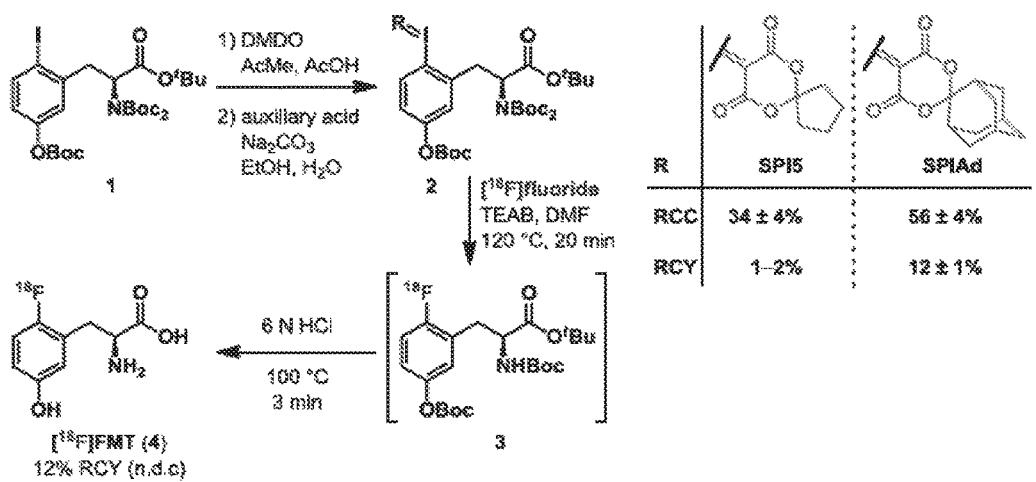
FIG. 2 is a chemical scheme showing a synthesis of 6-[$^{18}$F]fluoro-meta-tyrosine.

For example, the present disclosure provides a newly identified and sterically hindered spiroadamantyl-1,3-dioxane-4,6-dione (i.e., SPIAd) precursor. The extent of radiofluorination for this precursor increased over a 20 minute reaction time to reach 56±4% RCC compared to the corresponding cyclopentyl substituted precursor (FIG. 2). Rapid quantitative deprotection and semi-preparative HPLC purification yielded 12% RCY of 6-[18F]fluoro-meta-tyrosine in approximately 1 hour (n=3).

The methods described herein could also be applied to complex molecules and PET radiopharmaceuticals. For example, fragments of various drug compounds that contain a fluorine atom were selected for isotopic substitution and that would present a challenge for labeling using traditional methods for incorporation of [$^{18}$F]fluoride. Substrates were prepared using selective oxidation strategies and protecting groups as needed to facilitate radiofluorination. The radiofluorinated products and preparation of the SPIAd precursors are provided throughout the Examples disclosed herein. In all cases, the precursors were efficiently prepared for radiofluorination using oxidation methods germane to all synthetic laboratories and without the use of specialized apparatus, such as a glovebox. Typically, oxidation of aryl iodides can be followed by ylide formation in a one-pot process by addition of the SPIAd auxiliary acid and adjustment of the pH of the reaction mixture. Importantly, all precursors could be purified by normal phase flash chromatography and isolated in high purity. SPIAd precursors are typically solid, colorless, and stable to storage at reduced temperatures.

Radiofluorination to prepare the drug fragments was conducted with minor adjustment to the general procedures described herein, using TEAB in DMF as a reaction medium at elevated temperatures for 10-15 minutes. Under these conditions, for example, labeling with [$^{18}$F]fluoride was accomplished for the highly hindered fragment of the dual c-MET and ALK inhibitor, crizotinib. Such encumbered positions are challenging for $S_NAr$ radiofluorination, but particularly activated in the context of iodonium(III) ylides. Radiofluorination of aromatic heterocycles, including isoxazoles, pyridines, and imidazoles is further demonstrated for fragments of risperidone, pitavastatin, astemizole, and filorexant. Similarly, key fluorine-containing drug fragments with saturated heterocycles and basic amines can be labeled, (e.g., piperidines, morpholines, β-lactams, anilines, and the like) and are described herein, including fragments of mosapride, ezetimibe, paroxetine, and lapatinib. These functional groups do not interfere with preparation of SPIAd ylides or their radiofluorination. In addition, carbamate-based protecting groups are well tolerated for primary and secondary amines, and offer versatility for multistep synthesis by orthogonal protection strategies. [$^{18}$F]Safinamide, a reversible monoamine oxidase B (MAO-B) inhibitor was also prepared from a protected precursor by a two-step synthesis involving radiofluorination of the SPIAd precursor, followed by global acid deprotection.

Finally, two clinically relevant radiopharmaceuticals have been prepared and isolated using the methods provided herein: 6-[$^{18}$F]fluoro-meta-tyrosine and meta-[$^{18}$F]fluorobenzylguanidine ([$^{18}$F]mFBG). [$^{18}$F]mFBG is a PET radiotracer for peripheral imaging of the norepinephrine transporter with applications in oncology and cardiac imaging, and is a derivative of the clinically relevant SPECT agent [$^{123}$I]mIBG. The manual multistep radiosynthesis of [$^{18}$F]mFBG involves $S_NAr$ of a metatrimethylammonium-benzonitrile salt, followed by reduction with LiAlH$_4$, and finally guanylation. A SPIAd precursor featuring a protected benzylguanidine was prepared and subjected it to radiofluorination under standard conditions described herein in the presence of 2.5 mg/mL TEAB. Radiochemical conversion to the partially protected $^{18}$F-intermediate was highly reproducible and exceeded 70%, more than double the conversion using the analogous SPI5 precursor. Subsequent acid deprotection and semi-preparative HPLC purification yields [$^{18}$F]mFBG in 14% non-decay-corrected radiochemical yield based on aqueous [$^{18}$F]fluoride and 98% radiochemical purity in a total synthesis time of <75 minutes (n=3).

Definitions

Unless defined otherwise, all technical and scientific terms used herein have the same meaning as is commonly understood by one of ordinary skill in the art to which this disclosure belongs.

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

The term "about" means "approximately" (e.g., plus or minus approximately 10% of the indicated value).

The term "aromatic" refers to a carbocycle or heterocycle having one or more polyunsaturated rings having aromatic character (i.e., having (4n+2) delocalized π (pi) electrons where n is an integer).

The term "aromatic compound" refers to a compound comprising at least one aromatic ring. The aromatic ring can be carbocyclic or heterocyclic. An aromatic compound can comprise one or more aromatic rings, which can include carbocyclic aromatic rings, heterocyclic aromatic rings, or both.

The term "aromatic fluoride compound" refers to an aromatic compound comprising a fluorine atom attached to a carbon atom of an aromatic ring of the aromatic compound. An aromatic fluoride compound can be represented herein by the formula Ar—F, wherein F represents the fluorine radical and Ar represents the remainder of the molecule, wherein the bond between Ar and F is to a carbon atom of an aromatic ring of the group Ar. Ar therefore represents an aromatic compound attached to the remainder of the molecule (an F atom) via an aromatic ring carbon atom.

The term "aromatic iodide compound" refers to an aromatic compound comprising an iodine atom attached to a carbon atom of an aromatic ring of the aromatic compound. An aromatic fluoride compound can be represented herein by the formula Ar—I, wherein I represents the fluorine radical and Ar represents the remainder of the molecule, wherein the bond between Ar and I is to a carbon atom of an aromatic ring of the group Ar.

The term "fluorodeiodination" refers to a chemical process in which an iodine atom is replaced by a fluorine atom, wherein the fluorine atom becomes attached to the atom from which iodine is removed (an "ipso" substitution reaction).

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups are described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent"

attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The term "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chain or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "amino" refers to a group of formula —$NH_2$.

The term "carbamyl" refers to a group of formula —C(=O)$NH_2$.

The term "carbonyl", employed alone or in combination with other terms, refers to a —C(=O)— group, which also may be written as C(O).

The term "carbonyl", employed alone or in combination with other terms, refers to a —C(=O)— group.

The term "carboxy" refers to a group of formula —C(=O)OH.

The term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

The term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

The term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

The term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

The term "aminosulfonyl" refers to a group of formula —S(O)$_2$$NH_2$.

The term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

The term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

The term "aminosulfonylamino" refers to a group of formula —NHS(O)$_2$$NH_2$.

The term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

The term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

The term "aminocarbonylamino", employed alone or in combination with other terms, refers to a group of formula —NHC(O)$NH_2$.

The term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

The term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

The term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

The term "$C_{n-m}$ alkylcarbamoyl" refers to a group of formula —OC(O)NH(alkyl), wherein the alkyl group has n to m carbon atoms. In some embodiments, the alkyl group has 1 to 6, 1 to 4, or 1 to 3 carbon atoms.

The term "thio" refers to a group of formula —SH.

The term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms. The term "$C_{n-m}$ alkylsulfonyl"

refers to a group of formula —S(O)$_2$-alkyl, wherein the alkyl group has n to m carbon atoms. In some embodiments, the alkyl group has 1 to 6, 1 to 4, or 1 to 3 carbon atoms.

The terms "halo" or "halogen", used alone or in combination with other terms, refers to fluoro, chloro, bromo and iodo.

The term "haloalkyl" as used herein refers to an alkyl group in which one or more of the hydrogen atoms has been replaced by a halogen atom. The term "C$_{n-m}$ haloalkyl" refers to a C$_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include CF$_3$, C$_2$F$_5$, CHF$_2$, CCl$_3$, CHCl$_2$, C$_2$Cl$_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "C$_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to oxygen as a divalent substituent, forming a carbonyl group, or attached to a heteroatom forming a sulfoxide or sulfone group, or an N-oxide group.

The term "aryl," employed alone or in combination with other terms, refers to an aromatic hydrocarbon group, which may be monocyclic or polycyclic (e.g., having 2, 3 or 4 fused rings). The term "C$_{n-m}$ aryl" refers to an aryl group having from n to m ring carbon atoms. Aryl groups include, e.g., phenyl, naphthyl, indenyl and the like. In some embodiments, aryl groups have from 6 to 10 carbon atoms. In some embodiments, the aryl group is phenyl.

The term "heteroaryl" or "heteroaromatic", employed alone or in combination with other terms, refers to a monocyclic or polycyclic aromatic heterocycle having at least one heteroatom ring member selected from sulfur, oxygen and nitrogen. In some embodiments, the heteroaryl is 5- to 10-membered C$_{1-9}$ heteroaryl, which is monocyclic or bicyclic and which has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1, 2, 3, or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring.

Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, imidazo[1,2-b]pyridazine, purine, furopyridine (e.g., furo[3,2-b]pyridine), thienopyridine (e.g. thieno[3,2-b]pyridine) or the like.

A five-membered heteroaryl ring is a heteroaryl group having five ring atoms wherein one or more (e.g., 1, 2, 3 or 4) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "cycloalkyl", employed alone or in combination with other terms, refers to a non-aromatic, saturated, monocyclic, bicyclic or polycyclic hydrocarbon ring system, including cyclized alkyl and alkenyl groups. The term "C$_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons (C$_{3-7}$). In some embodiments, the cycloalkyl group has 3 to 6 ring members, 3 to 5 ring members, or 3 to 4 ring members.

In some embodiments, the cycloalkyl group is monocyclic. In some embodiments, the cycloalkyl group is monocyclic or bicyclic. In some embodiments, the cycloalkyl group is a C$_{3-6}$ monocyclic cycloalkyl group. Ring-forming carbon atoms of a cycloalkyl group can be optionally substituted by oxo or sulfido.

Cycloalkyl groups also include cycloalkylidenes. Example cycloalkyl groups include cyclopropyl, cyclobutyl, cyclopentyl, cyclohexyl, cyclopentenyl, cyclohexenyl, cyclohexadienyl, norbornyl, norpinyl, bicyclo[2.1.1]hexanyl, bicyclo[1.1.1]pentanyl and the like. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like, for example indanyl or tetrahydronaphthyl. A cycloalkyl group containing a fused aromatic ring can be attached through any ring-forming atom including a ring-forming atom of the fused aromatic ring.

The term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4-10 ring members, 4-7 ring members or 4-6 ring members. Included in heterocycloalkyl are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Examples of heterocycloalkyl groups include azetidine, pyrrolidine, piperidine, piperazine, morpholine, thiomorpholine, pyran, azepane, tetrahydropyran, tetrahydrofuran, dihydropyran, dihydrofuran and the like. Ring-forming carbon atoms and heteroatoms of a heterocycloalkyl group can be optionally substituted by oxo or sulfido (e.g., C(=O), S(=O), C(S) or S(=O)$_2$, etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 1, 2, 3, 4-tetrahydroquinoline, dihydrobenzofuran, azetidine, azepane, diazepan (e.g., 1,4-diazepan), pyrrolidine, piperidine, piperazine, morpholine, thiomorpholine, pyran, tetrahydrofuran and di- and tetra-hydropyran.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereoisomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated as included in the description of the compounds. Cis and trans geometric isomers of the compounds may exist and may be isolated as a mixture of isomers or as separated isomeric forms.

Compounds as described herein can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers and isotopes of the structures depicted.

All compounds provided herein can be found together with other substances such as water and solvents (e.g., hydrates and solvates) or can be isolated. When in the solid state, the compounds described herein may occur in various forms and may, e.g., take the form of solvates, including hydrates. The compounds may be in any solid state form, such as a polymorph or solvate, so unless clearly indicated otherwise, reference in the specification to compounds should be understood as encompassing any solid state form of the compound.

In some embodiments, the compounds described herein are substantially isolated. By "substantially isolated" is meant that the compound is at least partially or substantially separated from the environment in which it was formed or detected. Partial separation can include, e.g., a composition enriched in the compounds described herein. Substantial separation can include compositions containing at least about 50%, at least about 60%, at least about 70%, at least about 80%, at least about 90%, at least about 95%, at least about 97%, or at least about 99% by weight of the compounds described herein.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable sub-combination. Thus, it is contemplated that features described as embodiments of the processes and compounds described herein can be combined in any suitable combination.

The following abbreviations may be used herein: AcOH (acetic acid); Ac$_2$O (acetic anhydride) aq. (aqueous); Ar (argon); BHT (butylated hydroxytoluene); Bq (becquerel); br (broad); calc. (calculated); CHCl$_3$ (chloroform); Ci (curie); conc. (concentrated); d (doublet); dd (doublet of doublets); DCM (dichloromethane); DMF (N,N-dimethylformamide); DMDO (dimethyldioxirane); DMSO (dimethylsulfoxide); Et (ethyl); EtOAc (ethyl acetate); EtOH (ethanol); [$^{18}$F]Et$_4$NF ([$^{18}$F]tetraethylammonium fluoride); g (gram(s)); h (hour(s)); H$_2$SO$_4$ (sulfuric acid); HCl (hydrochloric acid or hydrogen chloride); HPLC (high performance liquid chromatography); HRMS (high resolution mass spectrometry); Hz (hertz); iPr (isopropyl); J (coupling constant); LCMS (liquid chromatography—mass spectrometry); m (multiplet); M (molar); mCPBA (m-chloroperbenzoic acid); Me (methyl); MeCN (acetonitrile); MeOH (methanol); MgSO$_4$ (magnesium sulfate); MS (mass spectrometry); mg (milligram(s)); min. (minutes(s)); mL (milliliter(s)); mmol (millimole(s)); N (normal); N$_2$ (nitrogen gas); NaHCO$_3$ (sodium bicarbonate); NH$_4$HCO$_2$ (ammonium formate); NH$_4$Cl (ammonium chloride); NaI (sodium iodide); NaOH (sodium hydroxide); nBu (n-butyl); nM (nanomolar); NMR (nuclear magnetic resonance spectroscopy); OXONE® (potassium peroxymonosulfate); P$_2$O$_5$ (diphosphorus pentoxide); PET (positron emission tomography); radio-TLC (radio thin layer chromatography); radio-HPLC (radio high performance liquid chromatography); RP-HPLC (reverse phase high performance liquid chromatography); s (singlet); SPIAd (spiroadamantyl-1,3-dioxane-4,6-dione); t (triplet or tertiary); tert (tertiary); tt (triplet of triplets); TBAF (tetra-n-butylammoniumfluoride); t-Bu (tert-butyl); TEA (triethylamine); TEAB (tetraethylammonium bicarbonate); TEMPO ((2,2,6,6-tetramethylpiperidin-1-yl)oxyl); TFA (trifluoroacetic acid); THF (tetrahydrofuran); μA (microamp(s)); μg (microgram(s)); μL (microliter(s)); μm (micromolar); UV (ultra-violet); wt % (weight percent).

Chemical Processes

The present disclosure provides, inter alia, a process for fluorodeiodination of an aromatic iodide compound comprising:

(a) oxidizing an aromatic iodide compound (Ar-1) to form an iodonium compound:

(b) reacting the iodonium compound with a compound of formula (A):

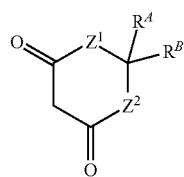

to form an iodonium ylide;

(c) reacting the iodonium ylide with a fluoride source to form an aromatic fluoride compound (Ar—F);

wherein:

$Z^1$ is selected from the group consisting of $NR^{Z1}$, O, and S;

$Z^2$ is selected from the group consisting of $NR^{Z2}$, O, and S;

$R^{Z1}$ is selected from the group consisting of H, $C_{1-6}$ alkyl, $C_{3-10}$ cycloalkyl, $C_{6-10}$ aryl, 4-10 membered heterocycloalkyl, and 5-10 membered heteroaryl, wherein said $C_{6-10}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^{Z2}$ is selected from the group consisting of H, $C_{1-6}$ alkyl, $C_{3-10}$ cycloalkyl, $C_{6-10}$ aryl, 4-10 membered heterocycloalkyl, and 5-10 membered heteroaryl, wherein said $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^A$ and $R^B$ in combination, together with the carbon atom to which $R^A$ and $R^B$ are attached, form an 8, 9, or 10-membered carbocyclic or heterocyclic ring containing 8 to 10 carbon atoms and 0, 1, or 2 ring heteroatoms, each independently selected from N, O, and S, wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo; and and each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino.

In some embodiments, step (a) is performed in the presence of an oxidizing agent. In some embodiments, step (a) is performed in the presence of a carboxylate source. In some embodiments, step (a) is performed in the presence of an oxidizing agent and a carboxylate source.

In some embodiments, step (a) is performed in the presence of an oxidizing agent selected from the group consisting of sodium perborate, urea-hydrogen peroxide adduct, 1-chloromethyl-4-fluoro-1,4-diazoniabicyclo[2.2.2]octane bis(tetrafluoroborate) (Selectfluor®), potassium peroxymonosulfate (OXONE®), dimethyldioxirane, or meta-chloroperoxybenzoic acid. In some embodiments, the oxidizing agent is a urea-hydrogen peroxide adduct.

In some embodiments, step (a) is performed in the presence of a carboxylate source that is an acetate source or trifluoroacetate source. In some embodiments, the carboxylate source is an acetate source. In some embodiments, the carboxylate source is a trifluoroacetate source.

In some embodiments, said carboxylate source is selected from the group consisting of glacial acetic acid, acetic acid in acetone, acetic anhydride, trimethylsilyl acetate, and trifluoroacetic acid.

In some embodiments, said oxidizing agent is urea-hydrogen peroxide adduct and said carboxylate source is glacial acetic acid, acetic anhydride, or a combination thereof.

In some embodiments, said oxidizing agent is urea-hydrogen peroxide adduct and said carboxylate source is glacial acetic acid.

In some embodiments, said oxidizing agent is urea-hydrogen peroxide adduct and said carboxylate source is acetic anhydride.

In some embodiments, said oxidizing agent is urea-hydrogen peroxide adduct and said carboxylate source is a combination of glacial acetic acid and acetic anhydride.

In some embodiments, the process further comprises performing step (a) in the presence of a metal acetate salt. In some embodiments, said metal acetate salt is sodium acetate.

In some embodiments, step (a) is carried out in the presence of a solvent. In some embodiments, the solvent can comprise glacial acetic acid. In some embodiments, the solvent can comprise glacial acetic acid and acetic anhydride. In some embodiments, the solvent can comprise anhydrous acetonitrile.

In some embodiments, the solvent can comprise chloroform. In some embodiments, the solvent can comprise acetone.

In some embodiments, step (a) is carried out at a temperature at from about 0° C. to about 50° C. or from about 40° C. to about 50° C. In some embodiments, step (a) is carried out at about 0° C. In some embodiments, step (a) is carried out at about room temperature (e.g., about 15° C., about 20° C., about 25° C. or about 30° C.). In some embodiments, step (a) is carried out at about 40° C. In some embodiments, step (a) is carried out at about 50° C.

In some embodiments, said iodonium product of step (a) is an iodonium compound of Formula B or Formula C:

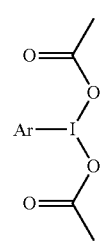

-continued

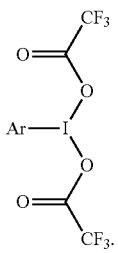

In some embodiments, said iodonium ylide formed in step (b) is an iodonium ylide of Formula D:

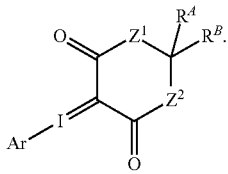

In some embodiments, $Z^1$ is O.

In some embodiments, $Z^2$ is O.

In some embodiments, Z and $Z^2$ are each O.

In some embodiments, $R^A$ and $R^B$ in combination, together with the carbon atom to which $R^A$ and $R^B$ are attached, form an 8, 9, or 10-membered carbocyclic ring, wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo.

In some embodiments, $R^A$ and $R^B$ in combination, together with the carbon atom to which $R^A$ and $R^B$ are attached, form an 8, 9, or 10-membered carbocyclic ring, wherein the ring formed by the combination of $R^A$ and $R^B$ is unsubstituted.

In some embodiments, $R^A$ and $R^B$ in combination, together with the carbon atom to which $R^A$ and $R^B$ are attached, form a cyclooctane or adamantyl ring.

In some embodiments, the compound of Formula A is selected from compounds of the following formulae:

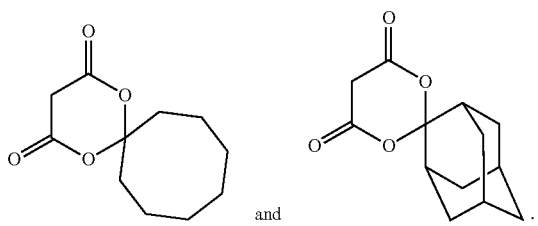 [SMILES: O=C1CC(=O)OC2(CCCCCCC2)O1 ; "and" ; O=C1CC(=O)OC2(O1)C1CC3CC(C1)CC2C3]

In some embodiments, the compound of Formula A is a compound of the following formula:

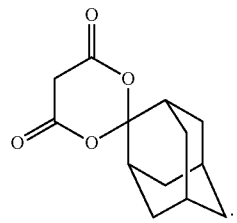 [SMILES: O=C1CC(=O)OC2(O1)C1CC3CC(C1)CC2C3]

In some embodiments, the compound of Formula D is a compound of the following formula:

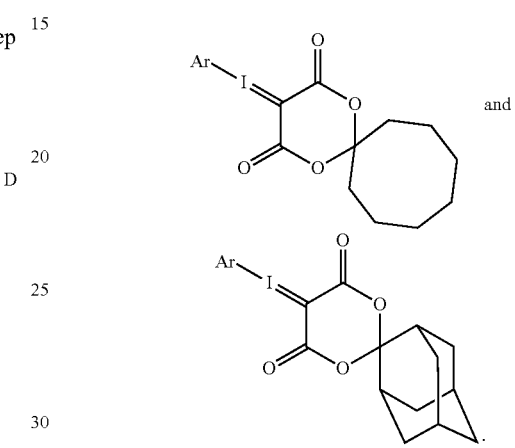

In some embodiments, steps (a) and (b) are performed without isolating or purifying the iodonium compound. In some embodiments, steps (a) and (b) are carried out sequentially in a single vessel (i.e., a "one pot" process).

In some embodiments, the process comprises isolating or purifying the iodonium compound following step (a).

In some embodiments, the process comprises isolating or purifying the iodonium ylide following step (b).

In some embodiments, step (b) is carried out in the presence of a solvent. In some embodiments, the solvent can comprise glacial acetic acid. In some embodiments, the solvent can comprise glacial acetic acid and acetic anhydride. In some embodiments, the solvent can comprise anhydrous acetonitrile.

In some embodiments, the solvent can comprise chloroform. In some embodiments, the solvent can comprise acetone.

In some embodiments, step (b) is carried out in the presence of a base. In some embodiments the base can be a carbonate base. In some embodiments, the base can be an alkali metal carbonate base. In some embodiments, the alkali metal carbonate base is sodium carbonate, e.g., a 10% aqueous solution of sodium carbonate. In some embodiments, the base can be lithium carbonate. In some embodiments, the base can be potassium carbonate. In some embodiments, the base can be cesium carbonate.

In some embodiments, step (b) can be carried out under an inert atmosphere, e.g., nitrogen or argon.

In some embodiments, step (b) is carried out at a temperature at from about 0° C. to about 60° C. or from about 40° C. to about 60° C. In some embodiments, step (b) is carried out at about 0° C. In some embodiments, step (b) is carried out at about room temperature (e.g., about 15° C., about 20° C., about 25° C., or about 30° C.). In some embodiments, step (b) is carried out at about 40° C. In some embodiments, step (b) is carried out at about 50° C. In some embodiments, step (b) is carried out at about 60° C.

In some embodiments, said fluoride source of step (c) is a fluoride salt. Examples of suitable fluoride salts include sodium fluoride, potassium fluoride, cesium fluoride and tetraalkylammonium fluoride salts.

In some embodiments, said fluoride source of step (c) is a tetraalkylammonium fluoride. In some embodiments, said tetraalkylammonium fluoride is tetraethylammonium fluoride.

In some embodiments, said fluoride source comprises $^{18}$F. In some embodiments, said fluoride source comprises an [$^{18}$F]fluoride source, e.g., an [$^{18}$F]fluoride salt. In some embodiments, said fluoride source is tetraalkylammonium [$^{18}$F]fluoride. In some embodiments, said tetraalkylammonium [$^{18}$F]fluoride is tetraethylammonium [$^{18}$F]fluoride.

In some embodiments, the process comprises isolating or purifying the aromatic fluoride following step (c). In some embodiments, step (c) is carried in out in a solvent. In some embodiments, the solvent component of step (c) comprises a polar aprotic solvent such as DMF or 2-pyrrolidone. In some embodiments, step (c) is carried out at a temperature of about 100° C. to about 150° C. e.g., about 120° C.

There is thus provided a process for preparing an iodonium ylide compound according to Formula D, or any of the embodiments thereof, comprising:

(a) oxidizing an aromatic iodide compound (Ar—I), to form an iodonium compound; and (b) reacting the iodonium compound with a compound of formula A:

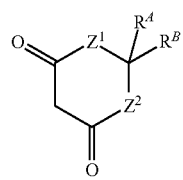

A wherein $Z^1$, $Z^2$, $R^A$ and $R^B$ are as defined for the compound of Formula D, or any of the embodiments thereof, to form the compound according to Formula D.

Also provided is a process for preparing an aromatic fluoride compound (Ar—F) comprising (c) reacting a compound according to Formula D, or any of the embodiments thereof, with a fluoride source to form an aromatic fluoride compound (Ar—F). In some embodiments, the fluoride source of step (c) is a fluoride salt. In some embodiments, the fluoride source comprises [$^{18}$F] fluoride. In some embodiments, the fluoride source is tetraethylammonium [$^{18}$F]fluoride.

Intermediate Compounds

The present disclosure further provides a compound of Formula D:

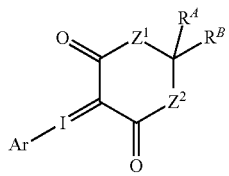

D wherein:

Ar is an aromatic group;

$Z^1$ is selected from the group consisting of $NR^{Z1}$, O, and S;

$Z^2$ is selected from the group consisting of $NR^{Z2}$, O, and S;

$R^{Z1}$ is selected from the group consisting of H, $C_{1-6}$ alkyl, $C_{3-10}$ cycloalkyl, $C_{6-10}$ aryl, 4-10 membered heterocycloalkyl, and 5-10 membered heteroaryl, wherein said $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^{Z2}$ is selected from the group consisting of H, $C_{1-6}$ alkyl, $C_{3-10}$ cycloalkyl, $C_{6-10}$ aryl, 4-10 membered heterocycloalkyl, and 5-10 membered heteroaryl, wherein said $C_{1-6}$ alkyl, $C_{3-10}$ cycloalkyl, $C_{6-10}$ to aryl, 4-10 membered heterocycloalkyl, and 5-10 membered heteroaryl are each optionally substituted by 1, 2, 3, or 4 independently selected $R^{20}$ groups;

$R^A$ and $R^B$ in combination, together with the carbon atom to which $R^A$ and $R^B$ are attached, form an 8, 9, or 10-membered carbocyclic or heterocyclic ring containing 8 to 10 carbon atoms and 0, 1, or 2 ring heteroatoms, each independently selected from N, O, and S, wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

and each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino; and wherein Ar is connected to the iodonium group through an aromatic ring carbon atom.

In some embodiments. $Z^1$ is O.

In some embodiments, $Z^2$ is O.

In some embodiments, $Z^1$ and $Z^2$ are each O.

In some embodiments, $R^A$ and $R^B$ in combination, together with the carbon atom to which $R^A$ and $R^B$ are attached, form an 8, 9, or 10-membered carbocyclic ring, wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo.

In some embodiments, $R^A$ and $R^B$ in combination, together with the carbon atom to which $R^A$ and $R^B$ are attached, form an 8, 9, or 10-membered carbocyclic ring, wherein the ring formed by the combination of $R^A$ and $R^B$ is unsubstituted.

In some embodiments, $R^A$ and $R^B$ in combination, together with the carbon atom to which $R^A$ and $R^B$ are attached, form a cyclooctane or adamantyl ring.

In some embodiments, the compound of Formula D is selected from compounds of the following formulae:

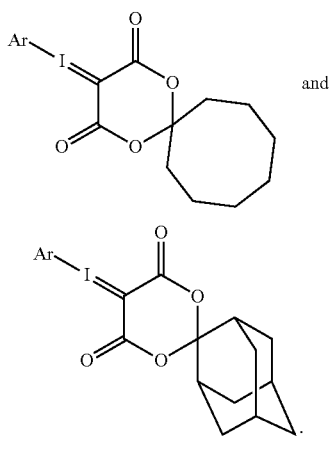 and

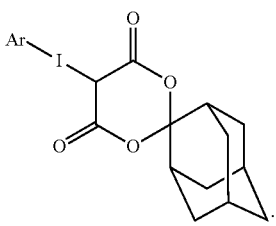

In some embodiments, the compound of Formula D is a compound of the following formula:

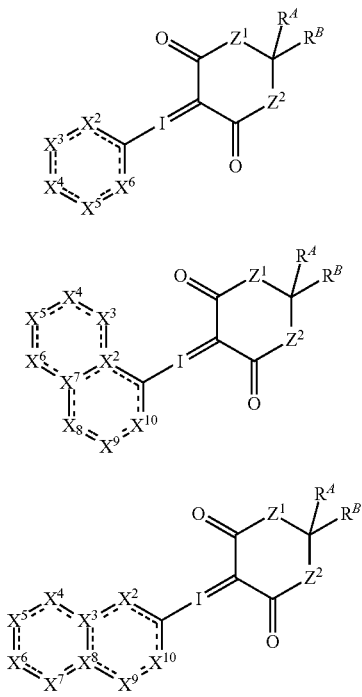

In some embodiments, the compound of Formula D is a compound of Formula D-1, Formula D-2, Formula D-3, Formula D-4, or Formula D-5:

D-1

D-2

D-3

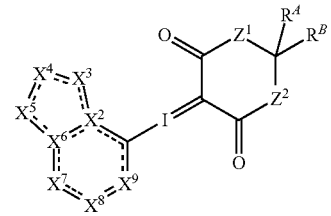

D-4

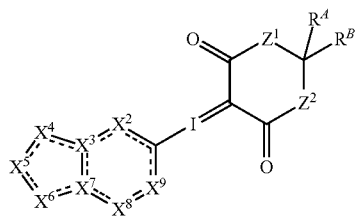

D-5 wherein:

$X^2$ is C, $CR^2$, N, or $NR^2$;
$X^3$ is C, $CR^3$, N, or $NR^3$;
$X^4$ is $CR^4$, N, or $NR^4$;
$X^5$ is $CR^5$, N, or NR;
$X^6$ is C, $CR^6$, N, or $NR^6$;
$X^7$ is C, $CR^7$, N, or $NR^7$;
$X^8$ is C, $CR^8$, N, or $NR^8$;
$X^9$ is $CR^9$, N, or $NR^9$;
$X^{10}$ is $CR^{10}$, N, or $NR^{10}$;

$R^2$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, $NO_2$, $OR^{a2}$, $SR^{a2}$, $C(O)R^{b2}$, $C(O)NR^{c2}R^{d2}$, $C(O)OR^{a2}$, —($C_{1-6}$ alkylene)-$C(O)OR^{a2}$, $OC(O)R^{b2}$, $OC(O)NR^{c2}R^2$, $NR^{c2}R^{d2}$, $NR^{c2}C(O)R^{b2}$, $NR^{c2}C(O)NR^{c2}R^{d2}$, $NR^{c2}C(O)OR^{a2}$, —($C_{1-6}$ alkylene)-$NR^{c2}C(O)OR^{a2}$, $C(=NR^2)NR^{c2}R^{d2}$, $NR^{c2}C(=NR^{e2})NR^{c2}R^{d2}$, $S(O)R^{b2}$, $S(O)NR^{c2}R^{d2}$, $S(O)_2R^{b2}$, $NR^{c2}S(O)_2R^{b2}$ and $S(O)_2NR^{c2}R^{d2}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^3$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, —($C_{1-6}$ alkylene)-$C(O)OR^{a3}OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, —($C_{1-6}$ alkylene)-$NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ and $S(O)_2NR^{c3}R^{d3}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^4$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, $NO_2$, $OR^{a4}$, $SR^{a4}$, $C(O)R^{b4}$, $C(O)NR^{c4}R^{d4}$, $C(O)OR^{a4}$, —($C_{1-6}$ alkylene)-$C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, —($C_{1-6}$ alkylene)-$NR^{c4}C(O)OR^{a4}$, $C(=NR^{e4})NR^{c4}R^{d4}$, $NR^{c4}C(=NR^{e4})$ $NR^{c4}R^{d4}$, $S(O)R^{b4}$, $S(O)NR^{c4}R^{d4}$, $S(O)_2R^{b4}$, $NR^{c4}S(O)_2R^{b4}$ and $S(O)_2NR^{c4}R^{d4}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^5$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, $NO_2$, $OR^{a5}$, $SR^{a5}$, $C(O)R^{b5}$, $C(O)NR^{c5}R^{d5}$, $C(O)OR^{a5}$, —$(C_{1-6}$ alkylene)-$C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, —$(C_{1-6}$ alkylene)-$NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$ and $S(O)_2NR^{c5}R^{d5}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^6$ is selected from the group consisting of H, halogen, $C_{1-6}$ alkyl, $C_{1-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, $NO_2$, $OR^{a7}$, $SR^{a6}$, $C(O)R^{b6}$, $C(O)NR^{c6}R^{d6}$, $C(O)OR^{a6}$, —$(C_{1-6}$alkylene)-$C(O)OR^{a6}$, $OC(O)R^{b6}$, $OC(O)NR^{c6}R^{d6}$, $NR^{c6}R^{d6}$, $NR^{c6}C(O)R^{b6}$, —$(C_{1-6}$ alkylene)-$NR^{c6}C(O)OR^{a6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})N^{c6}R^{d6}$, $S(O)R^{b6}$, $S(O)NR^{c6}R^{d6}$, $S(O)_2R^{b6}$, $NR^{c6}S(O)_2R^{b6}$ and $S(O)_2NR^{c6}R^{d6}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^7$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, $NO_2$, $OR^{a7}$, $SR^{a7}$, $C(O)R^{b7}$, $C(O)NR^{c7}R^{d7}$, $C(O)OR^{a7}$, —$(C_{1-6}$ alkylene)-$C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, —$(C_{1-6}$ alkylene)-$NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$ and $S(O)_2NR^{c7}R^{d7}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^8$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl. $C_{6-10}$ aryl, 4-10 membered heterocycloalkyl, 5-10 membered heteroaryl, CN, $NO_2$, $OR^{a8}$, $SR^{a8}$, $C(O)R^{b8}$, $C(O)NR^{c8}R^{d8}$, $C(O)OR^{a8}$, —$(C_{1-6}$ alkylene)-$C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)NR^{c8}R^{d8}$, $NR^{c8}C(O)OR^{a8}$, —$(C_{1-6}$ alkylene)-$NR^{c8}C(O)OR^{a8}$, $C(=NR^{e8})NR^{c8}R^{d8}$, $NR^{c8}C(=NR^{e8})NR^{c8}R^{d8}$, $S(O)R^{b8}$, $S(O)NR^{c8}R^{d8}$, $S(O)_2R^{b8}$, $NR^{c8}S(O)_2R^{b8}$ and $S(O)_2NR^{c8}R^{d8}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^9$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, $NO_2$, $OR^{a9}$, $SR^{a9}$, $C(O)R^{b9}$, $C(O)NR^{c9}R^{d9}$, $C(O)OR^{a9}$, —$(C_{1-6}$ alkylene)-$C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)NR^{c9}R^{d9}$, $NR^{c9}C(O)OR^{a9}$, —$(C_{1-6}$ alkylene)-$NR^{c9}C(O)OR^{a9}$, $C(=NR^{e9})NR^{c9}R^{d9}$, $NR^{c9}C(=NR^{e9})NR^{c9}R^{d9}$, $S(O)R^{b9}$, $S(O)NR^{c9}R^{d9}$, $S(O)_2R^{b9}$, $NR^{c9}S(O)_2R^{b9}$ and $S(O)_2NR^{c9}R^{d9}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^{10}$ is selected from the group consisting of H, halogen, $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 4-10 membered heterocycloalkyl, 5-10 membered heteroaryl, CN, $NO_2$, $OR^{a10}$, $SR^{a10}$, $C(O)R^{b10}$, $C(O)NR^{c10}R^{d10}$, $C(O)OR^{a10}$, —$(C_{1-6}$ alkylene)-$C(O)OR^{a10}$, $OC(O)R^{b10}$, $OC(O)NR^{c10}R^{d10}$, $NR^{c10}R^{d10}$, $NR^{c10}C(O)R^{b10}$, $NR^{c10}C(O)NR^{c10}R^{d10}$, $NR^{c10}C(O)OR^{a10}$, —$(C_{1-6}$ alkylene)-$NR^{c10}C(O)OR^{a10}$, $C(=NR^{e10})NR^{c10}R^{d10}$, $NR^{c10}C(=NR^{e10})NR^{c10}R^{d10}$, $S(O)R^{b10}$, $S(O)NR^{c10}R^{d10}$, $S(O)_2 R^{b10}$, $NR^{c10}S(O)_2R^{b10}$ and $S(O)_2NR^{c10}R^{d10}$, wherein said $C_{1-6}$ alkyl, $C_{2-6}$ alkenyl, $C_{2-6}$ alkynyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

or $R^2$ and $R^3$ in combination, together with the carbon or nitrogen atoms to which $R^2$ and $R^3$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^1$ and $R^2$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

or $R^3$ and $R^4$ in combination, together with the carbon or nitrogen atoms to which $R^3$ and $R^4$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of R and $R^4$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

or $R^4$ and $R^5$ in combination, together with the carbon or nitrogen atoms to which $R^4$ and $R^5$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^4$ and $R^5$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

or $R^5$ and $R^6$ in combination, together with the carbon or nitrogen atoms to which $R^5$ and $R^6$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^5$ and $R^6$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

or $R^6$ and $R^7$ in combination, together with the carbon or nitrogen atoms to which $R^6$ and $R^7$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^5$ and $R^6$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

or $R^7$ and $R^8$ in combination, together with the carbon or nitrogen atoms to which $R^7$ and $R^8$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^1$ and $R^6$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

or $R^8$ and $R^9$ in combination, together with the carbon or nitrogen atoms to which $R^8$ and $R^9$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^1$ and $R^6$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

or $R^9$ and $R^{10}$ in combination, together with the carbon or nitrogen atoms to which $R^9$ and $R^{10}$ are attached, form a 4-12 membered carbocyclic or heterocyclic ring containing 4 to 12 carbon atoms and 0, 1, or 2 ring heteroatoms, each independently selected from N, O, and S, wherein the ring formed by the combination of $R^5$ and $R^6$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

$R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a6}$, $R^{b6}$, $R^{c6}$, $R^{d6}$, $R^{a7}$, $R^{b7}$, $R^{c7}$, $R^{d7}$, $R^{a8}$, $R^{b8}$, $R^{c8}$, $R^{d8}$, $R^{a9}$, $R^{b9}$, $R^{c9}$, $R^{d9}$, $R^{a10}$, $R^{b10}$, $R^{c10}$, and $R^{d10}$ are each independently selected from the group consisting of H, $C_{1-6}$ alkyl, $C_{2-6}$ alkenyl, $C_{2-6}$ alkynyl, $C_{1-6}$ haloalkyl, and $C_{1-6}$ hydroxyalkyl, $R^{e2}$, $R^{e3}$, $R^{e4}$, $R^{e5}$, $R^{e6}$, $R^{e7}$, $R^{e8}$, $R^{e9}$, and $R^{e10}$ are each independently selected from H, OH, and $C_{1-6}$ alkyl.

In some embodiments, $X^2$ is N. In some embodiments, $X^2$ is C. In some embodiments, $X^2$ is $CR^2$.

In some embodiments, $X^3$ is N. In some embodiments, $X^3$ is C. In some embodiments, $X^3$ is $CR^3$.

In some embodiments, $X^4$ is N. In some embodiments, $X^4$ is $CR^4$.

In some embodiments, $X^5$ is N. In some embodiments, $X^5$ is CR.

In some embodiments, $X^6$ is N. In some embodiments, $X^6$ is C. In some embodiments, $X^6$ is $CR^6$.

In some embodiments, $X^7$ is N. In some embodiments, $X^7$ is C. In some embodiments, $X^7$ is $CR^7$.

In some embodiments, $X^8$ is N. In some embodiments, $X^8$ is C. In some embodiments, $X^8$ is $CR^8$.

In some embodiments, $X^9$ is N. In some embodiments, $X^9$ is $CR^9$.

In some embodiments, $X^{10}$ is N. In some embodiments, $X^{10}$ is $CR^{10}$.

In some embodiments, $R^2$ is H, —$OCH_2$-phenyl,

In some embodiments, $R^3$ is H.

In some embodiments, $R^4$ is H, —$OCH_2$-phenyl, or —C(=O)OtBu.

In some embodiments, $R^5$ is H or —C(=O)OtBu.

In some embodiments, $R^6$ is H or —C(=O)OtBu.

In some embodiments, $R^7$ is H.

In some embodiments, $R^8$ is H, CN, $NO_2$, or $OR^8$. In some embodiments, $R^8$ is H, CN, $NO_2$, or methoxy.

In some embodiments, $R^9$ is H.

In some embodiments, $R^{10}$ is H.

In some embodiments, $Z^1$ is O.

In some embodiments, $Z^2$ is O.

In some embodiments. $Z^1$ and $Z^2$ are each O.

In some embodiments, $R^A$ and $R^B$ in combination, together with the carbon atom to which $R^A$ and $R^B$ are attached, form an 8, 9, or 10-membered carbocyclic ring, wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo.

In some embodiments, $R^A$ and $R^B$ in combination, together with the carbon atom to which $R^A$ and $R^B$ are attached, form an 8, 9, or 10-membered carbocyclic ring, wherein the ring formed by the combination of $R^A$ and $R^B$ is unsubstituted.

In some embodiments, $R^A$ and $R^B$ in combination, together with the carbon atom to which $R^A$ and $R^B$ are attached, form a cyclooctane or adamantyl ring.

In some embodiments, the compound of Formula D is a compound of Formula D-1:

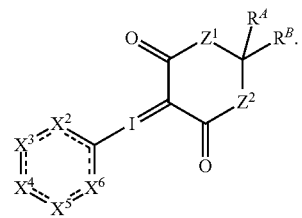

D-1

In some embodiments, the compound of Formula D is a compound of Formula D-2:

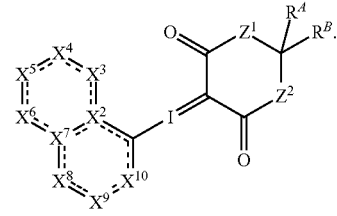

D-2

In some embodiments, the compound of Formula D is a compound of Formula D-3:

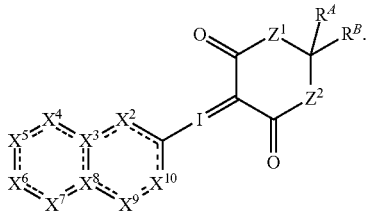

D-3

In some embodiments, the compound of Formula D is a compound of Formula D-4:

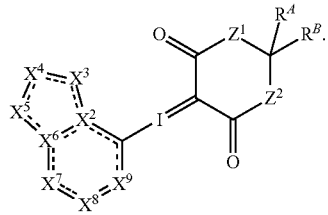
D-4
In some embodiments, the compound of Formula D is a compound of Formula D-5:
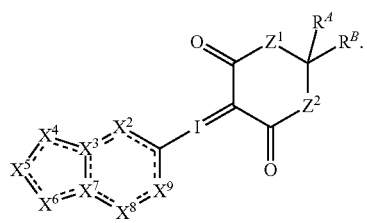
D-5
In some embodiments, the compound of Formula D is selected from compounds of the following formulae:
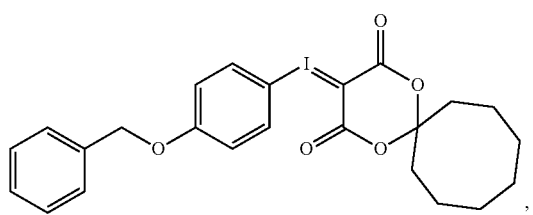
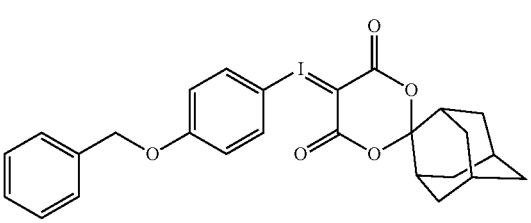
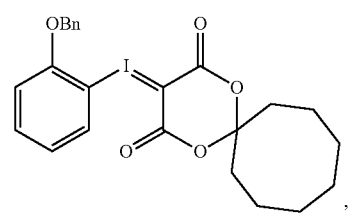
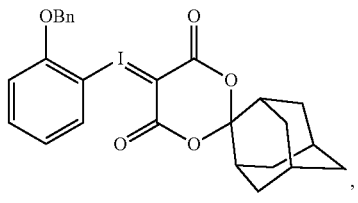
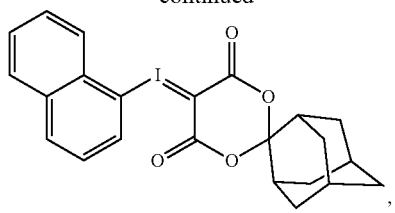
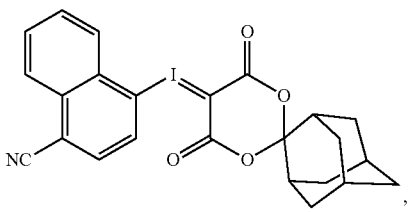
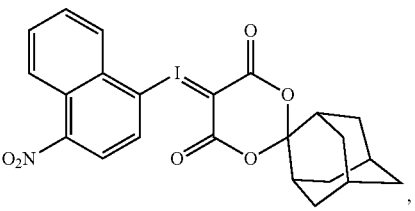
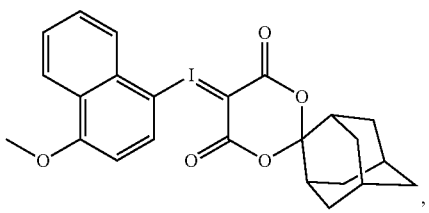
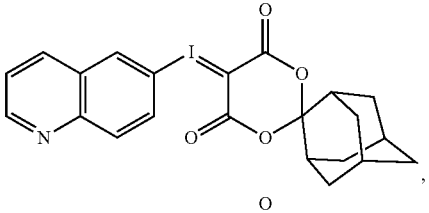
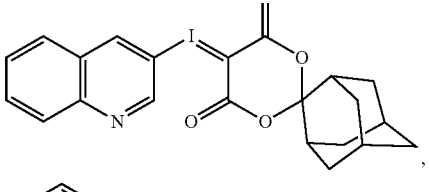
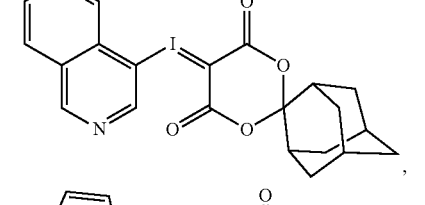
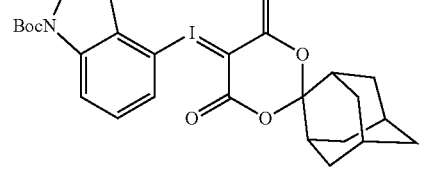

31
-continued
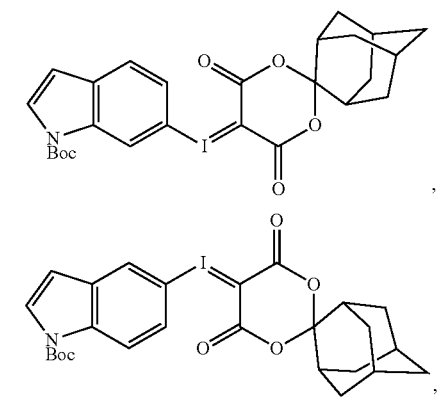
,
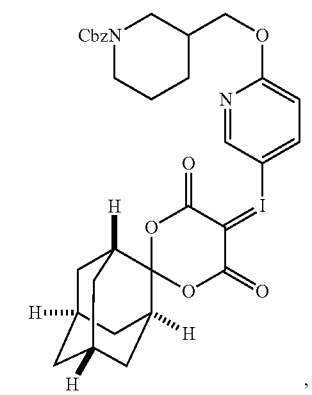
,
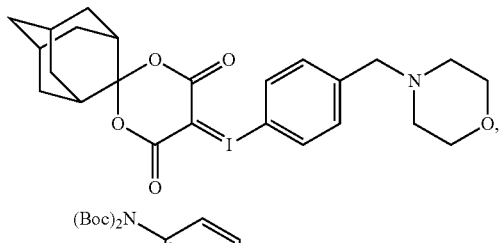
,
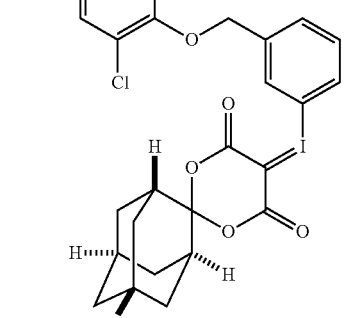
,
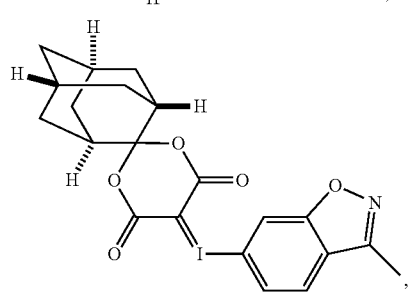
,
32
-continued
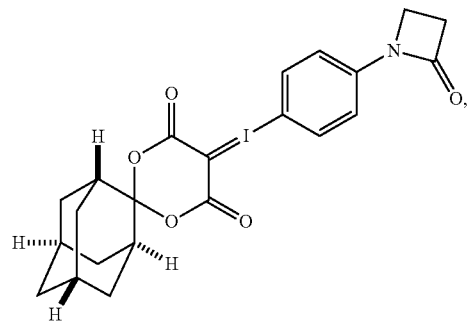
,
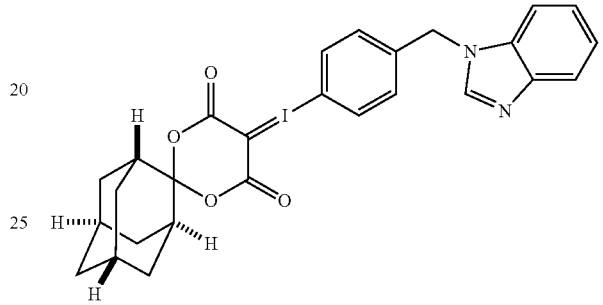
,
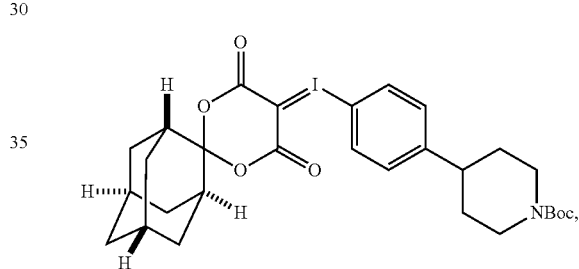
,
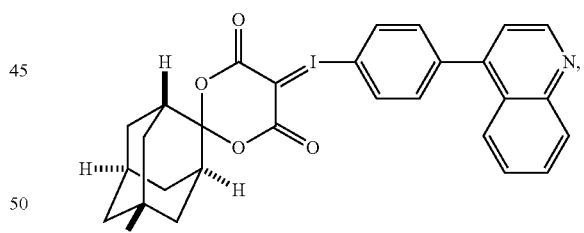
,
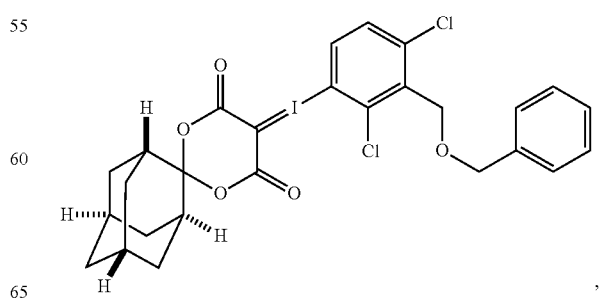
,

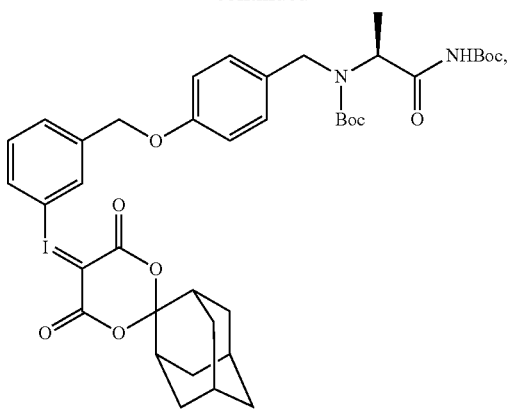
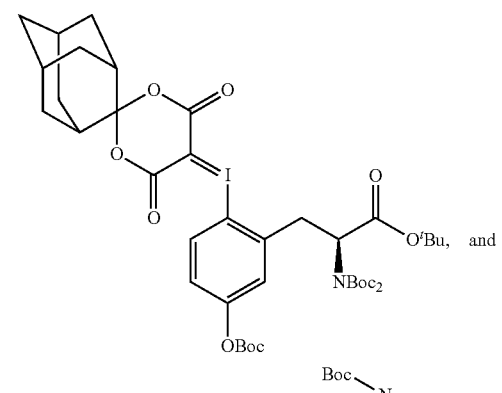
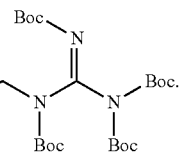
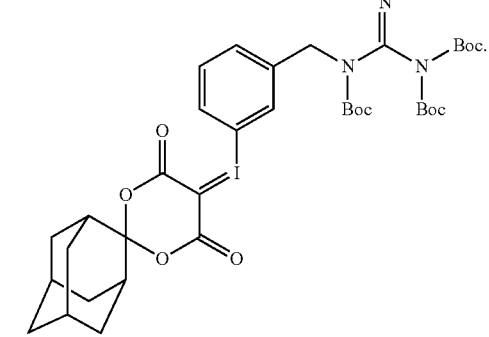
In some embodiments, an intermediate provided herein is selected from compounds of the following formulae:
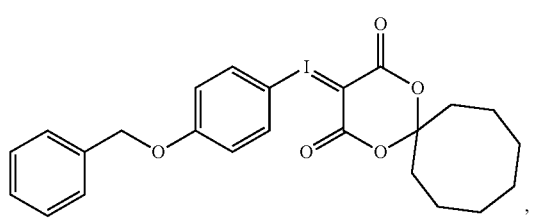
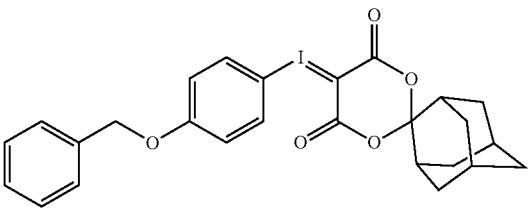
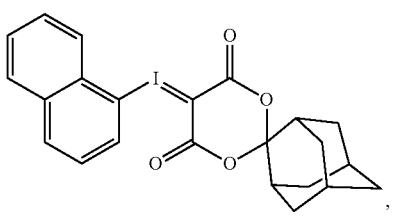
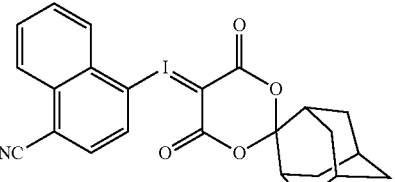
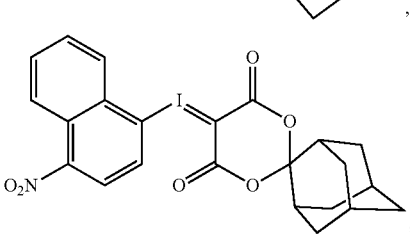
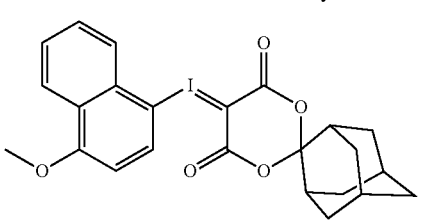
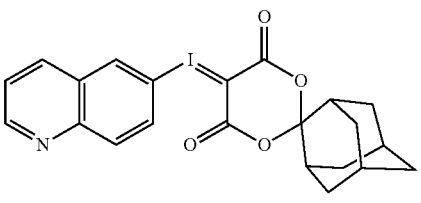
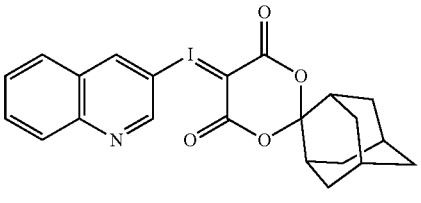

35
-continued
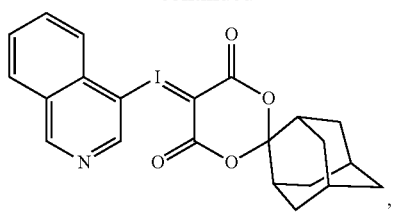
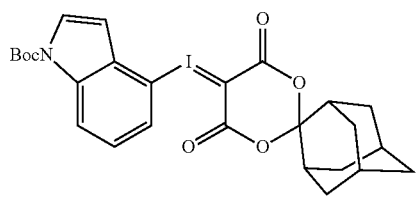
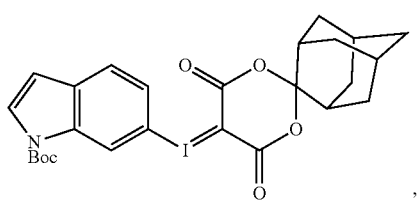
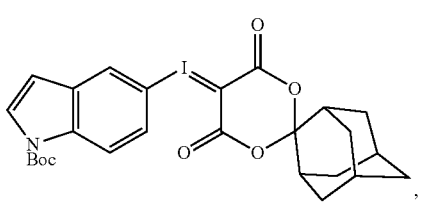
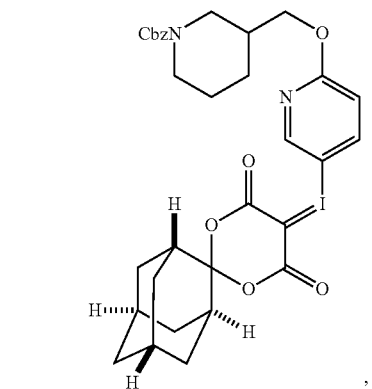
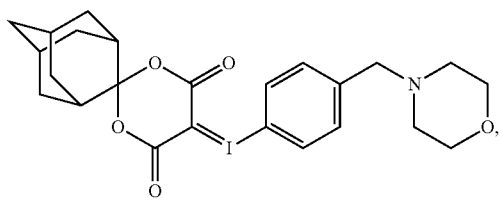
36
-continued
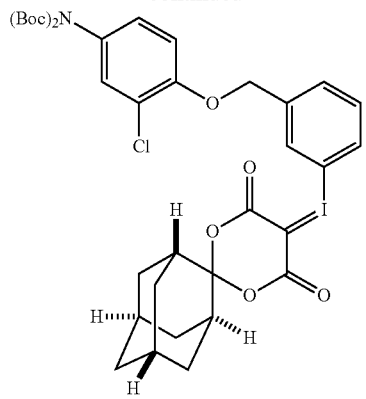
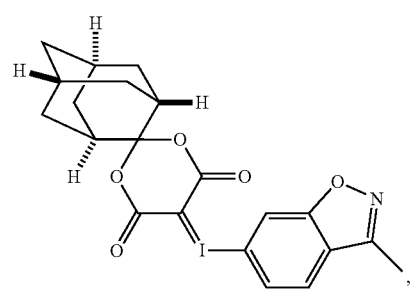
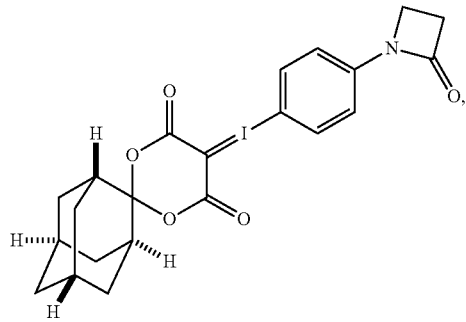
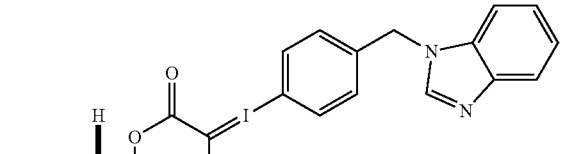
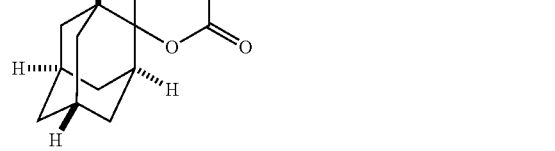
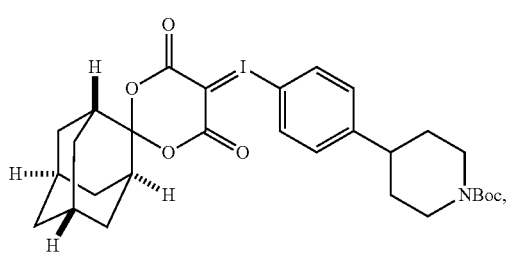

37
-continued
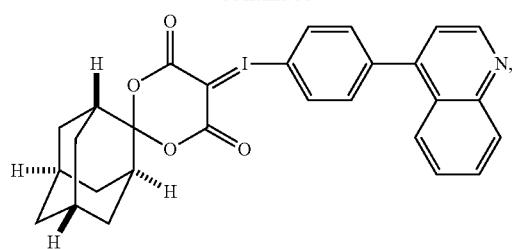
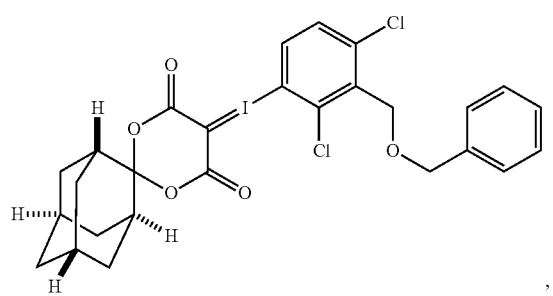
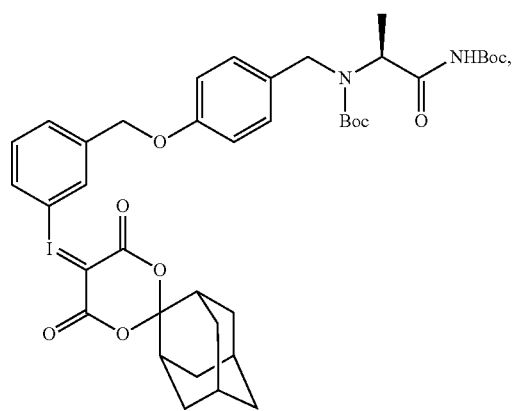
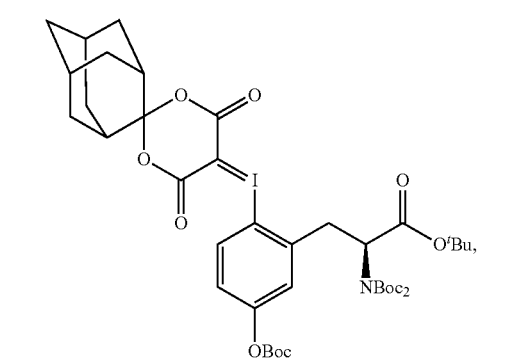
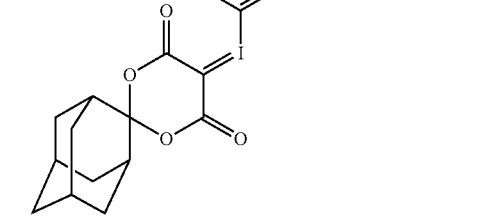
38
-continued
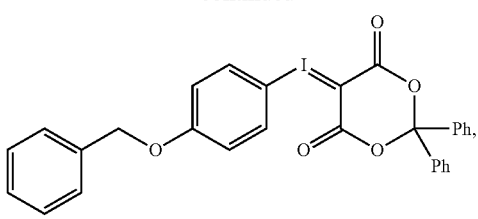
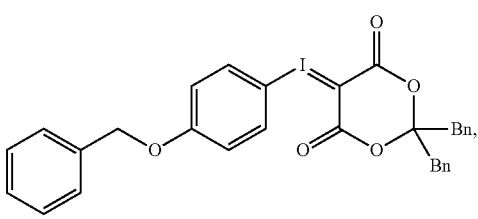
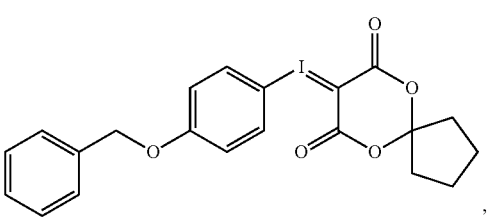
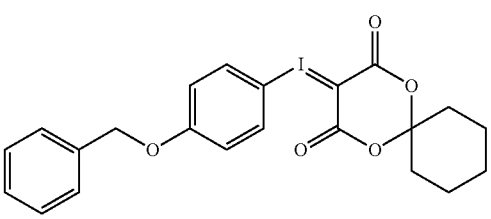
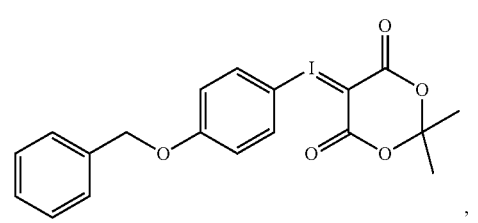
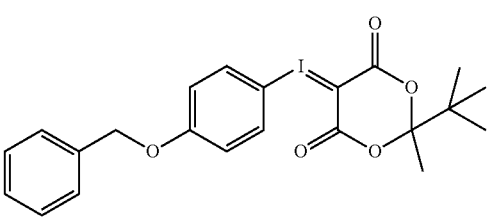
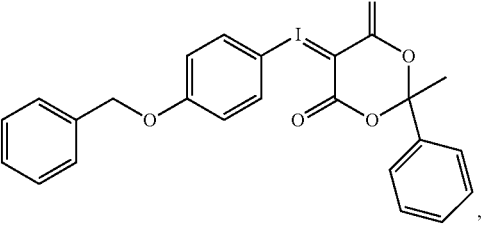

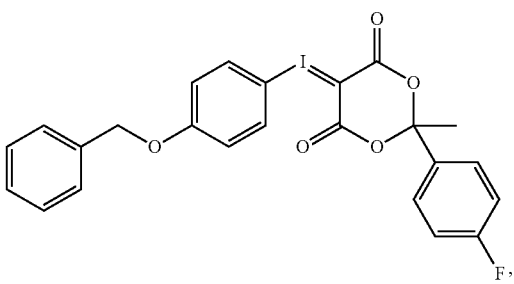

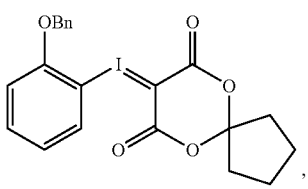

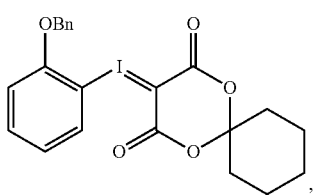

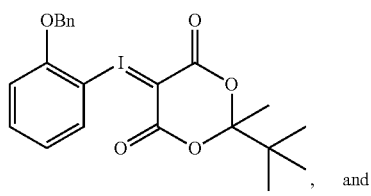

, and

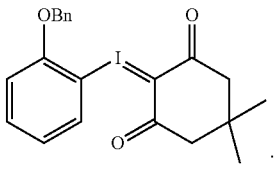

In some embodiments, an intermediate provided herein is selected from compounds of the following formulae:

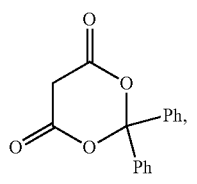 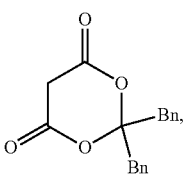

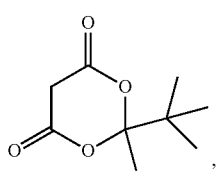, and

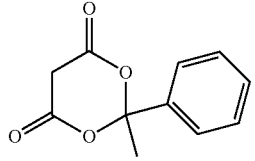

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated that features described as embodiments of the compounds of Formula D can be combined in any suitable combination.

Synthesis

Compounds used in the processes described herein, including salts thereof, can be prepared using known organic synthesis techniques and can be synthesized according to any of numerous possible synthetic routes, such as those in the Schemes below.

The reactions for preparing compounds as described herein can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry." *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds described herein. One skilled in the art would understand that the preparations shown in the Schemes can be modified or optimized using general knowledge of organic chemistry to prepare various compounds within the scope of the disclosure.

The processes provided herein can be performed, e.g., according to the synthesis shown in Scheme 1. For example, an aromatic iodide compound (Ar—I) is oxidized (e.g., in the presence of an oxidizing agent and, optionally, a carboxylate source) and subsequently reacted with a compound of Formula A in a "one-pot" reaction to form a compound of Formula D. The compound of Formula D is then reacted under fluorodeiodination conditions (e.g., reaction with a fluoride source in the presence of a base) to afford an aromatic fluoride compound (Ar—F).

Scheme 1

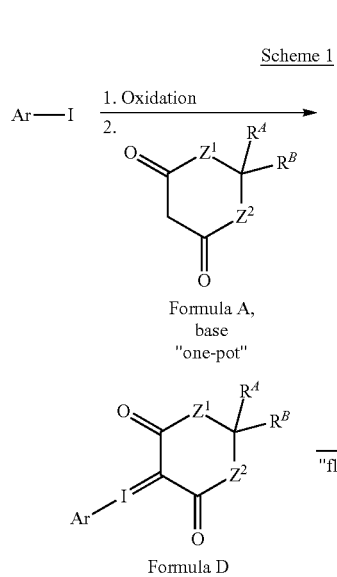

The processes provided herein can be also be performed, e.g., according to the synthesis shown in Scheme 2. For example, an aromatic iodide compound (Ar—I) is first oxidized (e.g., in the presence of an oxidizing agent and, optionally, a carboxylate source) to form iodonium compound (ii). Iodonium (ii) is then reacted with a compound of Formula A under basic conditions (e.g., reaction in the presence of sodium bicarbonate) to form a compound of Formula D. The compound of Formula D is then reacted under fluorodeiodination conditions (e.g., reaction with a fluoride source) to afford an aromatic fluoride compound (Ar—F).

Scheme 2

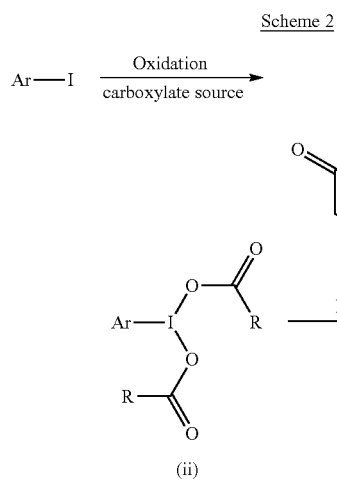

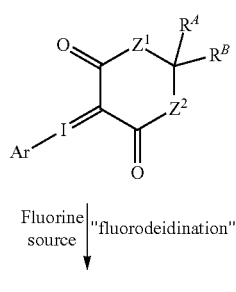

The processes provided herein can be also be performed, e.g., according to the synthesis shown in Scheme 3. For example, an aromatic compound (i) is deaminated under Sandmeyer reaction conditions (e.g., reaction with tBuNO$_2$ in the presence of a strong acid) to afford aromatic compound (ii). Subsequent acid chloride formation (e.g., reaction with oxalyl chloride), amidation (e.g., reaction with NH$_4$OH) and dehydration (e.g., reaction with SO$_2$Cl$_2$) affords the cyano-substituted aromatic compound (iii). Reaction of (iii) with an aromatic alkyne under Sonogashira coupling conditions (e.g., reaction in the presence of Pd(PPh$_3$)$_4$, CuI, and triethylamine, optionally in a microwave reactor) affords the alkyne coupled aromatic compound (iv), which can be used to prepare the corresponding iodonium ylide and aromatic fluoride compound according to the procedures shown in Scheme 1 and Scheme 2.

Scheme 3

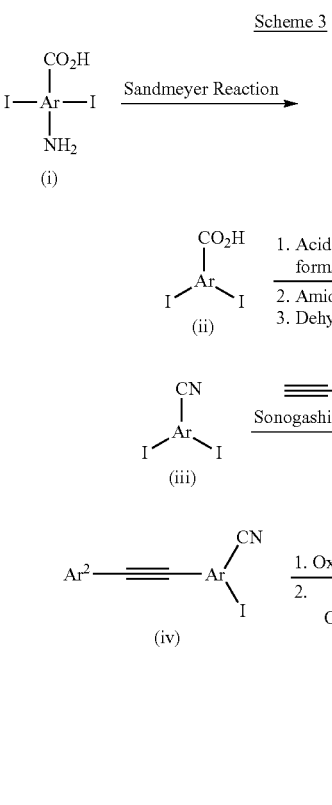

-continued

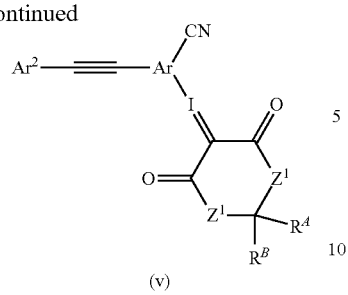

(v)

Starting materials, reagents and intermediates whose synthesis is not described herein are either commercially available, known in the literature, or may be prepared by methods known to one skilled in the art. For example, aromatic iodine compounds can be prepared by electrophilic iodination reactions, from amines via diazonium salts, or by reaction of organometallic compounds with electrophilic iodine.

It will be appreciated by one skilled in the art that the processes described are not the exclusive means by which compounds disclosed herein may be synthesized and that a broad repertoire of synthetic organic reactions is available to be potentially employed in synthesizing compounds disclosed herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (*Journal of Heterocyclic Chemistry*, 1964-2012); Carreira, et al. (Ed.) *Science of Synthesis, Vols*. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, 6$^{th}$ Ed. (Wiley, 2007); Trost et al. (Ed.), *Comprehensive Organic Synthesis* (Pergamon Press, 1991).

Labeled Compounds and Assay Methods

The present disclosure further includes synthetic methods for preparing isotopically-labeled (e.g., radio-labeled compounds) compounds useful in the investigations of biological processes, in normal and abnormal tissues. Thus, another aspect of the present disclosure relates to isotopically-labeled compounds (e.g., radio-labeled compounds) that would be useful not only in imaging techniques but also in vitro and in vivo assays. Accordingly, the present disclosure provides imaging assays that contain such isotopically-labeled compounds.

It is to be understood that a "radiolabeled" is a compound that has incorporated at least one radionuclide. In some embodiments the radionuclide is [$^{18}$F]. In some embodiments, the compound has incorporated 1, 2, or 3 [$^{18}$F] atoms. In some embodiments, the compound has incorporated 1 or 2 [$^{18}$F] atoms. In some embodiments, the compound has incorporated 1 [$^{18}$F] atom.

In some embodiments, the radiolabeled compound is an aromatic fluoride (Ar—F). In some embodiments, the radiolabeled compound is an aromatic [$^{18}$F]fluoride (Ar-$^{18}$F).

In some embodiments, the radiolabeled compound of Ar-$^{18}$F is selected from the group consisting of:

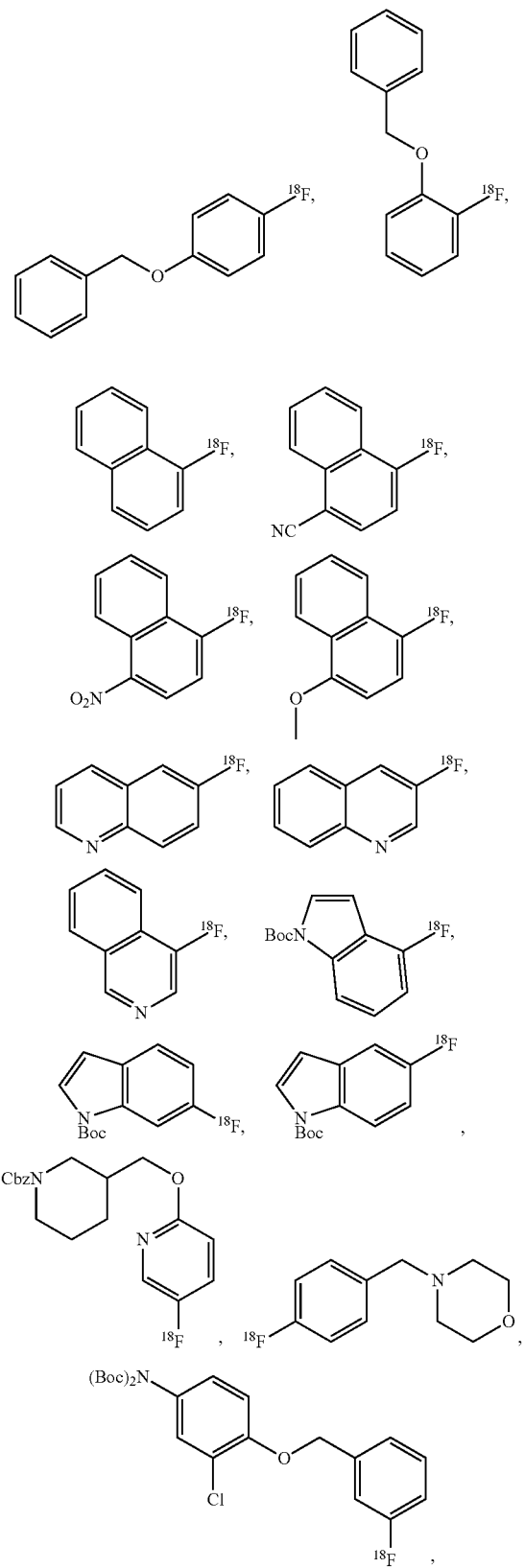

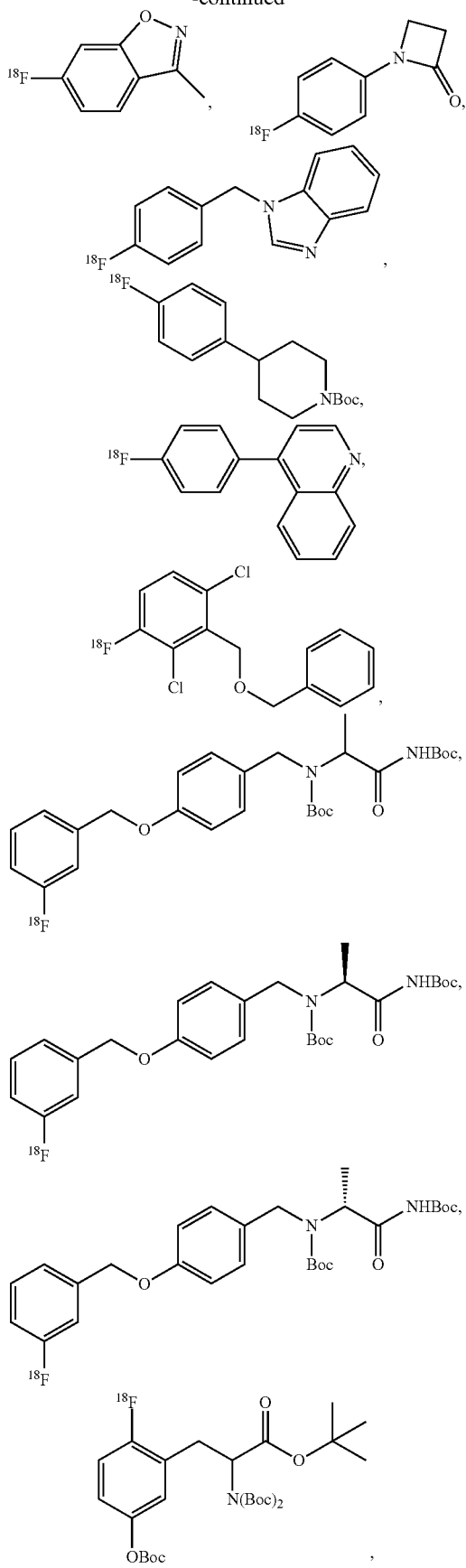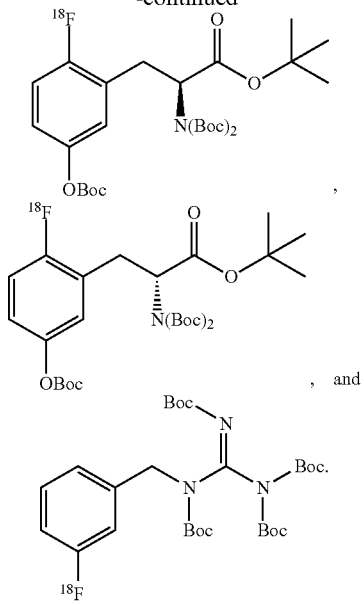

The present application also provides methods of imaging a subject, comprising:

1. preparing a radiolabelled compound (e.g., an [$^{18}$F] aromatic fluoride compound of formula Ar—$^{18}$F, such as the compounds described herein) by any of the methods described herein, or any of the embodiments thereof;

2. administering to the subject the radio-labeled compound (e.g., a radiolabelled [$^{18}$F] aromatic fluoride compound of formula Ar—$^{18}$F);

3. waiting a time sufficient to allow the compound to accumulate at a tissue or cell site to be imaged; and 4. imaging the cell or tissue with an imaging technique (e.g., PET imaging).

The present application also provides methods of diagnosing a disease in a subject, comprising:

1. preparing a radiolabelled compound (e.g., an [$^{18}$F] aromatic fluoride compound of formula Ar—$^{18}$F, such as the compounds described herein) by any of the methods described herein, or any of the embodiments thereof;

2. administering to the subject the radio-labeled compound (e.g., a radiolabelled [$^{18}$F] aromatic fluoride compound of formula Ar—$^{18}$F);

3. waiting a time sufficient to allow the compound to accumulate at a tissue or cell site associated with the disease; and 4. imaging the cell or tissue with an imaging technique.

In some embodiments, the imaging technique is a non-invasive imagining technique. Example imaging techniques include, but are not limited to, fluoroscopic imaging, X-ray imaging, magnetic resonance imaging (MRI), scintigraphic imaging, ultrasound imaging, elastographic imaging, tactile imaging, photoacoustic imaging, thermographic imaging, tomographic imaging, echocardiographic imaging, positron emission tomography imaging, positron emission tomography with computer tomography imaging, and positron emission tomography with magnetic resonance imaging. In some embodiments, the imaging technique is selected from the group consisting of positron emission tomography imaging, positron emission tomography with computer tomography imaging, and positron emission tomography with magnetic resonance imaging.

As used herein, the term "Ci", used alone or in combination with other terms, refers to "Curie", a unit of radioactivity.

As used herein, the term "Bq", used alone or in combination with other terms, refers to "bequerel", the activity of a quantity of radioactive material in which one nucleus decays per second.

As used herein, the term "specific activity", used alone or in combination with other terms, refers to the activity of a given radioisotope per unit mass, for example, Ci/g.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.
Reagents, Solvents and Chromatography All commercial reagents were purchased from Sigma-Aldrich, Alfa Aesar, Fisher Scientific, Acros, Strem Chemicals, Oakwood Chemical, or Matrix Scientific and, unless otherwise stated, used as received. All solvents were of reagent or anhydrous grade quality and purchased from Sigma-Aldrich, Alfa Aesar, or Fisher Scientific. All deuterated solvents were purchased from Cambridge Isotopes. Analytical thin-layer chromatography (TLC) was performed on pre-coated glass-backed plates (EMD TLC Silica gel 60 F254) and visualized using a UV lamp (254 nm), potassium permanganate, and/or iodine stain. Flash column chromatography was performed using a Biotage Isolera One system and preloaded Biotage Zip or refillable Snap silica gel columns. Silica gel for flash chromatography was high purity grade 40-63 μm pore size and purchased from Sigma-Aldrich. Yields refer to purified and spectroscopically pure compounds.

Auxiliary acids, aryl iodides, diacetoxyiodoarenes, and aryl fluorides were obtained from commercial sources, prepared as described previously (see e.g., Rotstein et al., *Nat. Commun.* 2014, 5:4365), or as described herein.
Spectroscopy $^1$H, $^{13}$C, and $^{19}$F NMR spectra were recorded on a Bruker 300 MHz or a Varian Unity/Inova 500 spectrometer, and resonances given in parts per million (ppm) relative residual solvent (19F chemical shifts are uncorrected). Peak multiplicities are designated by the following abbreviations: s, singlet; bs, broad singlet; d, doublet; t, triplet; q, quartet; m, multiplet; dd, doublet of doublets; dt, doublet of triplets: ddd, doublet of doublet of doublets; br, broad; and J, coupling constant in Hz. UV spectra were recorded on either a Hitachi U-1100 Spectrophotometer of a Spectronic Genesys 2 instrument.
Mass Spectrometry HRMS spectra were recorded on a Bruker microTOFII ESI LCMS using positive electrospray ionization (ESI+).

Example 1. Synthesis of Adamantyl Substituted Auxiliary Acid (SPIAd)

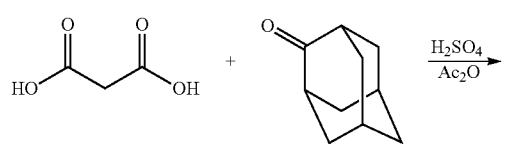

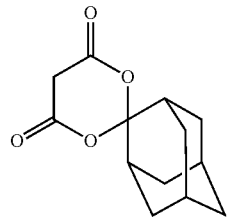

This procedure is based on procedures described in Jiang, et al. *Chin. J. Chem.* 2007, 25:86-89. A mixture of malonic acid (5.0 g, 48 mmol), acetic anhydride (4.8 mL), and conc. H$_2$SO$_4$ (24 μL) was heated with stirring to 60° C. for 15 min. The mixture was then cooled to room temperature, and 2-adamantanone (48 mmol), was added dropwise over 0.5-1 h. The mixture for stirred for an additional 1 h, prior to removal of volatiles by rotary evaporation. The residue was resolubilized in Et$_2$O, and washed three times with water. The organics were dried with MgSO$_4$, filtered and concentrated. The product was precipitated using Et$_2$O and hexanes, and cooling to -25° C. $^1$H NMR (500 MHz, CDCl$_3$) δ 3.60 (s, 2H), 2.25-2.08 (m, 6H), 1.91 (s, 2H), 1.83-1.71 (m, 6H). $^{13}$C NMR (126 MHz, CDCl$_3$) δ 162.94, 109.56, 37.72, 36.77, 36.50, 33.51, 26.12 ppm. HRMS (ESI/[M−H]−) calcd. for C$_{13}$H$_{15}$O$_4$: 235.0976, found 235.0979.

Example 2. General Procedure for Synthesis of Aryliodonium(III) Ylides

To a solution of the auxiliary acid (0.25 mmol) in 10% Na$_2$CO$_3$ (aq) (w/v, 0.75 mL, 0.33 M solution) was added ethanol (1 mL) followed quickly by diacetoxyiodoarene (0.25 mmol). The reaction mixture was vigorously stirred at room temperature for 0.5-4 h, until full conversion of starting materials was determined by TLC. The reaction mixture was then diluted with water (~8 mL), and extracted with DCM (3×10 mL). The combined organic extracts were dried with anhydrous Na$_2$SO$_4$, filtered, and concentrated. To the residue was added ethyl acetate and hexanes to induce precipitation (at room temperature or -25° C.). Solids were collected by filtration and purified by flash chromatography if necessary.

Example 3. General Synthesis of Benzyloxyphenyliododiacetates

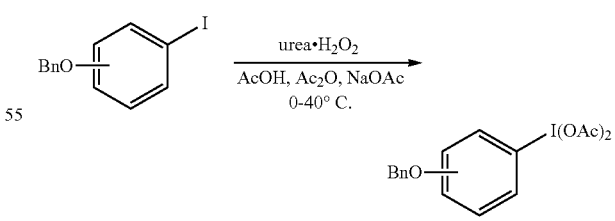

A solution of acetic acid (2.3 mL) and acetic anhydride (0.9 mL) was treated with urea-hydrogen peroxide adduct (1.36 g, 14.5 mmol) at room temperature. Ortho- or para-benzyloxyphenyliodide (1 g, 3.22 mmol) was added, and the resultant mixture cooled to 0° C. Anhydrous sodium acetate (0.53 g, 6.45 mmol) was then slowly added to the mixture. After completion of the addition, the mixture was heated to 40° C. for 2 h. The reaction mixture was cooled to room temperature, diluted with water and extracted three times with dichloromethane. The combined organic fractions were dried over sodium sulfate, filtered and concentrated. The residue was washed with a mixture of hexanes and ethyl ether and filtered to yield a colourless solid.

Para-benzyloxyphenyliododiacetate (2.42 g, 5.64 mmol, 88% yield) matched previously published spectroscopic data (see e.g. Brooks et al., *Chem. Sci.* 2014, 5:4545).

Ortho-benzyloxyphenyliododiacetate (356 mg, 0.83 mmol, 26% yield). $^1$H NMR (300 MHz, CDCl$_3$): δ 8.16 (dd, J=1.4, 7.9 Hz, 1H), 7.56 (td, J=1.4, 8.4 Hz, 1H), 7.44-7.33 (m, 5H), 7.15 (d, J=8.4 Hz, 1H), 7.04 (t, J=7.6 Hz, 1H), 5.29 (s, 2H), 1.97 (s, 6H) ppm. $^{13}$C NMR (75 MHz, CDCl$_3$): δ 176.8, 155.5, 137.9, 135.7, 134.5, 128.9, 128.4, 127.0, 123.2, 113.9, 113.5, 71.4, 20.5 ppm. HRMS (m/z): [M+Na]+ calc. for C$_{17}$H$_{17}$INaO$_5$ 451.0018, found 451.0013.

Examples 4-20

The benzyloxyphenyliodonium(III) ylides of Examples 4-20 were prepared according to the general procedure described above in Example 2 using the benzyloxyphenyliododiacetate prepared according to the procedure described in Example 3.

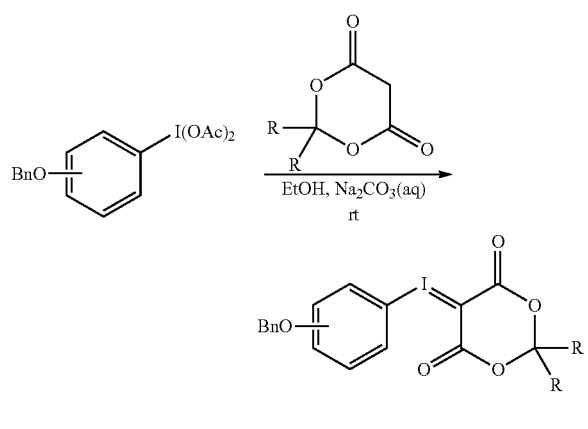

Example 4. 6,10-Dioxaspiro[4.5]decane-7,9-dion-[4-benzyloxyphenyliodonium] ylide

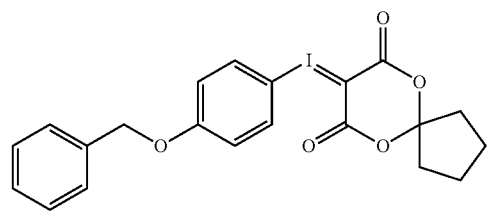 [SMILES: O=C1OC2(CCCC2)OC(=O)C1=Ic1ccc(OCc2ccccc2)cc1]

Colourless solid, 73% yield. $^1$H NMR (300 MHz, CDCl$_3$): δ 7.85 (d, J=9.0 Hz, 2H), 7.40-7.36 (m, 5H), 6.98 (d, J=9.0 Hz, 2H), 5.09 (s, 2H), 2.14 (m, 4H), 1.78 (m, 4H) ppm. $^{13}$C NMR (75 MHz, CDCl$_3$): δ 164.4, 162.1, 138.4, 136.4, 129.0, 127.6, 118.6, 117.4, 114.2, 102.8, 70.6, 58.0, 37.5, 23.5 ppm. HRMS (m/z): [M+Na]+ calc. for C$_{21}$H$_{19}$INaO$_5$ 501.0175, found 501.0172.

Example 5. 1,5-Dioxaspiro[5.5]undecane-2,4-dione-[4-benzyloxyphenyliodonium] ylide

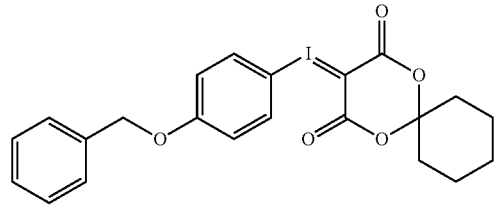 [SMILES: O=C1OC2(CCCCC2)OC(=O)C1=Ic1ccc(OCc2ccccc2)cc1]

Colourless solid, 76% yield. $^1$H NMR (300 MHz, CDCl$_3$): δ 7.85 (d, J=9.1 Hz, 2H), 7.41-7.39 (m, 5H), 6.98 (d, J=9.1 Hz, 2H), 5.09 (s, 2H), 1.97 (m, 4H), 1.67 (m, 4H), 1.46 (m, 2H) ppm. $^{13}$C NMR (75 MHz, CDCl$_3$): δ 163.5, 162.1, 136.4, 135.6, 129.0, 128.6, 127.6, 118.6, 105.3, 103.1, 70.6, 56.9, 34.8, 24.8, 22.6 ppm. HRMS (m/z): [M+Na]+ calc. for C$_{22}$H$_{21}$INaO$_5$ 515.0331, found 515.0330.

Example 6. 1,5-Dioxaspiro[5.7]tridecane-2,4-dion-[4-benzyloxyphenyliodonium] ylide

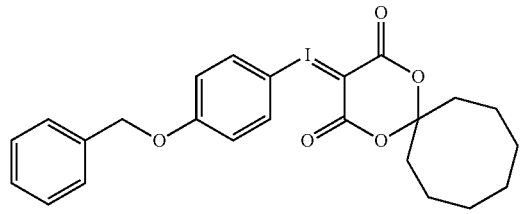 [SMILES: O=C1OC2(CCCCCCC2)OC(=O)C1=Ic1ccc(OCc2ccccc2)cc1]

Yellow solid, 18% yield. $^1$H NMR (300 MHz, CDCl$_3$): δ 7.85 (d, J=9.0 Hz, 2H), 7.40-7.34 (m, 5H), 6.97 (d, J=9.0 Hz, 2H), 5.09 (s, 2H), 2.17 (m, 4H), 1.66 (br s, 4H), 1.57 (br s, 6H) ppm. $^{13}$C NMR (75 MHz, CDCl$_3$): δ 163.4, 162.1, 136.4, 135.6, 129.0, 128.6, 127.6, 118.6, 109.0, 103.1, 70.6, 56.9, 33.8, 27.8, 24.6, 21.5 ppm. HRMS (m/z): [M+Na]+ calc. for C$_{24}$H$_{25}$INaO$_4$ 543.0644, found 543.0640.

Example 7. (1r,3r,5r,7r)-Spiro[adamantane-2,2'-[1,3]dioxane]-4',6'-dion-[4-benzyloxyphenyliodonium] ylide

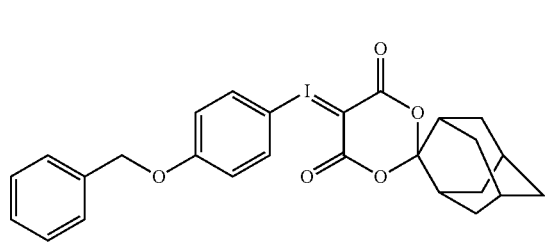 [SMILES: O=C1OC2(OC(=O)C1=Ic1ccc(OCc3ccccc3)cc1)C1CC3CC(C1)CC2C3]

Colourless solid, 86% yield. $^1$H NMR (300 MHz, CDCl$_3$): δ 7.84 (d, J=9.0 Hz, 2H), 7.40-7.34 (m, 5H), 6.97 (d, J=9.0, 2H), 5.09 (s, 2H), 2.40 (br s, 2H), 2.17 (br s, 2H), 2.13 (br s, 2H), 1.84 (br s, 2H), 1.66 (br s, 4H), 1.62 (br s, 2H) ppm. $^{13}$C NMR (75 MHz, CDCl$_3$): δ 163.5, 162.1, 136.3, 135.7, 128.9, 128.6, 127.6, 118.5, 107.6, 103.1, 70.6, 57.0, 37.3, 35.7, 33.9, 26.7 ppm. HRMS (m/z): [M+Na]+ calc. for $C_{26}H_{25}INaO_5$ 567.0644, found 567.0641.

Example 8. 2,2-Diphenyl-1,3-dioxane-4,6-dion-[4-benzyloxyphenyliodonium] ylide

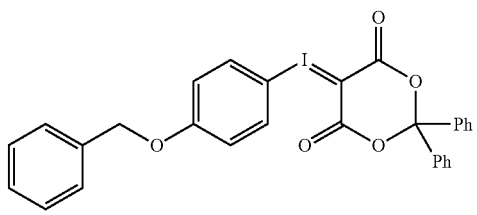 [SMILES: O=C1OC(c2ccccc2)(c2ccccc2)OC(=O)C1=Ic1ccc(OCc2ccccc2)cc1]

Colourless solid, 56% yield. $^1$H NMR (300 MHz, CDCl$_3$): δ 7.63-7.59 (m, 4H), 7.40-7.34 (m, 8H), 7.30-7.27 (m, 5H), 6.82 (d, J=9.0 Hz), 5.07 (s, 2H) ppm. $^{13}$C NMR (75 MHz, CDCl$_3$): δ 163.3, 161.7, 140.6, 135.7, 134.5, 129.0, 128.9, 128.6, 128.6, 127.5, 126.0, 118.8, 104.9, 102.2, 70.6, 58.8 ppm. HRMS (m/z): [M+Na]+ calc. for $C_{29}H_{21}INaO_5$ 599.0331, found 599.0334.

Example 9. 2,2-Dibenzyl-1,3-dioxane-4,6-dion-[4-benzyloxyphenyliodonium] ylide

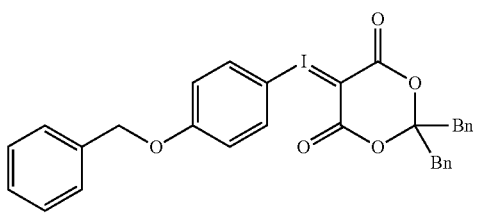 [SMILES: O=C1OC(Cc2ccccc2)(Cc2ccccc2)OC(=O)C1=Ic1ccc(OCc2ccccc2)cc1]

Pale yellow solid, 57% yield. $^1$H NMR (300 MHz, CDCl$_3$): δ 7.63-7.59 (m, 4H), 7.40-7.34 (m, 8H), 7.30-7.27 (m, 5H), 6.82 (d, J=9.0 Hz), 5.07 (s, 2H), 3.19 (s, 4H) ppm. $^{13}$C NMR (75 MHz, CDCl$_3$): δ 162.9, 162.1, 136.3, 135.6, 134.4, 131.2, 128.9, 128.6, 128.3, 127.6, 127.1, 118.6, 106.1, 103.2, 70.6, 56.7, 44.0 ppm. HRMS (m/z): [M+Na]+ calc. for $C_{31}H_{25}INaO_5$ 627.0644, found 627.0642.

Example 10. 5,5-Dimethylcyclohexane-1,3-dion-[4-benzyloxyphenyliodonium] ylide

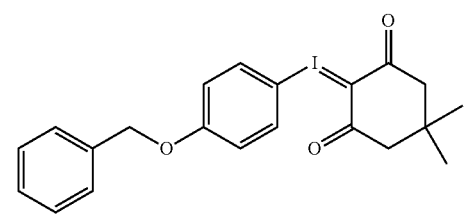 [SMILES: CC1(C)CC(=O)C(=Ic2ccc(OCc3ccccc3)cc2)C(=O)C1]

Colourless solid, 71% yield. $^1$H NMR (300 MHz, CDCl$_3$): δ 7.81 (d, J=9.0 Hz, 2H), 7.38 (m, 5H), 6.92 (d, J=9.0 Hz, 2H), 5.06 (s, 2H), 2.48 (s, 4H), 1.04 (s, 6H) ppm. $^{13}$C NMR (75 MHz, CDCl$_3$): δ 188.5, 161.6, 136.7, 135.8, 128.9, 128.6, 127.6, 118.3, 100.8, 95.4, 70.5, 50.9, 32.2, 28.3 ppm. HRMS (m/z): [M+Na]+ calc. for $C_{21}H_{21}INaO_3$ 471.0433, found 471.0428.

Example 11. 2-(tert-Butyl)-2-methyl-1,3-dioxane-4,6-dion-[4-benzyloxyphenyliodonium]ylide

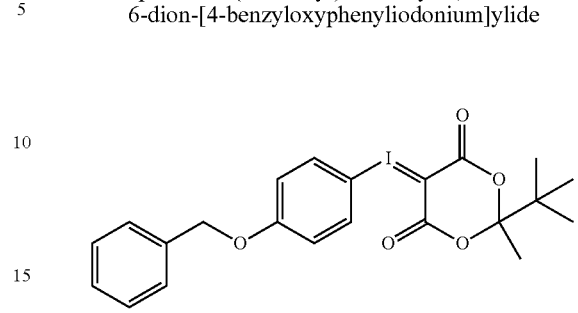

Colourless solid, 86% yield. $^1$H NMR (300 MHz, CDCl$_3$): δ 7.86 (d, J=9.1 Hz, 2H), 7.39 (m, 5H), 6.98 (d, J=9.1 Hz, 2H), 5.09 (s, 2H), 1.61 (s, 3H), 1.08 (s, 9H) ppm. $^{13}$C NMR (75 MHz, CDCl$_3$): δ 163.8, 162.1, 136.4, 135.6, 129.0, 128.6, 127.6, 118.6, 109.7, 103.2, 70.6, 56.9, 39.0, 24.7, 18.5 ppm.

HRMS (m/z): [M+Na]+ calc. for $C_{22}H_{23}INaO_5$ 517.0488, found 517.0490.

Example 12. 2-Methyl-2-phenyl-1,3-dioxane-4,6-dion-[4-benzyloxyphenyliodonium] ylide

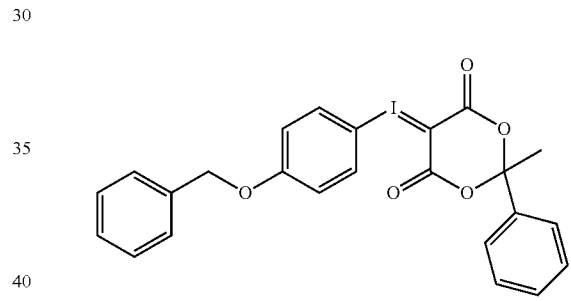

Colourless solid, 93% yield. $^1$H NMR (300 MHz, CDCl$_3$): δ 7.54-7.52 (m, 3H), 7.40-7.34 (m, 9H), 6.82 (d, J=9.1 Hz, 2H), 5.07 (s, 2H), 11.87 (s, 3H) ppm. $^{13}$C NMR (75 MHz, CDCl$_3$): δ 163.7, 161.7, 142.0, 138.4, 135.7, 134.5, 129.0, 128.7, 128.6, 127.5, 125.1, 118.7, 104.9, 102.2, 70.6, 58.6, 29.7 ppm. HRMS (m/z): [M+Na]+ calc. for $C_{24}H_{19}INaO_5$ 537.0175, found 537.0180.

Example 13. 2-(4-Fluorophenyl)-2-methyl-1,3-dioxane-4,6-dion-[4-benzyloxyphenyliodonium] ylide

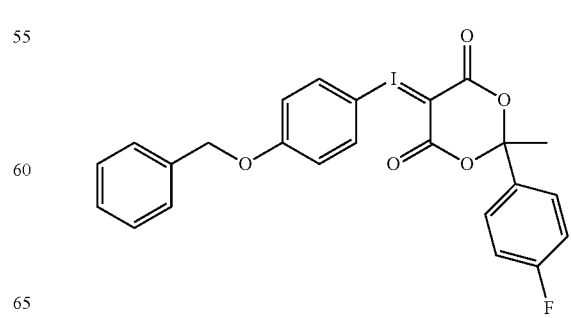

Colourless solid, 67% yield. $^1$H NMR (300 MHz, CDCl$_3$): δ 7.52-7.39 (m, 9H), 6.95 (t, J=8.6 Hz, 2H), 6.85 (d, J=7.2 Hz), 5.08 (s, 2H), 1.85 (s, 3H) ppm. $^{13}$C NMR (75 MHz, CDCl$_3$): δ 163.5, 161.9, 138.0, 135.6, 135.1, 129.0, 128.8, 128.6, 127.6, 127.0 (d), 124.4, 118.6, 115.5 (d), 103.4 (d), 70.6, 58.9, 29.6 ppm. $^{19}$F NMR (282 MHz, CDCl$_3$): 109.2 (m) ppm. HRMS (m/z): [M+Na]$^+$ calc, for C$_{24}$H$_{18}$FINaO$_5$ 555.0081, found 555.0083.

Example 14. 6,10-Dioxaspiro[4.5]decane-7,9-dion-[2-benzyloxyphenyliodonium] ylide

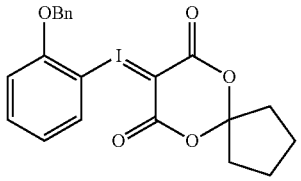 [SMILES: O=C1OC2(CCCC2)OC(=O)C1=Ic1ccccc1OCc1ccccc1]

Colourless solid, 88% yield. $^1$H NMR (300 MHz, CDCl$_3$): δ 7.48-7.41 (m, 6H), 7.35 (dd, J=1.3, 8.1 Hz, 1H), 7.11 (t, J=8.1 Hz, 1H), 7.03 (d, J=8.2 Hz, 1H), 5.21 (s, 2H), 2.25 (m, 4H), 1.84 (m, 4H) ppm. $^{13}$C NMR (75 MHz, CDCl$_3$): δ 164.6, 154.5, 134.8, 129.2, 129.1, 128.5, 127.9, 124.9, 114.4, 113.8, 102.2, 72.3, 48.2, 37.6, 23.6 ppm. HRMS (m/z): [M+Na]$^+$ calc, for C$_{21}$H$_{19}$INaO$_5$ 501.0175, found 501.0173.

Example 15. 1,5-Dioxaspiro[5.5]undecane-2,4-dione-[2-benzyloxyphenyliodonium] ylide

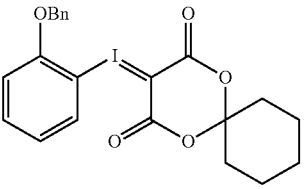 [SMILES: O=C1OC2(CCCCC2)OC(=O)C1=Ic1ccccc1OCc1ccccc1]

Colourless solid, 80% yield. $^1$H NMR (300 MHz, CDCl$_3$): δ 7.48-7.41 (m, 6H), 7.34 (dd, J=1.1, 8.1 Hz, 1H), 7.10 (t, J=8.2 Hz, 1H), 7.03 (d, J=8.2 Hz, 1H), 5.21 (s, 2H), 2.08 (m, 4H), 1.73 (m, 4H), 1.49 (m, 2H) ppm. $^{13}$C NMR (75 MHz, CDCl$_3$): δ 163.7, 154.5, 134.8, 132.7, 129.2, 129.1, 128.7, 127.8, 124.9, 113.8, 105.5, 102.4 ppm. HRMS (m/z): [M+Na]$^+$ calc, for C$_{22}$H$_{21}$INaO$_5$ 515.0331, found 515.0336.

Example 16. 1,5-Dioxaspiro[5.7]tridecane-2,4-dion-[4-benzyloxyphenyliodonium] ylide

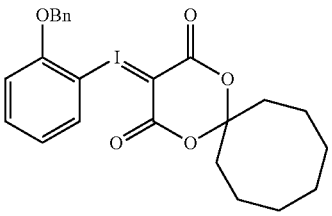 [SMILES: O=C1OC2(CCCCCCC2)OC(=O)C1=Ic1ccccc1OCc1ccccc1]

Colourless solid, 71% yield. $^1$H NMR (300 MHz, CDCl$_3$): δ 7.45-7.41 (m, 6H), 7.33 (dd, J=1.3, 8.1 Hz, 1H), 7.10 (t, J=7.3 Hz, 1H), 5.20 (s, 2H), 2.28 (m, 4H), 1.72 (br s, 4H), 1.60 (br s, 6H) ppm. $^{13}$C NMR (75 MHz, CDCl$_3$): δ 163.6, 154.5, 134.8, 132.7, 129.2, 129.1, 128.6, 127.8, 124.9, 113.8, 109.2, 102.5, 72.3, 47.1, 33.9, 27.8, 24.6, 21.6 ppm. HRMS (m/z): [M+Na]$^+$ calc, for C$_{24}$H$_{25}$INaO$_5$ 543.0644, found 543.0642.

Example 17. (1r,3r,5r,7r)-Spiro[adamantane-2,2'-[1,3]dioxane]-4',6'-dion-[2-benzyloxyphenyliodonium] ylide

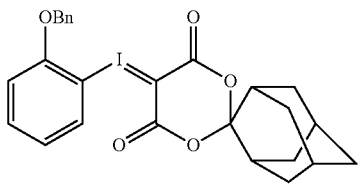 [SMILES: O=C1OC2(OC(=O)C1=Ic1ccccc1OCc1ccccc1)C1CC3CC(C1)CC2C3]

Colourless solid, 76% yield. $^1$H NMR (300 MHz, CDCl$_3$): δ 7.45-7.42 (m, 6H), 7.33 (dd, J=1.3, 8.1 Hz, 1H), 7.10 (t, J=8.1 Hz, 1H), 7.02 (d, J=8.2 Hz, 1H), 5.21 (s, 2H), 2.53 (br s, 2H), 2.23 (br s, 2H), 2.19 (br s, 2H), 1.88 (br s, 2H), 1.75 (m, 6H) ppm. $^{13}$C NMR (75 MHz, CDCl$_3$): δ 163.6, 154.5, 134.9, 132.7, 129.2, 129.1, 128.7, 127.8, 124.9, 113.8, 107.8, 102.5, 72.3, 60.5, 37.3, 35.8, 33.9, 26.7 ppm. HRMS (m/z): [M+Na]$^+$ calc, for C$_{26}$H$_{25}$INaO$_5$ 567.0644, found 567.0647.

Example 18. 2-(tert-Butyl)-2-methyl-1,3-dioxane-4,6-dion-[4-benzyloxyphenyliodonium] ylide

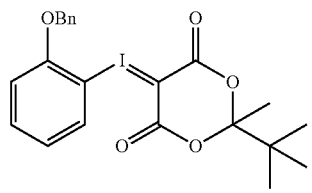 [SMILES: CC(C)(C)C1(C)OC(=O)C(=Ic2ccccc2OCc2ccccc2)C(=O)O1]

Colourless solid, 68% yield. $^1$H NMR (300 MHz, CDCl$_3$): δ 7.43 (m, 6H), 7.32 (dd, J=1.4, 8.1 Hz, 1H), 7.10 (dt, J=1.2, 8.0 Hz, 1H), 7.03 (d, J=8.2 Hz, 1H), 5.21 (s, 2H), 1.75 (s, 3H), 1.15 (s, 9H) ppm. $^{13}$C NMR (75 MHz, CDCl$_3$): δ 164.0, 154.6, 134.8, 132.7, 129.2, 129.1, 128.6, 127.9, 124.9, 113.8, 109.8, 102.6, 72.3, 47.2, 39.2, 24.8, 18.7 ppm. HRMS (m/z): [M+Na]$^+$ calc, for C$_2$H$_{23}$INaO$_5$ 517.0488, found 517.0491.

Example 19. 5,5-Dimethylcyclohexane-1,3-dion-[2-benzyloxyphenyliodonium] ylide

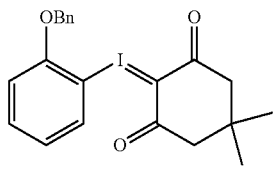 [SMILES: CC1(C)CC(=O)C(=Ic2ccccc2OCc2ccccc2)C(=O)C1]

Colourless solid, 80% yield. $^1$H NMR (300 MHz, CDCl$_3$): δ 7.44-7.36 (m, 6H), 7.21 (d, J=8.4 Hz, 1H), 7.02-6.97 (m, 2H), 5.21 (s, 2H), 2.58 (s, 4H), 1.16 (s, 6H) ppm. $^{13}$C NMR (75 MHz, CDCl$_3$): δ 189.5, 155.0, 135.1, 132.2, 129.8, 129.1, 128.9, 127.7, 124.5, 113.6, 101.0, 87.3, 72.0, 51.0, 32.2, 28.5 ppm. HRMS (m/z): [M+Na]$^+$ calc. for C$_{21}$H$_{21}$INaO$_3$ 471.0433, found 471.0430.

Example 20. 2,2-Dimethyl-1,3-dioxane-4,6-dion-[2-benzyloxyphenyliodonium] ylide

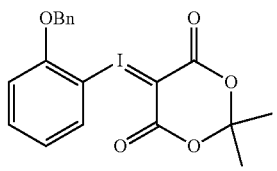 [SMILES: CC1(C)OC(=O)C(=Ic2ccccc2OCc2ccccc2)C(=O)O1]

Colourless solid, 31% yield. $^1$H NMR (300 MHz, CDCl$_3$): δ 7.45-7.33 (m, 7H), 7.10-7.00 (m, 2H), 5.18 (s, 2H), 1.77 (s, 6H) ppm. $^{13}$C NMR (75 MHz, CDCl$_3$): δ 163.8, 154.6, 134.9, 132.8, 129.1, 129.1, 128.8, 127.9, 124.9, 113.8, 104.8, 102.4, 72.2, 47.7, 26.1 ppm. HRMS (m/z): [M+Na]$^+$ calc. for C$_{19}$H$_{17}$INaO$_5$ 475.0018, found 475.0021.

Example 21. (1r,3r,5r,7r)-Spiro[adamantane-2,2'-[1,3]dioxane]-4',6'-dion-[1-naphthyliodonium] ylide

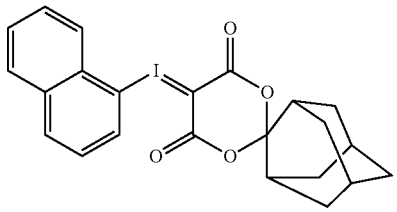 [SMILES: O=C1OC2(OC(=O)C1=Ic1cccc3ccccc13)C1CC3CC(C1)CC2C3]

This compound was prepared according the general procedure described above in Example 2 using naphthyl-1-iododiacetate.

Colourless solid, 55% yield. $^1$H NMR (300 MHz, CDCl$_3$): δ 8.26 (d, J=7.5 Hz, 1H), 8.20 (d, J=8.4 Hz, 1H), 8.07 (d, J=8.1 Hz, 1H), 7.87 (d, J=8.1 Hz, 1H), 7.74 (t, J=7.5 Hz, 1H) 7.63 (t, J=7.5 Hz, 1H), 7.44 (t, J=7.9 Hz, 1H), 2.34 (br s, 2H), 2.14-2.09 (overlapping br s, 4H), 1.82 (br s, 2H), 1.67 (br s, 4H), 1.62 (br s, 2H) ppm. $^{13}$C NMR (75 MHz, CDCl$_3$): δ 163.4, 135.8, 135.2, 133.6, 131.5, 129.9, 129.2, 128.8, 128.2, 127.2, 116.3, 107.7, 54.6, 37.3, 35.7, 33.8, 26.7 ppm. HRMS (m/z): [M+Na]$^+$ calc. for C$_{23}$H$_{21}$INaO$_4$ 511.0382, found 511.0387.

Example 22. (1r,3r,5r,7r)-Spiro[adamantane-2,2'-[1,3]dioxane]-4',6'-dion-[4-cyanonaphthyl-1-iodonium] ylide

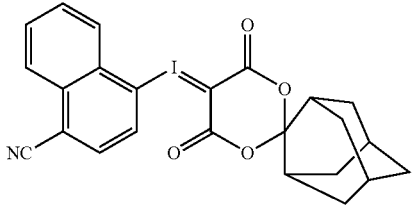 [SMILES: N#Cc1ccc(I=C2C(=O)OC3(OC2=O)C2CC4CC(C2)CC3C4)c2ccccc12]

A solution of 4-iodo-1-naphthonitrile (56 mg, 0.2 mmol) in acetic acid (1.3 mL) was treated with mCPBA (49 mg, 0.22 mmol) at room temperature. The reaction was heated to 55° C. for 24 h following a previously reported procedure (see e.g., Togo et al., *Synlett* 2012, 23:2663-2666). When TLC indicated no remaining starting material, water was added to the reaction mixture and the product extracted with dichloromethane and precipitated with diethyl ether and hexanes at −78° C. After filtration, the crude residue was immediately dissolved in ethanol and the general procedure for iodonium(III) ylide preparation was completed.

Colourless solid, 16% yield. $^1$H NMR (300 MHz, CDCl$_3$): δ 8.30 (m, 3H), 7.87 (m, 3H), 2.35 (br s, 2H), 2.13-2.08 (overlapping br s, 4H), 1.83 (br s, 2H), 1.70-1.64 (overlapping br s, 6H) ppm. $^{13}$C NMR (75 MHz, CDCl$_3$): δ 163.3, 133.7, 133.6, 133.0, 131.4, 131.1, 130.8, 129.6, 126.7, 121.2, 116.1, 115.6, 108.2, 54.6, 37.2, 35.8, 33.8, 26.6 ppm. HRMS (m/z): [M+Na]$^+$ calc. for C$_{24}$H$_{20}$INNaO$_4$ 536.0335, found 536.0337.

Example 23. (1r,3r,5r,7r)-Spiro[adamantane-2,2'-[1,3]dioxane]-4',6'-dion-[4-nitronaphthyl-1-iodonium] ylide

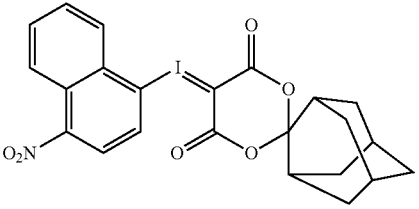 [SMILES: O=C1OC2(OC(=O)C1=Ic1ccc([N+](=O)[O-])c3ccccc13)C1CC3CC(C1)CC2C3]

The title compound was prepared from 1-iodo-4-methoxynaphthalene following a similar procedure to that used to prepare the cyano-substituted analogue described in Example 22, performing the oxidation at 55° C. for 72 h.

Colourless solid, 29% yield. $^1$H NMR (300 MHz, CDCl$_3$): δ 8.46-8.42 (m, 1H), 8.36-8.31 (m, 2H), 8.05 (d, J=8.0 Hz, 1H), 7.91-7.88 (m, 2H), 2.38 (br s, 2H), 2.16 (br s, 2H), 2.12 (br s, 2H), 1.85 (br s, 2H), 1.71 (br s, 4H), 1.67 (br s, 2H) ppm. $^{13}$C NMR (75 MHz, CDCl$_3$): δ 163.3, 150.4, 133.4, 132.2, 131.3, 131.2, 129.4, 126.3, 124.4, 123.7, 120.9, 108.2, 54.8, 37.2, 35.8, 33.8, 26.6 ppm. HRMS (m/z): [M+Na]$^+$ calc. for C$_{23}$H$_{20}$INNaO$_6$ 556.0233, found 556.0235.

Example 24. (1r,3r,5r,7r)-Spiro[adamantane-2,2'-[1,3]dioxane]-4',6'-dion-[4-methoxynaphthyl-1-iodonium] ylide

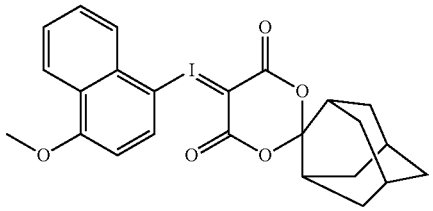 [SMILES: COc1ccc(I=C2C(=O)OC3(OC2=O)C2CC4CC(C2)CC3C4)c2ccccc12]

A solution of 1-iodo-4-methoxynaphthalene (85 mg, 0.3 mmol) in acetone and acetic acid (4:1, 2.2 mL) was cooled to 0° C. and treated with a solution of DMDO in acetone. The reaction mixture was stirred at 0° C. for 1 h, then warmed to room temperature and stirred for an additional 3 h. The reaction mixture was then concentrated, diluted with ethanol (1.2 mL), treated with (1r,3r,5r,7r)-spiro[adamantane-2,2'-[1,3]dioxane]-4',6'-dione (71 mg) in 10% aqueous sodium carbonate (0.9 mL) and the pH was adjusted to ~10 using 10% aqueous sodium carbonate. The reaction was then stirred for 2-4 h, and worked up and purified as described above.

Colourless solid, 25% yield, $^1$H NMR (300 MHz, CDCl$_3$): δ 8.30-8.21 (m, 3H), 7.74 (dt, J=1.3, 8.4 Hz, 1H), 7.60 (t, J=7.2 Hz, 1H), 6.74 (d, J=8.4 Hz, 1H), 4.05 (s, 3H), 2.31 (br s, 2H), 2.13 (br s, 2H), 2.08 (br s, 2H), 1.80 (br s, 2H), 1.64 (overlapping br s, 6H) ppm. $^{13}$C NMR (75 MHz, CDCl$_3$): δ 156.7, 156.5, 137.0, 134.8, 133.2, 131.9, 128.3, 126.8, 126.1, 122.6, 111.5, 105.7, 88.2, 55.8, 38.1, 36.7, 33.6, 26.1 ppm. HRMS (m/z): [M+Na]$^+$ calc. for C$_{24}$H$_{23}$INaO$_5$ 541.0488, found 541.0487.

Example 25. (1r,3r,5r,7r)-Spiro[adamantane-2,2'-[1,3]dioxane]-4',6'-dion-[quinolin-6-iodonium]ylide

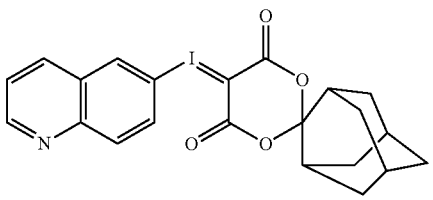 [SMILES: O=C1OC2(OC(=O)C1=Ic1ccc3ncccc3c1)C1CC3CC(C1)CC2C3]

Under a nitrogen atmosphere, 6-iodoquinoline (102 mg, 0.4 mmol) was dissolved in anhydrous acetonitrile (2.4 mL). A solution of trimethylsilylacetate (0.15 mL, 1 mmol) in acetonitrile (2.4 mL) was added, followed by SelectFluor (184 mg, 0.52 mmol). This mixture was stirred at room temperature for 3-8 h or until complete consumption of the aryl iodide was observed by TLC. Volatiles were removed under reduced pressure, and the residue was taken up in dichloromethane and filtered to remove solids. The filtrate was washed with acetate buffer (0.5 M, 1:1 NaOAc:AcOH), dried over anhydrous sodium sulfate, filtered, and concentrated. The crude aryliodonium(III) diacetate was then used in the general procedure for iodonium(III) ylide formation, as described above.

Colourless solid, 33% yield. $^1$H NMR (300 MHz, CDCl$_3$): δ 9.06 (dd, J=1.7, 4.3 Hz, 1H), 8.43 (d, J=1.9 Hz), 8.21 (dd, J=1.7, 6.9 Hz, 1H), 8.13 (d, J=8.8 Hz, 1H) 8.10 (dd, J=1.9, 9.1 Hz, 1H), 7.56 (dd, J=4.2, 8.3 Hz, 1H), 2.44 (br s, 2H), 2.19 (br s, 2H), 2.15 (br s, 2H), 1.86 (br s, 2H), 1.72 (br s, 4H), 1.68 (br s, 2H) ppm. $^{13}$C NMR (75 MHz, CDCl$_3$): δ 163.7, 153.1, 148.7, 136.3, 134.0, 133.7, 131.9, 129.8, 122.8, 111.7, 107.9, 56.3, 37.2, 35.7, 33.9, 26.6 ppm. HRMS (m/z): [M+Na]$^+$ calc. for C$_{22}$H$_{20}$INNaO$_4$ 512.0335, found 512.0332.

Example 26. (1r,3r,5r,7r)-Spiro[adamantane-2,2'-[1,3]dioxane]-4',6'-dion-[quinolin-3-iodonium] ylide

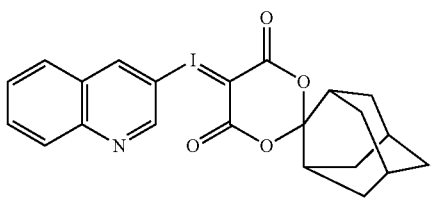 [SMILES: O=C1OC2(OC(=O)C1=Ic1cnc3ccccc3c1)C1CC3CC(C1)CC2C3]

The title compound was prepared from 3-iodoquinoline following a similar procedure to that used to prepare 6-substituted isomer described in Example 25.

Colourless solid, 48% yield. $^1$H NMR (300 MHz, CDCl$_3$): δ 9.23 (d, J=2.1 Hz, 1H), 8.82 (d, J=1.6 Hz, 1H), 8.17 (d, J=8.9 Hz, 1H), 7.92-7.86 (m, 2H), 7.70 (t, J=7.1 Hz, 1H), 2.41 (br s, 2H), 2.17 (br s, 2H), 2.13 (br s, 2H), 1.85 (br s, 2H), 1.71 (br s, 4H), 1.59 (br s, 2H) ppm. $^{13}$C NMR (75 MHz, CDCl$_3$): δ 163.7, 150.5, 148.3, 142.5, 132.6, 129.8, 129.7, 128.7, 128.5, 109.7, 107.9, 56.4, 37.2, 35.7, 33.8, 26.6 ppm. HRMS (m/z): [M+Na]$^+$ calc. for C$_{22}$H$_{20}$INNaO$_4$ 512.0335, found 512.0332.

Example 27. (1r,3r,5r,7r)-Spiro[adamantane-2,2'-[1,3]dioxane]-4',6'-dion-[isoquinolin-4-iodonium] ylide

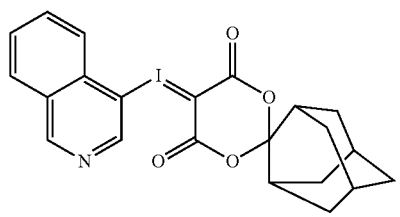 [SMILES: O=C1OC2(OC(=O)C1=Ic1cncc3ccccc13)C1CC3CC(C1)CC2C3]

The title compound was prepared from 4-iodoisoquinoline following a similar procedure to that used to prepare the quinoline iodonium ylides described in Examples 25-26.

Yellow solid, 12% yield. $^1$H NMR (300 MHz, CDCl$_3$): δ 9.41 (s, 1H), 9.24 (s, 1H), 8.37 (d, J 8.3 Hz, 1H), 8.04 (d, J=8.8 Hz, 1H), 7.99 (d, J=7.2 Hz, 1H), 7.83 (t, J=7.2 Hz), 2.32 (br s, 2H), 2.14 (br s, 2H), 2.09 (br s, 2H), 1.82 (br s, 2H), 1.67 (br s, 4H), 1.63 (br s, 2H) ppm. $^{13}$C NMR (75 MHz, CDCl$_3$): δ 163.3, 157.14, 152.7, 150.7, 134.3, 132.2, 130.9, 130.0, 128.9, 128.5, 107.8, 39.4, 37.3, 35.7, 33.8, 26.6 ppm. HRMS (m/z): [M+Na]$^+$ calc. for C$_{22}$H$_{20}$INNaO$_4$ 512.0335, found 512.0337.

Example 28. (1r,3r,5r,7r)-Spiro[adamantane-2,2'-[1,3]dioxane]-4',6'-dion-[N-Boc-indol-4-iodonium] ylide

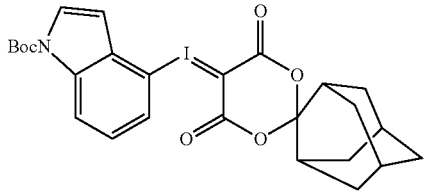 [SMILES: CC(C)(C)OC(=O)n1ccc2c(I=C3C(=O)OC4(OC3=O)C3CC5CC(C3)CC4C5)cccc21]

A solution of 1-Boc-4-iodoindole (103 mg, 0.3 mmol) in acetone and acetic acid (4:1, 2.2 mL) was cooled to 0° C. and treated with a solution of DMDO in acetone. The reaction mixture was stirred at 0° C. for 1 h, then warmed to room temperature and stirred for an additional 3 h. The reaction mixture was then concentrated, diluted with ethanol (1.2 mL), treated with (1r,3r,5r,7r)-spiro[adamantane-2,2'-[1,3]dioxane]-4',6'-dione (71 mg) in 10% aqueous sodium carbonate (0.9 mL) and the pH was adjusted to ~10 using 10% aqueous sodium carbonate. The reaction was then stirred for 2-4 h, and worked up and purified as described above.

Colourless solid, 55% yield. $^1$H NMR (300 MHz, CDCl$_3$): δ 8.43 (d, J=8.3 Hz, 1H), 7.90 (d, J=7.8 Hz, 1H), 7.75 (d, J=3.8 Hz, 1H), 7.30 (d, J=8.1 Hz, 1H), 6.92 (d, J=3.8 Hz, 1H), 2.34 (br s, 2H), 2.15 (br s, 2H), 2.11 (br s, 2H), 1.68 (s, 9H), 1.63 (br s, 2H), 1.58 (br s, 4H) ppm. $^{13}$C NMR (75 MHz, CDCl$_3$): δ 163.3, 149.0, 136.0, 132.6, 130.4, 128.8, 125.9, 119.9, 108.4, 107.5, 104.9, 85.4, 55.9, 37.3, 35.7, 33.8, 28.2, 26.7 ppm. HRMS (m/z): [M+Na]$^+$ calc, for C$_{26}$H$_{28}$INNaO$_6$ 600.0859, found 600.0860.

Example 29. (1r,3r,5r,7r)-Spiro[adamantane-2,2'-[1,3]dioxane]-4',6'-dion-[N-Boc-indol-5-iodonium] ylide

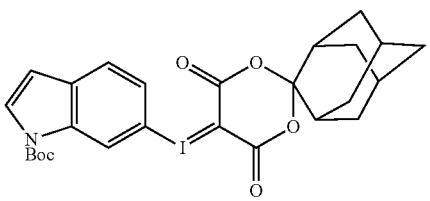 [SMILES: CC(C)(C)OC(=O)n1ccc2ccc(I=C3C(=O)OC4(OC3=O)C3CC5CC(C3)CC4C5)cc21]

The title compound was prepared from N-Boc-6-iodoindole following a similar procedure to that used to prepare the indole-4-iodonium ylide described in Example 28.

$^1$H NMR (300 MHz, CDCl$_3$): δ 8.71 (s, 1H), 7.68-7.72 (m, 2H), 7.58-7.62 (m, 1H), 6.63 (d, J=3.2 Hz, 1H), 2.44 (br s, 2H), 2.20 (br s, 2H), 2.16 (br s, 2H), 1.84 (br s, 2H), 1.69 (overlapping br s, 6H), 1.21 (s, 9H) ppm. HRMS (m/z): [M+Na]$^+$ calc, for C$_{26}$H$_{28}$INNaO$_6$ 600.0859, found 600.0963.

Example 30. (1r,3r,5r,7r)-Spiro[adamantane-2,2'-[1,3]dioxane]-4',6'-dion-[N-Boc-indol-5-iodonium] ylide

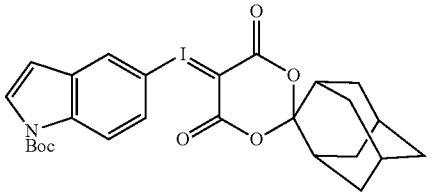 [SMILES: CC(C)(C)OC(=O)n1ccc2cc(I=C3C(=O)OC4(OC3=O)C3CC5CC(C3)CC4C5)ccc21]

The title compound was prepared from N-Boc-5-iodoindole following a similar procedure to that used to prepare the indole iodonium ylides described in Example 28-29.

Colourless solid, 14% yield. $^1$H NMR (300 MHz, CDCl$_3$): δ 8.16 (d, J=8.9 Hz, 1H), 8.12 (d, J=1.8 Hz, 1H), 7.76 (dd, J=1.9, 8.9 Hz, 1H), 7.65 (d, J=3.7 Hz, 1H), 2.37 (br s, 2H), 2.14 (br s, 2H), 2.10 (br s, 2H), 1.84 (br s, 2H), 1.80 (br s, 2H), 1.66 (br s, 4H), 1.64 (s, 9H) ppm. $^{13}$C NMR (75 MHz, CDCl$_3$): δ 165.0, 163.7, 133.2, 132.8, 129.9, 128.9, 128.4, 127.6, 118.6, 107.7, 107.0, 85.3, 56.8, 47.1, 35.6, 33.9, 28.2, 26.7 ppm. HRMS (m/z): [M+Na]$^+$ calc, for C$_{26}$H$_{25}$INNaO$_6$ 600.0859, found 600.0863.

Example 31. Synthesis and Characterization of Drug Fragment Precursors

Iodinium ylide drug precursors were prepared according to the following procedures:

A. Filorexant

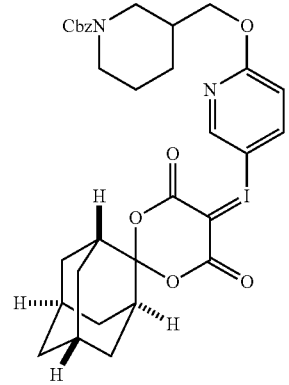 [SMILES: O=C1OC2(OC(=O)C1=Ic1ccc(OCC3CCCN(C(=O)OCc4ccccc4)C3)nc1)[C@H]1C[C@@H]3C[C@@H](C[C@H]2C3)C1]

Step 1. Benzyl 3-(hydroxymethyl)piperidine-1-carboxylate

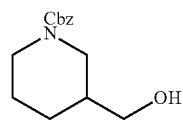

To a solution of piperidin-3-ylmethanol (1.2 g, 10.4 mmol) and 1 N NaOH (14.5 mL, 14.5 mmol) in 1,4-dioxane (14 mL) was added benzylchloroformate (CbzCl) (2.1 mL, 14.5 mmol) dropwise (using dropping funnel) at 0° C. After stirring for 30 min at room temperature, the mixture was diluted with H₂O, acidified with 10% HCl to pH 1 and extracted with ethyl acetate (15 mL×3). The organic layer was washed with brine, dried over MgSO₄, and evaporated. The residue was purified with flash column chromatography (Hexanes/EtOAc=1/1) to afford benzyl 3-(hydroxymethyl)piperidine-1-carboxylate (2.37 g, yield 91%) as a colorless oil.

Step 2. Benzyl 3-((tosyloxy)methyl)piperidine-1-carboxylate

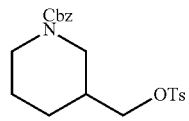

To a solution of benzyl 3-(hydroxymethyl) piperidine-1-carboxylate (2.37 g, 9.5 mmol), dimethylaminopyridine (58 mg, 0.48 mmol) and triethylamine (2.6 ml, 19.0 mmol) in dichloromethane (50 ml) at 0° C. was added p-toluenesulfonyl chloride (2.0 g, 10.5 mmol) and the reaction stirred for 18 hours at room temperature. The mixture was diluted with 100 ml of dichloromethane and washed saturated sodium bicarbonate (15 mL×3), water (20 mL) and brine (50 mL). The organics were dried over sodium sulfate, filtered and concentrated under reduced pressure to afford benzyl 3-((tosyloxy)methyl)piperidine-1-carboxylate (3.7 g, 97%) as a white solid, which was characterized according to a literature procedure (see e.g. Abreu et al., *Tetrahedron*, 2005, 61:11986-11990)

Step 3. Benzyl 3-(((5-iodopyridin-2-yl)oxy)methyl)piperidine-1-carboxylate

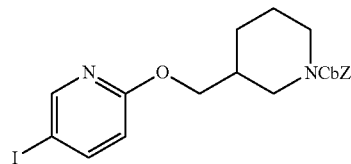

In a 100 mL reaction vessel was charged the solution of benzyl 3-((tosyloxy)methyl)piperidine-1-carboxylate (1.0 g, 2.48 mmol) in NMP (24 mL), 5-iodopyridin-2-ol S1-4 (657 mg, 2.97 mmol), and Cs₂CO₃ (2.2 g, 6.65 mmol). The mixture was heated to 60° C. and stirred for 26 h. It was cooled to 15° C. before addition of water (100 mL) over 5 min, keeping the temperature below 25° C. The solution was extracted with ethyl ether (25 mL×3). The organic layer was washed with 10 wt % LiCl (20 mL×2) and brine (20 mL×2). The organics were dried over sodium sulfate, filtered and evaporated in vacuo. The residue was purified by column chromatography on silica gel (Hexanes/EtOAc=3/1) to afford benzyl 3-(((5-iodopyridin-2-yl)oxy)methyl)piperidine-1-carboxylate (1.04 g, 2.3 mmol) as colorless oil. ¹H NMR (300 MHz, CDCl₃) δ 8.30-8.29 (m, 1H), 7.76 (dd, J=8.8, 2.4 Hz, 1H), 7.34-7.26 (m, 5H), 6.55 (d, J=8.2 Hz), 5.12 (s, 2H), 4.19-4.11 (m, 2H), 4.08-3.98 (m, 2H), 2.91 (br s, 1H), 2.71 (br s, 1H), 2.04-2.01 (m, 1H), 1.91-1.85 (m, 1H), 1.73-1.67 (m, 1H), 1.57-1.49 (m, 1H), 1.33-1.21 (m, 1H); ¹³C NMR (75 MHz, CDCl₃) δ 163.0, 155.3, 152.5, 146.3, 136.9, 128.4, 127.8, 127.7, 113.5, 82.1, 68.0, 66.9, 47.2, 44.6, 35.6, 27.2; HRMS (m/z): [M+Na]⁺ calc. for C₁₉H₂₁IN₂NaO₃ 475.0495, found 475.0496.

Step 4. Filrexant Precursor

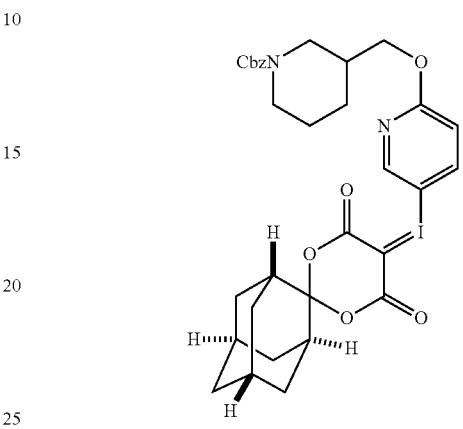

In a N₂ charged round-bottom flask, benzyl 3-(((5-iodopyridin-2-yl)oxy)methyl)piperidine-1-carboxylate (200 mg, 0.44 mmol) was dissolved in dry MeCN (2 mL). Trimethylsilyl acetate (175 mg, 1.33 mmol) and a solution of Selectfluor® (313 mg, 0.89 mmol) in dry MeCN (2 mL) were added dropwise sequentially. The reaction mixture was stirred at room temperature for 15 h. MeCN was removed by evaporation and the remaining yellow oil was treated with H₂O (10 mL). The mixture was extracted with dichloromethane (5 mL×3). The organic layers were combined, washed with aqueous acetate buffer (NaOAc:HOAc=0.5 M:0.5 M, pH=5, 5 mL×3), dried over Na₂SO₄, filtered and evaporated under reduced pressure. Pentane (10 mL) and dichloromethane (1.0 mL) were added to the oil and mixture was placed in an ultrasonic bath and sonicated until the compound solidified. The solvent was decanted away and the remaining solid was dried under vacuum for 4 h. The obtained diacetoxyiodoarene (220 mg, ~0.39 mmol) was used in the next step.

A solution of diacetoxyiodoarene (220 mg, ~0.39 mmol) in EtOH (6 mL) was added a solution of SPI-Adaman (91 mg, 0.39 mmol) in 10% Na₂CO₃ (3.0 mL), followed by addition of 10% Na₂CO₃ (3.0 mL) to adjust pH value of the mixture to be around 10. The reaction was stirred at ambient temperature for 4 h, then diluted with H₂O (15 mL), extracted with DCM (10 mL×3). The combined organic extracts were dried with anhydrous MgSO₄, filtered and concentrated. To the residue was added ethyl acetate and pentane to induce precipitation and stored at −25° C. in freezer overnight. After decantation, the filrexant precursor was obtained as white solid (239 mg, yield over two steps 78%).

¹H NMR (300 MHz, CD₂Cl₂) δ 8.61 (d, J=2.2 Hz, 1H), 8.10 (dd, J=9.0, 2.2 Hz, 1H), 7.35 (s, 5H), 6.82 (br s, 1H), 5.35 (s, 2H), 4.35-4.05 (m, 3H), 3.95 (br s, 1H), 2.95 (t, J=11.3 Hz, 1H), 2.76 (br s, 1H), 2.37 (s, 2H), 2.07 (d, J=12.4 Hz, 6H), 1.82 (br s, 3H), 1.71 (d, J=11.4 Hz, 6H), 1.58-1.44 (m, 1H), 1.42-1.25 (m, 1H) ¹³C NMR (75 MHz, CD₂Cl₂) δ 165.4, 163.0, 155.1, 151.8, 143.7, 137.2, 128.4, 127.8, 127.5, 115.1, 107.0, 103.3, 68.9, 66.7, 56.3, 46.9, 44.4, 37.0, 35.5, 35.4, 33.7, 27.0, 26.6, HRMS (m/z): [M+Na]+ calc. for C$_{32}$H$_3$IN$_2$NaO$_7$ 709.1387, found 709.1389.

B. Mosapride

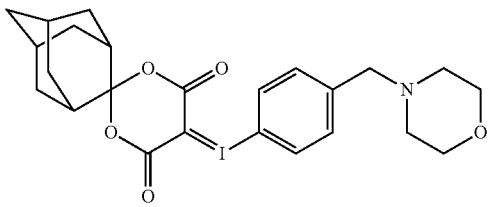 [SMILES: O=C1OC2(OC(=O)C1=Ic1ccc(CN3CCOCC3)cc1)C1CC3CC(C1)CC2C3]

A solution of N-(para-iodobenzyl)morpholine (106 mg, 0.35 mmol; prepared by reductive amination of 4-iodobenzaldehyde) in chloroform (350 µL) was treated with trifluoroacetic acid (1.1 mL, 14 mmol) followed by oxone monopersulfate (172 mg, 0.56 mmol). The heterogeneous mixture was stirred at room temperature for 4 h and then concentrated under reduced pressure. The residue was suspended in ethanol (1.4 mL) and treated with the adamantyl substituted auxiliary acid (SPIAd, 83 mg, 0.35 mmol) and a solution of 10% sodium carbonate in water, which was used to adjust the pH to ~10 (~5 mL). The reaction was stirred at room temperature for 3 h and then diluted with water and extracted with dichloromethane three times. The combined organic layers were dried with anhydrous sodium sulfate, filtered and concentrated. The product was purified by flash chromatography on silica (mobile phase gradient: 50→100% ethyl acetate/hexanes, then 0→20% methanol/ethyl acetate) to yield the mosapride precursor as a white solid (0.15 mmol, 44%). $^1$H NMR (300 MHz, CDCl$_3$) δ 7.80 (d, J=8.4 Hz, 2H), 7.40 (d, J=8.4 Hz, 2H), 3.69 (m, 4H), 3.50 (s, 2H), 2.41 (m, 6H), 2.16 (br s, 2H), 2.12 (br s, 2H), 1.84 (br s, 2H), 1.70 (br s, 4H), 1.66 (br s, 2H) ppm. $^{13}$C NMR (75 MHz, CDCl$_3$) δ 163.5, 137.6, 133.6, 132.5, 107.7, 67.0, 62.5, 56.0, 53.7, 39.4, 37.3, 35.7, 33.9, 33.6, 26.7 ppm. [M+Na]+ calc. for C$_{24}$H$_{28}$INNaO$_5$ 560.0910, found 560.0908. The $^{19}$F-standard compound was prepared by reductive amination according to the procedures described in Bhattacharyya et al., *Synth. Commun.* 1997, 27:4265-4274.

C. Lapatinib

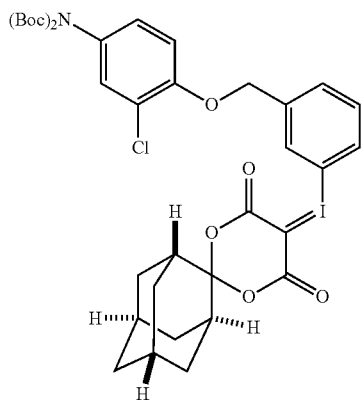

Step 1, tert-Butyl (3-chloro-4-hydroxyphenyl)carbamate

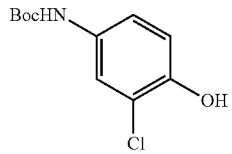 [SMILES: CC(C)(C)OC(=O)Nc1ccc(O)c(Cl)c1]

A well-stirred solution of 4-amino-2-chlorophenol (2.0 g, 14.0 mmol) in H$_2$O (16 mL) was treated with t-Boc$_2$O (3.36 g, 15.4 mmol). The mixture was stirred at room temperature for 22 h and then extracted with ethyl acetate (30 mL t 3), washed with brine, dried over sodium sulfate, filtered and evaporated in vacuo. The residue was purified by column chromatography on silica gel (Hexanes/EtOAc=5/1) to afford tert-butyl (3-chloro-4-hydroxyphenyl)carbamate (3.3 g, yield 97%) as white solid. The sub-title product was characterized according to literature procedures as described in Roosen et al., *J. Am. Chem. Soc.* 2012, 134:11350-11353.

Step. 2, tert-Butyl (3-chloro-4-((3-iodobenzyl)oxy)phenyl)carbamate

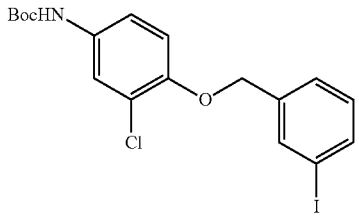

A solution of the tert-butyl (3-chloro-4-hydroxyphenyl)carbamate (347.2 mg, 1.43 mmol) in anhydrous DMF (5 mL) was added K$_2$CO$_3$ (984 mg, 7.12 mmol) and 1-(bromomethyl)-3-iodobenzene (444 mg, 1.5 mmol). The resulting solution was then stirred at 100° C. for 3 h under Ar. The reaction mixture was cooled to ambient temperature and quenched with water (50 mL), and then extracted with ethyl ether (15 mL×3). The organic layers were combined, washed with brine, dried over Na$_2$SO$_4$, filtered, and evaporated under reduced pressure. The crude product was purified by flash chromatography (Hexanes/EtOAc=5/1) to afford tert-butyl (3-chloro-4-((3-iodobenzyl)oxy)phenyl)carbamate (644 mg, yield 98%) as white solid. $^1$H NMR (300 MHz, CDCl$_3$) δ 7.80 (s, 1H), 7.64 (d, J=7.8 Hz, 1H), 7.49 (d, J=2.6 Hz, 1H), 7.41 (d, J=7.8 Hz, 1H), 7.14-7.07 (m, 2H), 6.83 (d, J=8.9 Hz, 1H), 6.41 (br s, 1H), 5.02 (s, 2H), 1.51 (s, 9H); $^{13}$C NMR (75 MHz, CDCl$_3$) δ 152.8, 149.8, 138.9, 137.0, 136.0, 132.8, 130.3, 126.3, 123.8, 121.2, 118.1, 114.9, 94.4, 80.8, 70.5, 28.3; HRMS (m/z): [M+Na]+ calc. for C$_{18}$H$_{19}$ClINNaO$_3$ 481.9996, found 481.9998.

Step 3. N,N-(Bis(tert-butyloxycarbonyl))-3-chloro-4-(3-iodophenylmethoxy)aniline

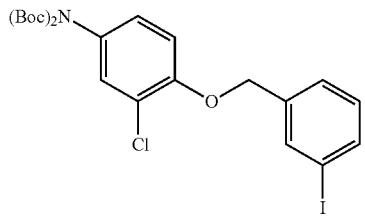

A solution of the tert-butyl (3-chloro-4-((3-iodobenzyl)oxy)phenyl)carbamate (667 mg, 1.45 mmol) in anhydrous THF (5 mL) was added Et$_3$N (0.6 mL, 4.35 mmol), DMAP (88 mg, 0.73 mmol) and t-Boc$_2$O (633 mg, 2.9 mmol). The resulting solution was stirred at ambient temperature for 15 h under Ar. The reaction was quenched with water (50 mL), and then extracted with ethyl acetate (15 mL×3). The organic layers were combined, washed with brine, dried over Na$_2$SO$_4$, filtered, and evaporated under reduced pressure. The crude product was purified by flash chromatography (Hexanes/EtOAc=5/1) to afford the desired product (666 mg, yield 82%) as a white solid. $^1$H NMR (300 MHz, CDCl$_3$) δ 7.81 (s, 1H), 7.65 (d, J=8.4 Hz, 1H), 7.42 (d, J=7.9 Hz, 1H), 7.21 (d, J=2.6 Hz, 1H), 7.12 (t, J=7.7 Hz, 1H), 6.99 (dd, J=8.8, 2.6 Hz, 1H), 6.88 (d, J=8.8 Hz, 1H), 5.09 (s, 2H), 1.43 (s, 18H); $^{13}$C NMR (75 MHz. CDCl$_3$) δ 153.1, 151.7, 138.6, 137.1, 135.9, 133.0, 130.3, 130.1, 127.3, 126.2, 122.9, 133.5, 94.4, 83.0, 70.0, 27.9; HRMS (m/z): [M+Na]$^+$ calc, for C$_{23}$H$_{27}$ClINNaO$_5$ 582.0520, found 582.0521.

Step 4. Lapatinib Precursor

In a N$_2$ charged round-bottom flask, the product of Step 3 (200 mg, 0.36 mmol) was dissolved in dry MeCN (2 mL). Trimethylsilyl acetate (141 mg, 1.1 mmol) and a solution of Selectfluor® (316 mg, 0.89 mmol) in dry MeCN (2 mL) were added dropwise, sequentially. The reaction mixture was allowed to stir at room temperature for 15 h. MeCN was removed by evaporation and the remaining yellow oil was treated with H$_2$O (10 mL). The mixture was extracted with dichloromethane (5 mL×3). The organic layers were combined, washed with aqueous acetate buffer (NaOAc:HOAc=0.5 M:0.5 M, pH=5, 5 mL×3), dried over Na$_2$SO$_4$, filtered, and evaporated under reduced pressure. Pentane (15 mL) and dichloromethane (1.5 mL) were added to the oil and mixture was placed in an ultrasonic bath and sonicated until the compound solidified. The solvent was decanted away and the remaining solid was dried under vacuum for 4 h. The obtained diacetoxyiodoarene (214 mg, ~0.32 mmol) was used in the next step.

A solution of diacetoxyiodoarene (214 mg, ~0.32 mmol) in EtOH (5 mL) was added a solution of SPI-Adaman (75 mg, 0.32 mmol) in 10% Na$_2$CO$_3$ (2.5 mL), followed by addition of 10% Na$_2$CO$_3$ (2.5 mL) to adjust pH value of the mixture to be around 10. The reaction was stirred at ambient temperature for 4 h, then diluted with H$_2$O (15 mL), extracted with DCM (10 mL×3). The combined organic extracts were dried with anhydrous MgSO$_4$, filtered and concentrated. To the residue was added ethyl acetate and pentane to induce precipitation and stored at −25° C. in freezer overnight. After decantation, the lapatinib precursor (209 mg, yield over two steps 74%) was obtained as a white solid.

$^1$H NMR (300 MHz, CD$_2$Cl$_2$) δ 7.94 (s, 1H), 7.76 (d, J=8.2 Hz, 1H), 7.66 (d, J=7.7 Hz, 1H), 7.44 (t, J=8.2 Hz, 1H), 7.21 (d, J=2.4 Hz, 1H), 7.02 (dd, J=8.7, 2.3 Hz, 1H), 6.95 (d, J=8.7 Hz, 1H), 5.13 (s, 2H), 2.40 (s, 2H), 2.07 (d, J=12.4 Hz, 4H), 1.82 (s, 2H), 1.69 (d, J=11.4 Hz, 6H), 1.41 (s, 18H); $^{13}$C NMR (75 MHz, d$_6$-DMSO) δ 163.0, 152.8, 151.7, 140.0, 133.0, 132.3, 131.4, 131.1, 130.0, 128.3, 121.5, 116.7, 114.3, 105.5, 82.8, 69.7, 57.9, 36.9, 35.2, 33.6, 27.9, 26.4; HRMS (m/z): [M+Na]$^+$ calc, for C$_{36}$H$_{41}$ClINNaO$_9$ 816.1412, found 816.1417.

D. Risperidone

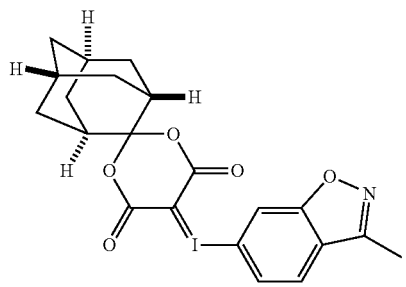 [SMILES: Cc1noc2cc(I=C3C(=O)OC4(OC3=O)[C@H]3C[C@@H]5C[C@@H](C[C@H]4C5)C3)ccc12]

Step 1, 5-Bromo-2-(1-iminoethyl)phenol

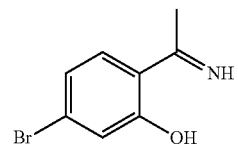

1-(4-bromo-2-hydroxyphenyl) ethan-1-one (1.02 g, 4.7 mmol) in 7 M ammonia in MeOH (3.5 ml, 23.6 mmol) was stirred at ambient temperature for 2 h to give a yellow slurry. The slurry was filtered and the cake was dried to afford 5-bromo-2-(1-iminoethyl)phenol (1.0 g, yield 99%) as bright yellow solid, which was used in the next step without further purification.

Step 2. 6-Bromo-3-methylbenzo[d]isoxazole

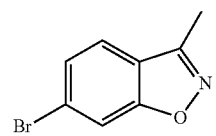

A mixture of 5-bromo-2-(1-iminoethyl)phenol (1.0 g, 4.67 mmol), NCS (935 mg, 7 mmol) and K$_2$CO$_3$ (1.29 g, 9.34 mmol) in THF (15 mL) was stirred at ambient temperature for 12 h. Ethyl acetate (20 mL) and water (15 mL) were added to the reaction mixture and the organic layer was separated, dried over MgSO$_4$, and concentrated in vacuo. The crude product was purified by flash chromatography (Hexanes/EtOAc=5/1) to afford 6-bromo-3-methylbenzo[d]isoxazole (570 mg, yield 58%) as yellow oil. The sub-title product was characterized according to literature procedures as described in Crawford et al., *J. Med. Chem.* 2012, 55:8827-8837.

Step 3, 6-Iodo-3-methylbenzo[d]isoxazole

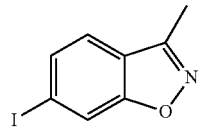

A solution of 6-bromo-3-methylbenzo[d]isoxazole (300 mg, 1.42 mmol), hexabutylditin (1.64 g, 2.83 mmol) and Pd(PPh$_3$)$_4$ (164 mg, 0.15 mmol) in toluene (7 ml) was refluxed for 2 days. The solvent was evaporated and the residue purified by column chromatography (Hexanes/EtOAc=10/1) to give 3-methyl-6-(tributylstannyl)benzo[d]isoxazole as a yellow oil (270 mg), which was dissolved in CH$_3$CN (6 mL). The round-bottomed flask was shielded with tin foil papers. To this mixture was added iodine (324 mg, 1.26 mmol). The mixture was stirred at ambient temperature for 3 hours, then quenched with saturated Na$_2$S$_2$O$_3$ (5 mL), water (5 mL), and extracted with ethyl acetate (10 mL×3). The organic layers were combined, washed with brine, dried over Na$_2$SO$_4$, filtered and evaporated under reduced pressure. The crude product was purified by flash chromatography (Hexanes/EtOAc=6/1) to afford 6-iodo-3-methylbenzo[d]isoxazole (160 mg, yield over two steps 43%) as yellow oil. $^1$H NMR (300 MHz, CDCl$_3$) δ 7.95-7.94 (m, 1H), 7.60 (dd. J=8.3, 1.3 Hz, 1H), 7.35 (dd, J=8.3, 0.6 Hz, 1H), 2.56 (s, 3H); $^{13}$C NMR (75 MHz, CDCl$_3$) δ 163.3, 155.0, 132.4, 126.9, 122.2, 119.3, 95.7, 9.9; HRMS (m/z): [M+Na]$^+$ calc, for C$_8$H$_6$INNaO 281.9392, found 281.9395.

Step 4. Risperidone Precursor

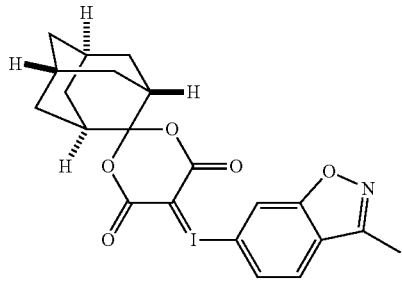 [SMILES: Cc1noc2cc(I=C3C(=O)OC4(OC3=O)[C@H]3C[C@@H]5C[C@@H](C[C@H]4C5)C3)ccc12]

In a N$_2$ charged round-bottom flask, 6-iodo-3-methylbenzo[d]isoxazole (200 mg, 0.77 mmol) was dissolved in dry MeCN (5 mL). Trimethylsilyl acetate (307 mg, 2.32 mmol) and Selectfluor® (545 mg, 1.54 mmol) were added sequentially. The reaction mixture was stirred at room temperature for 15 h. MeCN was removed by evaporation and the remaining yellow oil was treated with H$_2$O (10 mL). The mixture was extracted with dichloromethane (5 mL×3). The organic layers were combined, washed with aqueous acetate buffer (NaOAc:HOAc=0.5 M:0.5 M, pH=5, 5 mL×3), dried over Na$_2$SO$_4$, filtered, and evaporated under reduced pressure. Pentane (10 mL) and dichloromethane (1.0 mL) were added to the oil and mixture was placed in an ultrasonic bath and sonicated until the compound solidified. The solvent was decanted away and the remaining solid was dried under vacuum for 4 h. The obtained diacetoxyiodoarene (97 mg, ~0.26 mmol) was used in the next step.

A solution of the diacetoxyiodoarene (97 mg, ~0.26 mmol) in EtOH (2 mL) was added a solution of SPI-Adaman (42 mg, 0.18 mmol) in 10% Na$_2$CO$_3$ (1.0 mL), followed by addition of 10% Na$_2$CO$_3$ (1.5 mL) to adjust pH value of the mixture to be around 10. The reaction mixture was stirred at ambient temperature for 4 h, then diluted with H$_2$O (15 mL), extracted with DCM (10 mL×3). The combined organic extracts were dried with anhydrous MgSO$_4$, filtered and concentrated. To the residue was added ethyl acetate and pentane to induce precipitation and stored at −25° C. in freezer overnight. After decantation, the risperidone precursor (74 mg, yield over two steps 19%) was obtained as a white solid.
$^1$H NMR (300 MHz, DMSO) δ 8.14 (s, 1H), 7.93 (d, J=8.6 Hz, 1H), 7.68 (d, J=8.2 Hz, 1H), 2.53 (s, 3H), 2.31 (s, 2H), 1.90 (d, J=13.1 Hz, 4H), 1.76 (s, 2H), 1.61 (d, J=10.8 Hz, 6H); $^{13}$C NMR (75 MHz, d$_6$-DMSO) δ 163.0, 162.1, 156.1, 126.9, 124.9, 124.1, 118.3, 114.4, 105.7, 58.7, 36.9, 35.3, 33.6, 26.4, 10.0. HRMS (m/z): [M+Na]$^+$ calc, for C$_{21}$H$_{20}$INNaO$_5$ 516.0248, found 516.0289.

E. Ezetimibe

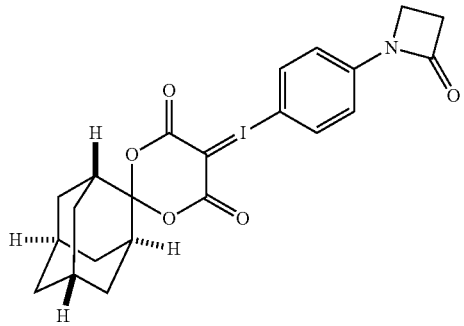 [SMILES: O=C1OC2(OC(=O)C1=Ic1ccc(N3CCC3=O)cc1)[C@H]1C[C@@H]3C[C@@H](C[C@H]2C3)C1]

Step 1, 3-Bromo-N-(4-iodophenyl)propanamide

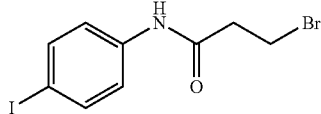 [SMILES: O=C(CCBr)Nc1ccc(I)cc1]

A mixture of 3-bromopropionyl chloride (0.46 mL, 4.57 mmol) in dichloromethane (5 mL) was added dropwise to a mixture of 4-iodoaniline (1.0 g, 4.57 mmol) and K$_2$CO$_3$ (1.6 g, 11.4 mmol) in dichloromethane (15 mL) and the reaction was stirred for 18 hours. The mixture was slowly quenched with water (50 mL). The organic layer was separated and washed twice with water, dried with MgSO$_4$, filtered and evaporated under reduced pressure. The crude product was purified by flash chromatography (Hexanes/EtOAc=3/1) to afford 3-bromo-N-(4-iodophenyl) propanamide (1.54 g, yield 95%) as white solid. $^1$H NMR (300 MHz, d$_6$-DMSO) δ 10.14 (s, 1H), 7.63 (d, J=8.7 Hz, 2H), 7.42 (d, J=8.7 Hz, 2H), 3.71 (t, J=6.3 Hz, 2H), 2.93 (t, J=6.5 Hz, 2H); $^{13}$C NMR (75 MHz, d$_6$-DMSO) δ 168.8, 139.2, 137.8, 121.7, 87.2, 39.5, 29.5; HRMS (m/z): [M+Na]$^+$ calc, for C$_9$H$_9$BrINNaO 375.8810, found 375.8814.

Step 2, 1-(4-Iodophenyl)azetidin-2-one

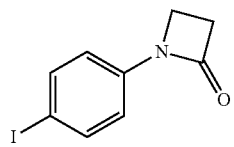 [SMILES: O=C1CCN1c1ccc(I)cc1]

To a solution of 3-bromo-N-(4-iodophenyl) propanamide (1.0 g, 2.82 mmol) in DCM (7.0 mL) was added KOH (174 mg, 3.1 mmol) and 18-crown-6 (820 mg, 3.1 mmol). The reaction mixture was stirred at 40° C. overnight, then quenched with NH$_4$Cl (aq., 20 mL) and extracted with ethyl acetate (30 mL×3). The organic layers were combined, washed with brine, dried over Na$_2$SO$_4$, filtered and evaporated under reduced pressure. The crude product was purified by flash chromatography (Hexanes/EtOAc=1/1, then EtOAc/MeOH=50:1) to afford 1-(4-iodophenyl)azetidin-2-one (352 mg, yield 46%) as a white solid. $^1$H NMR (300 MHz, d$_6$-DMSO) δ 7.66 (d, J=8.7 Hz, 2H), 7.15 (d, J=8.7 Hz, 2H), 3.58 (t, J=4.4 Hz, 2H), 3.05 (t, J=4.5 Hz, 2H); $^{13}$C NMR (75 MHz, d$_6$-DMSO) δ 165.2, 138.6, 138.2, 118.5, 87.1, 38.4, 36.5; HRMS (m/z): [M+Na]$^+$ calc, for C$_9$H$_8$INNaO 295.9548, found 295.9549.

Step 3. Ezetimibe Precursor

In a N$_2$ charged round-bottom flask, 1-(4-iodophenyl) azetidin-2-one (201 mg, 0.74 mmol) was dissolved in dry MeCN (4 mL). Trimethylsilyl acetate (292 mg, 2.21 mmol) and a solution of Selectfluor® (652 mg, 1.84 mmol) in dry MeCN (6 mL) were added dropwise, sequentially. The reaction mixture was allowed to stir at room temperature for 18 h. MeCN was removed by evaporation and the remaining yellow oil was treated with H$_2$O (10 mL). The mixture was extracted with dichloromethane (5 mL×3). The organic layers were combined, washed with aqueous acetate buffer (NaOAc:HOAc=0.5 M:0.5 M, pH=5, 5 mL×3), dried over Na$_2$SO$_4$, filtered and evaporated under reduced pressure. Pentane (15 mL) and dichloromethane (1.5 mL) were added to the oil and mixture was placed in an ultrasonic bath and sonicated until the compound solidified. The solvent was decanted away and the remaining solid was dried under vacuum for 4 h. The obtained diacetoxyiodoarene (260 mg, ~0.66 mmol) was used in the next step.

A solution of the diacetoxyiodoarene (260 mg, ~0.66 mmol) in EtOH (5 mL) was added a solution of SPI-Adaman (157 mg, 0.66 mmol) in 10% Na$_2$CO$_3$ (5 mL), followed by addition of 10%/Na$_2$CO$_3$ (3 mL) to adjust pH value of the mixture to be around 10. The reaction was stirred at ambient temperature for 5 h, then diluted with H$_2$O (30 mL), extracted with DCM (10 mL×3). The combined organic extracts were dried with anhydrous MgSO$_4$, filtered and concentrated. To the residue was added ethyl acetate and pentane (v/v=1/1, 7 mL) to induce precipitation and stored at −25° C. for 1 h. After decantation, the crude compound was dispersed in a vial (25 mL) with ethyl acetate and pentane (v/v=1/1, 7 mL). The mixture was stirred for 5 min and allowed the solid to settle. The supernatant was decanted and this process was repeated for ten more times. After decantation and evaporation of the solvent to dryness using a vacuum pump, the ezetimibe precursor (153 mg, yield over two steps 41%) was obtained as white solid.

$^1$H NMR (300 MHz, CD$_2$Cl$_2$) δ 7.82 (d, J=8.8 Hz, 2H), 7.35 (d, J=8.8 Hz, 2H), 3.65 (t, J=4.7 Hz, 2H), 3.15 (t, J=4.7 Hz, 2H), 2.37 (s, 2H), 2.07 (d, J=12.3 Hz, 4H), 1.83 (s, 2H), 1.70 (d, J=12.5 Hz, 6H); $^{13}$C NMR (75 MHz, CD$_2$Cl$_2$) δ 164.8, 163.0, 141.5, 134.7, 118.7, 106.9, 106.1, 56.3, 38.4, 37.0, 36.7, 35.6, 33.7, 26.6; HRMS (m/z): [M+Na]$^+$ calc, for C$_{22}$H$_{22}$INNaO$_5$ 530.0440, found 530.0443.

F. Astemizole

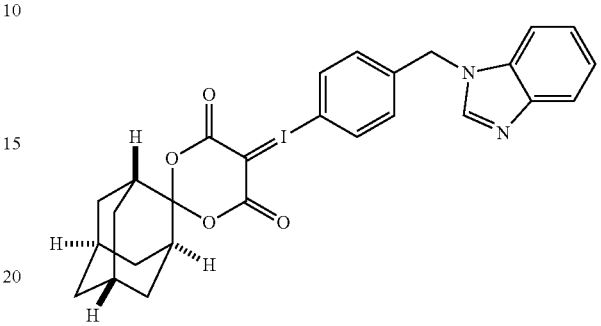

Step 1, 1-(4-Iodobenzyl)-1H-benzo[d]imidazole

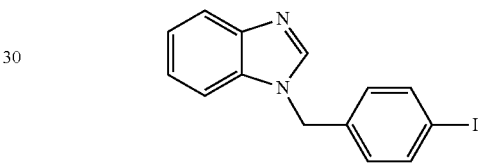

NaH (washed with hexanes for five times to remove mineral oil and dried in vacuo for 3 h, 55 mg, 2.3 mmol)) was added in portions to a solution of benzimidazole (180 mg, 1.53 mmol) in dry THF under argon atmosphere at 0° C. The solution was stirred at ambient temperature for 3 h. At 0° C. 1-(bromomethyl)-4-iodobenzene (500 mg, 1.68 mmol) was added carefully and the reaction mixture was heated at 60° C. for 15 h. The reaction was quenched with H$_2$O (15 mL) and extracted with EtOAc (15 mL×3). The combined organic phases were dried over MgSO$_4$, filtered, and evaporated. The crude product was purified by flash chromatography (Hexanes/EtOAc=1/1 to 0/1, then EtOAc/ MeOH=50:1) to afford 1-(4-iodobenzyl)-1H-benzo[d]imidazole (301 mg, yield 59%) as white solid. $^1$H NMR (300 MHz, CDCl$_3$) δ 8.05 (s, 1H), 7.84 (d, J=7.4 Hz, 1H), 7.66 (d, J=8.3 Hz, 2H), 7.31-7.24 (m, 3H), 6.92 (d, J=8.3 Hz, 2H), 5.32 (s, 2H); $^{13}$C NMR (75 MHz, CDCl$_3$) δ 143.7, 143.0, 138.2, 135.0, 133.6, 128.9, 123.4, 122.6, 120.4, 110.0, 93.8, 48.4, HRMS (m/z): [M+Na]$^+$ calc, for C$_{14}$H$_{11}$IN$_2$Na 356.9865, found 356.9867.

Step 2. Astemizole Precursor

In a N$_2$ charged round-bottom flask, 1-(4-iodobenzyl)-1H-benzo[d]imidazole (200 mg, 0.6 mmol) was dissolved in dry MeCN (2 mL). Trimethylsilyl acetate (238 mg, 1.8 mmol) and a solution of Selectfluor® (531 mg, 1.5 mmol) in dry MeCN (5 mL) were dropwisely added sequentially. The reaction mixture was stirred at room temperature for 18 h. MeCN was removed by evaporation and the remaining yellow oil was treated with H$_2$O (10 mL). The mixture was extracted with dichloromethane (10 mL×3). The organic layers were combined, washed with aqueous acetate buffer (NaOAc:HOAc=0.5 M:0.5 M, pH=5, 5 mL×3), dried over Na$_2$SO$_4$, filtered and evaporated under reduced pressure. Pentane (10 mL) and dichloromethane (1.0 mL) were added to the oil and mixture was placed in an ultrasonic bath and sonicated until the compound solidified. The mixture was stored at −20° C. in freezer for 1 h, and the solvent was decanted away. This process was repeated once more. The remaining solid was dried under vacuum for 2 h. The obtained diacetoxyiodoarene (200 mg, ~0.44 mmol) was used in the next step.

A solution of the diacetoxyiodoarene (200 mg, ~0.44 mmol) in EtOH (4 mL) was added a solution of SPI-Adaman (105 mg, 0.44 mmol) in 10% Na$_2$CO$_3$ (3.5 mL), followed by addition of 10% Na$_2$CO$_3$ (3.5 mL) to adjust pH value of the mixture to be around 10. The reaction was stirred at ambient temperature for 3 h, then diluted with H$_2$O (25 mL), extracted with DCM (20 mL×3). The combined organic extracts were dried with anhydrous MgSO$_4$, filtered and concentrated. To resulting solid was added ethyl acetate (6 mL), sonicated, allowed to settle and decanted. This process was repeated for three more times. After evaporation of the solvent to dryness using a vacuum pump, the astemizole precursor (189 mg, yield over two steps 55%) was obtained as white solid.

$^1$H NMR (300 MHz, d$_6$-DMSO) δ 8.38 (s, 1H), 7.71 (d, J=8.3 Hz, 2H), 7.66-7.63 (m, 1H), 7.47-7.43 (m, 1H), 7.32 (d, J=8.3 Hz, 2H), 7.20-7.16 (m, 2H), 5.54 (s, 2H), 2.28 (s, 2H), 1.90 (d, J=11.8 Hz, 4H), 1.76 (s, 2H), 1.60 (d, J=13.5 Hz, 6H); $^{13}$C NMR (75 MHz, d$_6$-DMSO) δ 163.0, 144.7, 144.0, 140.3, 133.9, 133.2, 130.2, 123.0, 122.1, 120.0, 115.5, 111.0, 105.5, 58.0, 47.4, 36.9, 35.2, 33.6, 26.4; HRMS (m/z): [M+Na]$^+$ calc, for C$_{27}$H$_{25}$IN$_2$NaO$_4$ 591.0757, found 591.0759.

G. Paroxetine

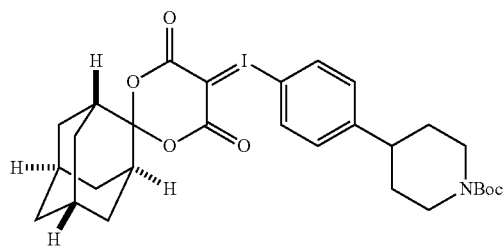 [SMILES: CC(C)(C)OC(=O)N1CCC(c2ccc(I=C3C(=O)OC4(OC3=O)[C@H]3C[C@@H]5C[C@@H](C[C@H]4C5)C3)cc2)CC1]

Step 1, tert-Butyl 4-(4-bromophenyl)piperidine-1-carboxylate

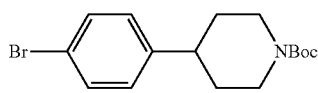 [SMILES: CC(C)(C)OC(=O)N1CCC(c2ccc(Br)cc2)CC1]

A well-stirred solution of 4-(4-bromophenyl) piperidine (460 mg, 1.92 mmol) in DCM (5 mL) was treated with triethylamine (583 mg, 5.76 mmol), followed by addition of t-Boc$_2$O (503 mg, 2.3 mmol) at 0° C. The mixture was stirred at room temperature for 20 h and then quenched with H$_2$O (10 mL), extracted with dichloromethane (10 mL×3), washed with brine, dried over sodium sulfate, filtered and evaporated in vacuo. The residue was purified by column chromatography on silica gel (Hexanes/EtOAc=12/1) to afford tert-butyl 4-(4-bromophenyl)piperidine-1-carboxylate (582 mg, yield 89%) as colorless oil. The sub-title compound was confirmed by comparison with published characterization data (see e.g., Allwood et al., *J. Org. Chem.* 2014, 79:328-338).

Step 2, tert-Butyl 4-(4-iodophenyl)piperidine-1-carboxylate

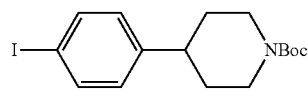 [SMILES: CC(C)(C)OC(=O)N1CCC(c2ccc(I)cc2)CC1]

n-Butyllithium (2.5 M solution, 0.6 mL, 1.49 mmol) was added at −78° C. under stirring to the solution of tert-butyl 4-(4-bromophenyl)piperidine-1-carboxylate (460 mg, 1.35 mmol) in THF (4 mL) under argon. The mixture was stirred at −78° C. for 30 minutes and then the solution of iodine (412 mg, 1.62 mmol) in THF (2.5 mL) was added. After stirring at −78° C. for 2 hours the mixture was warmed to room temperature, diluted with water (10 mL), and extracted with ethyl acetate (10 mL×3). The organic layers were combined, washed with water (20 mL×1), saturated Na$_2$S$_2$O$_3$ solution (10 mL×3), brine (10 mL×2), and dried with Na$_2$SO$_4$. The solvent was removed in vacuo and the residue was purified by column chromatography on silica gel (Hexanes/EtOAc=12/1) to afford tert-butyl 4-(4-iodophenyl)piperidine-1-carboxylate S7-3 (410 mg, yield 78%) as colorless oil. The sub-title compound was confirmed by comparison with published characterization data (see e.g., Allwood et al., *J. Org. Chem.* 2014, 79:328-338).

Step 3. Paroxetine Precursor

In a N$_2$ charged round-bottom flask, tert-butyl 4-(4-iodophenyl)piperidine-1-carboxylate (410 mg, 1.06 mmol) was dissolved in dry MeCN (10 mL). Trimethylsilyl acetate (420 mg, 3.18 mmol) and Selectfluor® (938 mg, 2.65 mmol) were added sequentially. The reaction mixture was allowed to stir at room temperature for 15 h. MeCN was removed by evaporation and the remaining yellow oil was treated with H$_2$O (20 mL). The mixture was extracted with dichloromethane (15 mL×3). The organic layers were combined, washed with aqueous acetate buffer (NaOAc:HOAc=0.5 M:0.5 M, pH=5, 10 mL×3), dried over Na$_2$SO$_4$, filtered and evaporated under reduced pressure. Pentane (15 mL) and dichloromethane (1.5 mL) were added to the oil and mixture was placed in an ultrasonic bath and sonicated until the compound solidified. The mixture was stored at −20° C. in freezer for 1 h, and the solvent was decanted away. This process was repeated once more. The remaining solid was dried under vacuum for 2 h. The obtained diacetoxyiodoarene (405 mg, ~0.80 mmol) was used in the next step.

A solution of the diacetoxyiodoarene (405 mg, ~0.80 mmol) in EtOH (6 mL) was added to a solution of SPI-Adaman (190 mg, 0.80 mmol) in 10% Na$_2$CO$_3$ (6.5 mL), followed by addition of 10% Na$_2$CO$_3$ (2.0 mL) to adjust pH value of the mixture to be around 10. The reaction was stirred at ambient temperature for 3 h, then diluted with H$_2$O (25 mL), extracted with DCM (20 mL×3). The combined organic extracts were dried with anhydrous MgSO$_4$, filtered and concentrated. To resulting solid was added ethyl acetate/pentane (v/v=1/1, 10 mL), sonicated, allowed to settle and decanted. This process was repeated for three more times. After dryness using a vacuum pump, the paroxetine precursor (392 mg, yield over two steps 60%) was obtained as a white solid.

$^1$H NMR (300 MHz, d$_6$-DMSO) δ 7.67 (d, J=8.4 Hz, 2H), 7.33 (d, J=8.4 Hz, 2H), 4.07-4.00 (m, 2H), 2.75-2.66 (m, 3H), 2.32 (br s, 2H), 1.91 (d, J=12.1 Hz, 4H), 1.75 (d, J=13.5 Hz, 3H), 1.66 (t, J=10.5 Hz, 7H), 1.47 (td, J=13.0, 4.5 Hz, 2H), 1.39 (s, 9H); $^{13}$C NMR (75 MHz, d$_6$-DMSO) δ 162.8, 154.1, 149.0, 132.8, 129.8, 113.6, 105.3, 78.9, 57.8, 41.6, 36.8, 35.1, 33.5, 32.7, 28.4, 26.3; HRMS (m/z): [M+Na]$^+$ calc, for C$_{29}$H$_{36}$INNaO$_6$ 644.1485, found 644.1487.

H. Pitavastatin

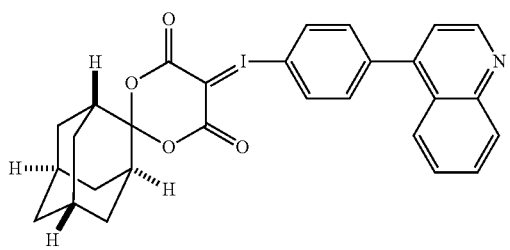 [SMILES: O=C1OC2(OC(=O)C1=Ic1ccc(-c3ccnc4ccccc34)cc1)[C@H]1C[C@@H]3C[C@@H](C[C@H]2C3)C1]

Step 1. Quinolin-4-yl acetate

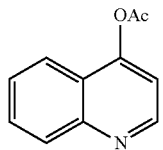 [SMILES: CC(=O)Oc1ccnc2ccccc12]

To an oven-dried flask (25 mL) were charged of 4-quinolinol (500 mg, 3.44 mmol) and DCM (7 mL), and the mixture was subsequently cooled down to 0° C. To the mixture was then added N-ethylmorpholine (475 mg, 4.13 mmol). The mixture was stirred at 0° C. for 10 min, then AcCl (324 mg, 4.13 mmol) was added dropwise. The mixture was stirred at room temperature for 12 h, and quenched with water (10 mL), extracted with dichloromethane (8 mL×3), washed with brine, dried over sodium sulfate, filtered and evaporated in vacuo. The residue was purified by column chromatography on silica gel (Hexanes/EtOAc=3/1) to afford quinolin-4-yl acetate (514 mg, yield 80%) as a white solid. $^1$H NMR (300 MHz, CDCl$_3$) δ 8.91 (d, J=5.0 Hz, 1H), 8.75 (d, J=8.7 Hz, 1H), 7.99-7.95 (m, 1H), 7.79-7.73 (m, 1H), 7.61-7.56 (m, 1H), 7.33 (d, J=4.9 Hz, 1H), 2.49 (s, 3H); $^{13}$C NMR (75 MHz, CDCl$_3$) δ 168.0, 154.1, 150.6, 149.7, 130.2, 129.3, 127.0, 122.2, 121.2, 112.8, 21.1; HRMS (m/z): [M+Na]$^+$ calc, for C$_{11}$H$_9$INNaO$_2$ 210.0531, found 210.0534.

Step 2, 4-(4-Nitrophenyl)quinoline

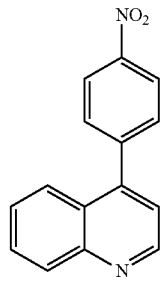 [SMILES: O=[N+]([O-])c1ccc(-c2ccnc3ccccc23)cc1]

To an oven-dried flask (50 mL) under an argon atmosphere were charged of 2-methyl-THF (10 mL), quinolin-4-yl acetate (374 mg, 2 mmol), (4-nitrophenyl)boronic acid (401 mg, 2.4 mol), Pd$_2$(dba)$_3$ (23 mg, 0.04 mmol) and SPhos (33 mg, 0.08 mmol). The mixture was degassed with argon for 15 min, and then agitated at 65° C. for 20 h. To the agitated solution was charged ethyl acetate (20 mL), followed by 5% NaOH (10 mL). The mixture was stirred for 10 min. The aqueous phase was cut. The organic phase was washed with 10% brine (10 mL), dried over sodium sulfate, filtered and evaporated in vacuo.

The residue was purified by column chromatography on silica gel (Hexanes/EtOAc=3/1) to afford crude product, which was recrystallized from EtOAc/Pentane=1/5 at −20° C. overnight. After filtration, the pure compound 4-(4-nitrophenyl)quinoline (210 mg, yield 42%) was obtained as a white solid. $^1$H NMR (300 MHz, CDCl$_3$) δ 9.00 (d, J=4.4 Hz, 1H), 8.39 (d, J=8.5 Hz, 2H), 8.23 (d, J=9.0 Hz, 1H), 7.80-7.75 (m, 2H), 7.69 (d, J=8.6 Hz, 2H), 7.55 (t, J=8.1 Hz, 1H), 7.36 (d, J=4.4 Hz, 1H); $^{13}$C NMR (75 MHz. CDCl$_3$) δ 149.7, 148.4, 147.9, 146.1, 144.5, 130.5, 130.0, 129.9, 127.4, 125.9, 125.0, 123.8, 121.1; HRMS calc'd for C$_{15}$H$_{11}$N$_2$O$_2$ [M+H]$^+$, 251.0821; found 251.0819.

Step 3, 4-(Quinolin-4-yl)aniline

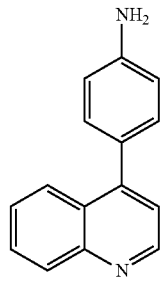 [SMILES: Nc1ccc(-c2ccnc3ccccc23)cc1]

A mixture of 4-(4-nitrophenyl)quinoline (210 mg, 0.84 mmol) and Pd—C (10%, 70 mg) in MeOH (8 mL) was hydrogenated under balloon H$_2$ for 24 h. The mixture was then filtered through celite. The filtrate was concentrated in vacuo to give 4-(quinolin-4-yl)aniline (~210 mg) as a yellow solid, which was used in the next step without further purification.

Step 4, 4-(4-Iodophenyl)quinoline

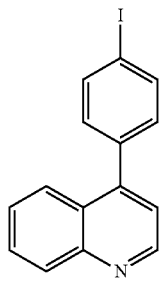

4-(Quinolin-4-yl) aniline (50 mg, 0.23 mmol) was dissolved in 48% aqueous $HBF_4$ (1.0 mL) and cooled to −10° C. To the resulting slurry was added powdered $NaNO_2$ (17.2 mg, 0.25 mmol). After 30 min, NaI (54 mg, 0.36 mmol) was added to the mixture. The reaction was stirred for 30 min, then decolorized by adding saturated $Na_2S_2O_3$ (2 mL), neutralized with saturated aqueous $Na_2CO_3$ (2 mL), and extracted with chloroform (3×5 mL). The organic layer was dried over sodium sulfate, filtered and evaporated in vacuo. The residue was purified by column chromatography on silica gel (Hexanes/EtOAc=3/1) to afford 4-(4-iodophenyl)quinoline (20 mg, yield 27%) as a yellow solid. $^1$H NMR (300 MHz, $CDCl_3$) δ 8.94 (d, J=4.3 Hz, 1H), 8.20 (d, J=8.6 Hz, 1H), 7.87 (dt, J=8.3, 1.8 Hz, 3H), 7.74 (tt, J=8.5, 1.4 Hz, 1H), 7.52 (tt, J=8.4, 1.2 Hz, 1H), 7.30 (d, J=4.5 Hz, 1H), 7.25 (dt, J=8.4, 1.8 Hz, 2H); $^{13}$C NMR (75 MHz, $CDCl_3$) δ 149.7, 148.4, 147.5, 137.8, 137.3, 131.3, 129.7, 129.6, 126.9, 126.3, 125.5, 121.1, 94.6; HRMS (m/z): [M+Na]$^+$ calc. for $C_{15}H_{10}INNa$ 353.9756, found 353.9757.

Step 5. Pitavastatin Precursor

To a solution of 4-(4-iodophenyl)quinoline (20 mg, 0.06 mmol) in a mixture of trifluoroacetic acid (1.2 mL) and chloroform (0.5 mL) was added Oxone (73 mg, 0.12 mmol) under stirring at room temperature. The reaction mixture was stirred at room temperature for 1.5 hours. The solvent was evaporated under vacuum, and the residue was treated with chloroform (2 mL). The insoluble residue of inorganic salts was collected by filtration, washed with chloroform (2 mL), and discarded. Evaporation of combined chloroform extracts under reduced pressure afforded crude products, which was dried under vacuum for 30 min and dissolved in EtOH (0.5 mL). The mixture was added a solution of SPI-Adaman (5.3 mg, 0.023 mmol) in 10% $Na_2CO_3$ (0.1 mL), followed by addition of 10% $Na_2CO_3$ (0.2 mL) to adjust pH value of the mixture to be around 9. The reaction was stirred at ambient temperature for 10 h, then diluted with $H_2O$ (5 mL), extracted with DCM (5 mL×3). The combined organic extracts were dried with anhydrous $MgSO_4$, filtered and concentrated. To resulting mixture was recrystallized from Pentane/EtOAc=10/1 to afford the pitavastatin precursor (17 mg, yield over two steps 51%) as a white solid.

$^1$H NMR (300 MHz, $d_6$-DMSO) δ 8.96 (d, J=4.2 Hz, 1H), 8.11 (d, J=8.3 Hz, 1H), 7.94 (d, J=8.5 Hz, 2H), 7.83-7.76 (m, 2H), 7.46 (d, J=8.3 Hz, 2H), 7.59 (d, J=7.2 Hz, 1H), 7.48 (d, J=4.3 Hz, 1H), 2.37 (s, 3H), 1.95 (d, J=12.6 Hz, 4H), 1.80 (s, 2H), 1.66 (d, J=10.9 Hz, 6H); $^{13}$C NMR (75 MHz, $d_6$-DMSO) δ 163.0, 150.6, 148.5, 146.2, 140.0, 132.8, 132.3, 130.1, 127.8, 125.9, 125.5, 122.0, 116.4, 105.6, 57.9, 36.9, 35.2, 33.7, 26.4; HRMS (m/z): [M+Na]$^+$ calc. for $C_{28}H_{24}INNaO_4$ 588.0648, found 588.0649.

I. Crizotinib

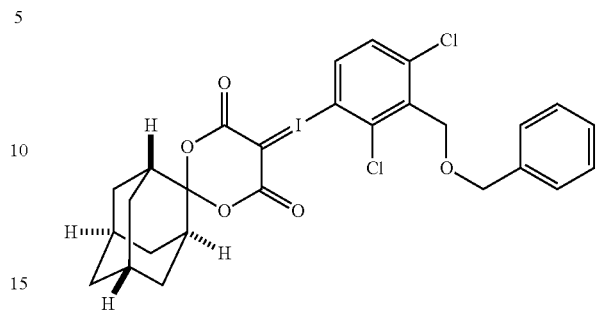

Step 1. 2,6-Dichloro-3-iodobenzoic acid

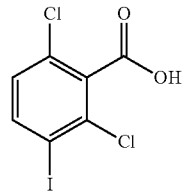 [SMILES: O=C(O)c1c(Cl)ccc(I)c1Cl]

To a stirred solution of 2,6-dichlorobenzoic acid (2.5 g, 13.1 mmol) in trifluoromethanesulfonic acid (10 mL) cooled to 0° C. was added N-iodosuccinimide (2.67 g, 11.9 mmol) in small portions over 30 min, with vigorous stirring. After 4 h, the reaction mixture was quenched with water. The product was extracted with dichloromethane, washed with 10% sodium thiosulfate (3×) and brine (1×). The organics were dried with anhydrous sodium sulfate, filtered, and concentrated. The product was either purified by flash chromatography or, alternatively, used in the next step without purification. The product 2,6-dichloro-3-iodobenzoic acid was light sensitive and produced 2,6-dichlorobenzoic acid on standing. The product was isolated in >90% purity as a pale brown solid (3.26 g, 10.3 mmol, 79% yield). $^1$H NMR (300 MHz, $CDCl_3$): δ 7.86 (d, J=8.6 Hz, 1H), 7.09 (d, J=8.6 Hz, 1H), 5.61 (br s, 1H) ppm. $^{13}$C NMR (75 MHz, $CDCl_3$): δ 168.5, 141.6, 136.0, 133.5, 131.8, 129.2, 97.0 ppm.

Step 2. (2,6-Dichlorophenyl)methanol & (2,6-dichloro-3-iodophenyl)methanol

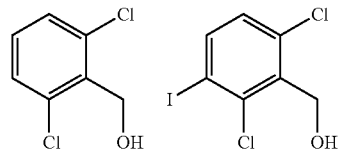

To a mixture of 2,6-dichlorobenzoic acid and 2,6-dichloro-3-iodobenzoic acid (molar ratio is about 1:1, 235 mg) was added dropwise $BH_3$.THF (1 M, 2.3 mL, 2.3 mmol) at ambient temperature. After addition, the resulting mixture was heated to reflux for 20 h. Methanol (10 mL) was added to quench the excess borane. Solvents and trimethyl borate by-product were evaporated under reduced pressure to dryness. The same process was repeated one more time. The residue was purified by column chromatography on silica gel (Hexanes/EtOAc=4/1) to afford a mixture of (2,6-dichlorophenyl)methanol and (2,6-dichloro-3-iodophenyl)methanol (molar ratio from 1H NMR was 1:1, total 160 mg) as light yellow oil, which was used in the next step without further purification.

Step 3, 2-((Benzyloxy)methyl)-1,3-dichlorobenzene & 2-((benzyloxy)methyl)-1,3-dichloro-4-iodobenzene

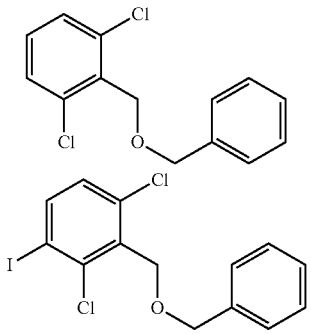

NaH (washed with hexanes for five times to remove mineral oil and dried in vacuo for 3 h, 12 mg, 0.5 mmol) was added to a well-stirred suspension of the benzyl alcohols (2,6-dichlorophenyl)methanol and (2,6-dichloro-3-iodophenyl)methanol (total 78 mg, 0.158 mmol of each one) in dry THF (1.0 mL) at room temperature under argon. After 30 min, the benzyl bromide (68 mg, 0.4 mmol) in THF (1 mL) were added dropwise, and the reaction mixture was stirred at 60° C. for 12 h. The mixture was then cooled to 0° C., and the excess sodium hydride was quenched with water (1 mL). The reaction mixture was then extracted with ethyl acetate (3 mL×3). The organic layers were combined and were washed with brine (5 mL). The residue was purified by column chromatography on silica gel (Hexanes/EtOAc=10/1) to afford a mixture of 2-((benzyloxy)methyl)-1,3-dichlorobenzene & 2-((benzyloxy)methyl)-1,3-dichloro-4-iodobenzene (molar ratio from $^1$H NMR was 1:1, total 108 mg) as light yellow solid, which was used in the next step without further purification.

Step 4. Crizotinib Precursor

In a $N_2$ charged round-bottom flask, the mixture of 2-((benzyloxy)methyl)-1,3-dichlorobenzene & 2-((benzyloxy)methyl)-1,3-dichloro-4-iodobenzene (total 108 mg, 0.164 mmol of each one) was dissolved in dry MeCN (2 mL). Trimethylsilyl acetate (54 mg, 0.41 mmol) and Selectfluor® (116 mg, 0.33 mmol) were added sequentially. The reaction mixture was allowed to stir at room temperature for 12 h. MeCN was removed by evaporation and the remaining yellow oil was treated with $H_2O$ (3 mL). The mixture was extracted with dichloromethane (3 mL×3). The organic layers were combined, washed with aqueous acetate buffer (NaOAc:HOAc=0.5 M:0.5 M, pH=5, 3 mL×3), dried over $Na_2SO_4$, filtered and evaporated under reduced pressure. Pentane (5 mL) and dichloromethane (0.5 mL) were added to the oil and mixture was placed in an ultrasonic bath and sonicated until the compound solidified. The solvent was decanted away, and the same procedure was repeated one additional time. The remaining solid was dried under vacuum for 2 h. The obtained diacetoxyiodoarene (33 mg, 0.065 mmol) was used in the next step.

A solution of the diacetoxyiodoarene (33 mg, 0.065 mmol) in EtOH (0.5 mL) was added a solution of SPI-Adaman (15.3 mg, 0.065 mmol) in 10% $Na_2CO_3$ (0.25 mL), followed by addition of 10% $Na_2CO_3$ (0.2 mL) to adjust pH value of the mixture to be around 10. The reaction was stirred at ambient temperature for 3 h, then diluted with $H_2O$ (2 mL), extracted with DCM (3 mL×3). The combined organic extracts were dried with anhydrous $MgSO_4$, filtered and concentrated. To resulting solid was added ethyl acetate/pentane (v/v=1/1, 2 mL), sonicated, allowed to settle and decanted. This process was repeated for three more times. After dryness using a vacuum pump, the crizotinib precursor (41 mg, yield over two steps 39%) was obtained as a white solid.

$^1$H NMR (300 MHz, $d_6$-DMSO) δ 7.82 (d, J=8.6 Hz, 1H), 7.58 (d, J=8.6 Hz, 1H), 7.34-7.27 (m, 5H), 4.77 (s, 2H), 4.57 (s, 2H), 2.25 (br s, 2H), 1.88 (d, J=12.4 Hz, 4H), 1.75 (s, 2H), 1.60 (d, J=11.7 Hz, 6H); $^{13}$C NMR (75 MHz, d-DMSO) 162.6, 139.0, 138.8, 138.2, 137.8, 137.0, 135.2, 131.0, 128.7, 128.1, 118.8, 105.6, 72.7, 67.9, 59.4, 36.9, 35.3, 33.6, 26.3. HRMS (m/z): [M+Na]$^+$ calc. for $C_{27}H_{25}Cl_2INaO_5$ 649.0021, found 649.0025.

Example 32. Synthesis and Characterization of $^{19}$F-Standards $^{19}$F-standards of the Drug Precursors described in Example 31 were prepared according to the following procedures.

A. Filorexant

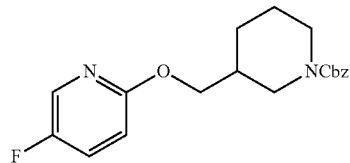 [SMILES: O=C(OCc1ccccc1)N1CCCC(COc2ccc(F)cn2)C1]

In a 100 mL reaction vessel was charged the solution of piperidine S1-3 (428 mg, 1.09 mmol) in NMP (10 mL), 5-fluoropyridin-2-ol (149 mg, 1.33 mmol), and $Cs_2CO_3$ (926 mg, 2.84 mmol). The mixture was heated to 60° C. and stirred for 26 h. It was cooled to 15° C. before addition of water (60 mL) over 5 min, keeping the temperature below 25° C. The solution was extracted with ethyl ether (15 mL×3). The organic layer was washed with 10 wt % LiCl (10 mL×2) and brine (10 mL×2). The organics were dried over sodium sulfate, filtered and evaporated in vacuo. The residue was purified by column chromatography on silica gel (Hexanes/EtOAc=3/1) to afford benzyl 3-(((5-iodopyridin-2-yl)oxy)methyl)piperidine-1-carboxylate (1.04 g, 2.3 mmol) as colorless oil.[3] $^1$H NMR (300 MHz, CDCl$_3$) δ 7.94 (d, J=3.2 Hz, 1H), 7.34-7.28 (m, 6H), 6.68 (d, J=7.4 Hz, 1H), 5.12 (s, 2H), 4.26-4.13 (m, 2H), 4.10-3.99 (m, 2H), 2.90 (br s, 1H), 2.71 (br s, 1H), 2.10-1.95 (m, 1H), 1.94-1.82 (m, 1H), 1.77-1.64 (m, 1H), 1.60-1.43 (m, 1H), 1.41-1.22 (m, 1H); $^{13}$C NMR (75 MHz, CDCl$_3$) δ 159.9, 156.9, 155.3, 153.7, 136.9, 132.9 (d, J=27 Hz), 128.4, 127.8 (d, J=11 Hz), 126.5 (d, J=22 Hz), 111.6, 68.2, 66.9, 47.2, 44.6, 35.7, 27.3; HRMS (m/z): [M+Na]$^+$ calc. for $C_{19}H_{21}FN_2NaO_3$ 345.1614, found 345.1615.

B. Mosapride

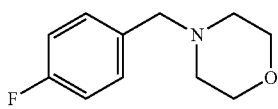 [SMILES: Fc1ccc(CN2CCOCC2)cc1]

The mosapride $^{19}$F-standard was prepared by reductive amination according to the procedures described in Bhattacharyya et al., *Synth. Commun.* 1997, 27:4265-4274.

C. Lapatinib

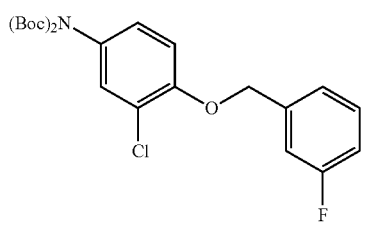

Step 1, tert-Butyl (3-chloro-4-((3-fluorobenzyl)oxy) phenyl)carbamate

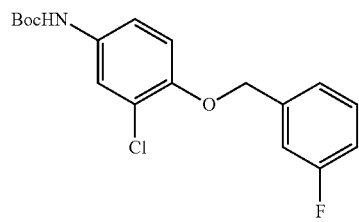

A solution of the tert-butyl (3-chloro-4-hydroxyphenyl) carbamate S3-2 (449 mg, 1.84 mmol) in anhydrous DMF (7 mL) was added $K_2CO_3$ (1.27 g, 9.2 mmol) and 1-(bromomethyl)-3-fluorobenzene (365 mg, 1.9 mmol). The resulting solution was then stirred at 100° C. for 3 h under Ar. The reaction mixture was cooled to ambient temperature and quenched with water (50 mL), and then extracted with ethyl ether (15 mL t 3). The organic layers were combined, washed with brine, dried over $Na_2SO_4$, filtered and evaporated under reduced pressure. The crude product was purified by flash chromatography (Hexanes/EtOAc=5/1) to afford tert-butyl (3-chloro-4-((3-fluorobenzyl)oxy) phenyl) carbamate (552 mg, yield 85%) as white solid. $^1$H NMR (300 MHz, $CDCl_3$) δ 7.50 (d, =2.5 Hz, 1H), 7.37-7.29 (m, 1H), 7.21-7.10 (m, 3H), 6.99 (td, J=8.8, 2.0 Hz, 1H), 6.84 (d, J=8.9 Hz, 1H), 6.45 (s, 1H), 5.08 (s, 2H), 1.51 (s, 9H), $^{13}$C NMR (75 MHz, $CDCl_3$) δ 164.6, 161.3, 152.8, 149.8, 139.1 (d, J=7.2 Hz), 132.7, 130.1 (d, J=8.2 Hz), 123.7, 122.4 (d, J=2.8 Hz), 121.2, 118.1, 114.8 (t, J=10.6 Hz), 113.9 (d, J=22.2 Hz), 80.7, 70.5 (d, J=2.2 Hz), 28.3: HRMS (m/z): [M+Na]+ calc, for $C_{23}H_{27}ClFNNaO_5$ 474.1459, found 474.1460.

Step 2. [19]F-Lapatinib Standard

A solution of the tert-butyl (3-chloro-4-((3-fluorobenzyl) oxy)phenyl)carbamate (524 mg, 1.49 mmol) in anhydrous THF (5 mL) was added $Et_3N$ (0.6 mL, 4.35 mmol), DMAP (176 mg, 1.49 mmol) and t-$Boc_2O$ (654 mg, 3.0 mmol). The resulting solution was stirred at ambient temperature for 15 h under Ar. The reaction was quenched with water (50 mL), and then extracted with ethyl acetate (15 mL×3). The organic layers were combined, washed with brine, dried over $Na_2SO_4$, filtered and evaporated under reduced pressure. The crude product was purified by flash chromatography (Hexanes/EtOAc=5/1) to afford compound the $^{19}$F-lapatinib standard (572 mg, yield 85%) as a white solid. $^1$H NMR (300 MHz, $CDCl_3$) δ 7.38-7.31 (m, 1H), 7.23-7.17 (m, 3H), 7.01 (td, J=8.7, 2.5 Hz, 2H), 6.90 (d, J=8.6 Hz, 1H), 5.15 (s, 2H), 1.43 (s, 18H); $^{13}$C NMR (75 MHz, $CDCl_3$) δ 164.6, 161.3, 153.1, 151.7, 138.8 (d, J=7.2 Hz), 132.9, 130.1 (d, J=7.7 Hz), 127.3, 122.9, 122.3 (d, J=2.8 Hz), 114.9 (d, J=21.2 Hz), 113.9 (d, J=22.2 Hz), 113.5, 82.9, 70.1 (d, J=1.7 Hz), 27.9: HRMS (m/z): [M+Na]+ calc, for $C_{18}H_{19}ClFNNaO_3$ 374.0935, found 374.0936.

D. Risperidone

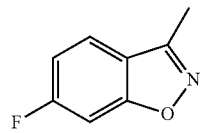

Step 1, 5-Fluoro-2-(1-iminoethyl)phenol

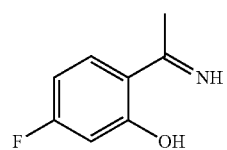

1-(4-fluoro-2-hydroxyphenyl)ethan-1-one (1.0 g, 6.49 mmol) in 7 M ammonia in MeOH (4.6 ml, 32.4 mmol) was stirred at ambient temperature for 2 h to give a yellow slurry. The slurry was filtered and the cake was dried to afford 5-fluoro-2-(1-iminoethyl) phenol (466 mg, yield 47%) as bright yellow solid, which was used in the next step without further purification.

Step 2. [19]F-Risperidone Standard

A mixture of 5-fluoro-2-(1-iminoethyl)phenol (466 mg, 3.04 mmol), NCS (607 mg, 4.55 mmol) and $K_2CO_3$ (837 mg, 6.06 mmol) in THF (9 mL) was stirred at ambient temperature for 12 h. Ethyl acetate (20 mL) and water (15 mL) was added to the reaction mixture and the organic layer was separated, dried over $MgSO_4$, and concentrated in vacuum. The crude product was purified by flash chromatography (Hexanes/EtOAc=6/1) to afford the [$^{19}$F]-risperidone standard, 6-fluoro-3-methylbenzo[d]isoxazole (300 mg, yield 66%) as yellow solid. Characterized according to a literature procedure.[14] HRMS (m/z): [M+Na]+ calc, for $C_8H_6FNNaO$ 152.0512, found 152.0514.

E. Ezetimibe

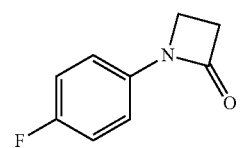

Step 1, 3-Bromo-N-(4-fluorophenyl)propanamide

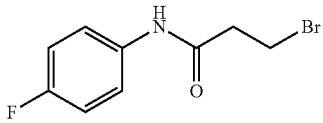

The sub-title product was prepared according to procedures described in Saxena et al., *Bioorg. Med. Chem.* 2006, 14:8249-8258.

Step 2. $^{19}$F-Ezetimibe Standard

The sub-title product was prepared according to procedures described in Schmidt et al., *Eur. J. Org. Chem.* 2012, 681-684. HRMS (m/z): [M+Na]$^+$ calc, for $C_9$HFNNaO 188.0488, found 188.0490.

F. Astemizole

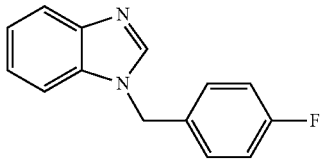 [SMILES: Fc1ccc(Cn2cnc3ccccc32)cc1]

NaH (washed with hexanes for five times to remove mineral oil and dried in vacuo for 3 h, 55 mg, 2.3 mmol)) was added in portions to a solution of benzimidazole (180 mg, 1.53 mmol) in dry THF under argon atmosphere at 0° C. The solution was stirred at ambient temperature for 3 h. At 0° C. 1-(bromomethyl)-4-fluorobenzene (317 mg, 1.67 mmol) was added carefully and the reaction mixture was heated at 65° C. for 15 h. The reaction was quenched with H$_2$O (15 mL) and extracted with EtOAc (15 mL×3). The combined organic phases were dried over MgSO$_4$, filtered, and evaporated. The crude product was purified by flash chromatography (Hexanes/EtOAc=2/1 to 0/1, then EtOAc/MeOH=50:1) to afford the [$^{19}$F]-astemizole standard, 1-(4-fluorobenzyl)-1H-benzo[d]imidazole (251 mg, yield 73%) as a colorless oil. HRMS (m/z): [M+Na]$^+$ calc, for $C_{14}H_{11}FN_2Na$, 249.0804, found 249.0805.

G. Paroxetine

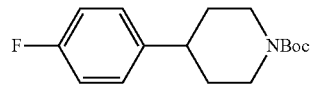

A well-stirred solution of 4-(4-fluorophenyl)piperidine hydrochloride salt (430 mg, 2.00 mmol) in DCM (10 mL) was treated with triethylamine (1.0 g, 10.0 mmol), followed by addition of t-Boc$_2$O (523 mg, 2.4 mmol) at 0° C. The mixture was stirred at room temperature for 20 h and then quenched with H$_2$O (20 mL), extracted with dichloromethane (15 mL×3), washed with brine, dried over sodium sulfate, filtered and evaporated in vacuo. The residue was purified by column chromatography on silica gel (Hexanes/EtOAc=8/1) to afford the [$^{19}$F]-paroxetine standard, tert-butyl 4-(4-fluorophenyl)piperidine-1-carboxylate (508 mg, yield 91%) as a colorless oil. $^1$H NMR (300 MHz, CDCl$_3$) δ 7.17-7.11 (m, 2H), 7.02-6.95 (m, 2H), 4.24 (dt, J=13.4, 2.1 Hz, 2H), 2.78 (td, J=10.5, 2.7 Hz, 2H), 2.62 (tt, J=12.2, 3.7 Hz, 1H), 1.82-1.76 (m, 2H), 1.59 (td, J=12.5, 4.3 Hz, 2H), 1.48 (s, 9H): $^{13}$C NMR (75 MHz, CDCl$_3$) δ 162.9, 159.7, 154.7, 141.3 (d, J=3.3 Hz), 128.0 (d, J=7.7 Hz), 115.1 (d, J=20.9 Hz), 79.4, 44.3, 41.9, HRMS (m/z): [M+Na]$^+$ calc, for $C_{16}H_{22}FNNaO_2$ 302.1532, found 302.1535.

H. Pitavastatin

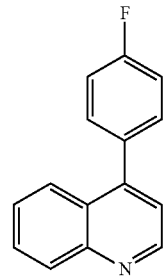 [SMILES: Fc1ccc(-c2ccnc3ccccc23)cc1]

To an oven-dried flask (10 mL) under an argon atmosphere were charged of toluene (1.0 mL), quinolin-4-yl acetate (30 mg, 0.16 mmol), (4-fluorophenyl)boronic acid (27 mg, 0.19 mol), Pd$_2$(dba)$_3$ (1.84 mg, 0.0032 mmol) and SPhos (2.6 mg, 0.0064 mmol). The mixture was degassed with argon for 15 min, and then agitated at 100° C. for 20 h. To the agitated solution was charged ethyl acetate (3 mL), followed by 5% NaOH (0.5 mL). The mixture was stirred for 10 min. The aqueous phase was cut. The organic phase was washed with 10% brine (10 mL), dried over sodium sulfate, filtered and evaporated in vacuo. The residue was purified by column chromatography on silica gel (Hexanes/EtOAc=3/1) to afford the [$^{19}$F]-pitavastatin standard, 4-(4-fluorophenyl) quinoline (27 mg, yield 75%) as light purple oil. $^1$H NMR (300 MHz, CDCl$_3$) δ 8.94 (d, J=4.3 Hz, 1H), 8.21 (d, J=8.6 Hz, 1H), 7.89 (d, J=8.6 Hz, 1H), 7.75 (dt, J=6.8, 1.3 Hz, 1H), 7.56-7.46 (m, 3H), 7.33 (d, J=4.5 Hz, 1H), 7.26-7.20 (m, 2H); $^{13}$C NMR (75 MHz, CDCl$_3$) δ 164.6, 161.3, 149.6, 148.3, 147.8, 133.8 (d, J=3.4 Hz), 131.2 (d, J=8.2 Hz), 129.6, 126.9, 125.6, 121.3, 115.8, 115.5; HRMS (m/z): [M+Na]$^+$ calc, for $C_{15}H_{10}FNNa$ 246.0695, found 246.0698.

I. Crizotinib

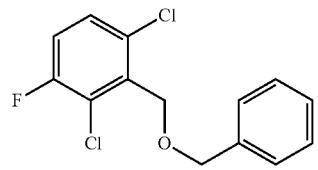 [SMILES: Fc1ccc(Cl)c(COCc2ccccc2)c1Cl]

Step 1. 2,6-Dichloro-3-fluorobenzaldehyde

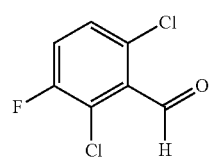

To 2,4-dichloro-1-fluorobenzene (2.0 g, 12.1 mmol) in THF (28 mL) was added dropwise nBuLi (2.5 M, 5.3 mL, 13.3 mmol) at −78° C. over a period of 30 min. After 1.0 h stirring at −78° C., methyl formate (1.45 g, 24.2 mmol) was added slowly and the reaction mixture was stirred overnight, warming up to ambient temperature. The reaction was diluted with EtOAc (20 mL) and quenched with saturated aqueous NH$_4$Cl (20 mL). The organic layer was separated and dried over Na$_2$SO$_4$. The organic solvents were removed and the crude material was crystallized from hexanes to give 2,6-dichloro-3-fluorobenzaldehyde as a light yellow solid (crude compound, 1.1 g), which was used without further purification.

Step 2. (2,6-Dichloro-3-fluorophenyl)methanol

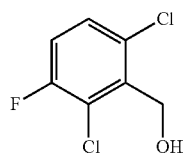

To 2,6-dichloro-3-fluorobenzaldehyde (390 mg, 2.02 mmol) in MeOH (7 mL) was added NaBH$_4$ (115 mg, 3.03 mmol) at 0° C. After stirring for 2 h at 0° C., the reaction was diluted with EtOAc (10 mL) and quenched with saturated brine (10 mL). The organic layer was separated and dried over Na$_2$SO$_4$. The organic solvents were removed and the crude material was purified by column chromatography on silica gel (Hexanes/EtOAc=10/1) to afford benzyl alcohol (389 mg, yield 99%) as colorless oil. The sub-title compound was confirmed by comparison with published characterization data (see e.g., Li et al., *ACS Med. Chem. Lett.* 2013, 4:806-810).

Step 3. $^{19}$F-Crizotinib Standard

NaH (washed with hexanes for five times to remove mineral oil and dried in vacuo for 3 h, 72 mg, 3.0 mmol) was added to a well-stirred suspension of the benzyl alcohols S9-10 (389 mg, 2.0 mmol) in dry THF (6.0 mL) at room temperature under argon. After 30 min, the benzyl bromide (376 mg, 2.2 mmol) in THF (2 mL) were added dropwise, and the reaction mixture was stirred at 60° C. for 2.5 h. The mixture was then cooled to 0° C., and the excess sodium hydride was quenched with water (4 mL). The reaction mixture was then extracted with ethyl acetate (4 mL×3). The organic layers were combined and were washed with brine (5 mL). The residue was purified by column chromatography on silica gel (Hexanes/EtOAc=15/1) to afford the [$^{19}$F]-crizotinib standard, 2-((benzyloxy)methyl)-1,3-dichloro-4-fluorobenzene (479 mg, yield 84%) as colorless oil, 1H NMR (300 MHz, CDCl$_3$) δ 7.44-7.28 (m, 6H), 7.09 (t, J=8.3 Hz, 1H), 4.83 (s, 2H), 4.66 (s, 2H); $^{13}$C NMR (75 MHz, CDCl$_3$) δ 158.7, 155.4, 137.8, 135.3, 131.3 (d, J=3.9 Hz), 128.5 (d, J=7.2 Hz), 128.3, 127.8 (d, J=5.5 Hz), 124.0 (d, J=18.2 Hz), 116.8 (d, J=23.1 Hz), 73.0, 66.6 (J=2.1 Hz). HRMS (m/z): [M+Na]+ calc, for C14H11Cl2FNaO 307.0069, found 307.0073.

Example 33. Preparation of Precursor to [$^{18}$F]Safinamide

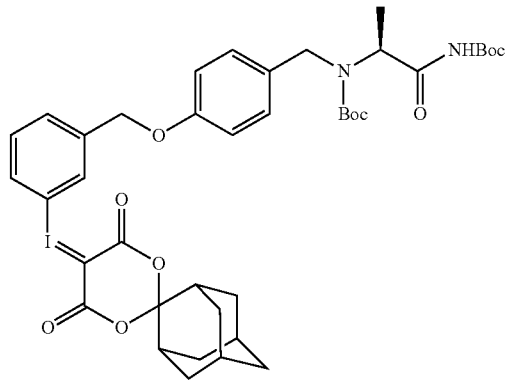 [SMILES: C[C@@H](C(=O)NC(=O)OC(C)(C)C)N(Cc1ccc(OCc2cccc(I=C3C(=O)OC4(OC3=O)C3CC5CC(C3)CC4C5)c2)cc1)C(=O)OC(C)(C)C]

Step 1. (S)-2-((4-((3-Iodobenzyl)oxy)benzyl)amino)propanamide

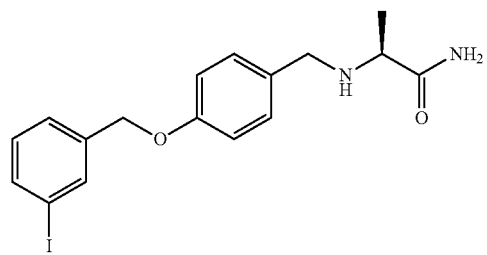 [SMILES: C[C@H](NCc1ccc(OCc2cccc(I)c2)cc1)C(N)=O]

The aryliodide analog of safinamide was prepared using similar procedures to those for the preparation of safinamide. Iodidefluorosafinamide was isolated as colourless solid. $^1$H NMR (300 MHz, CDCl$_3$): δ 7.79 (s, 1H), 7.65 (d, J=7.8 Hz, 1H), 7.38 (d, J=7.8 Hz, 1H), 7.22 (d, J=8.6 Hz, 2H), 7.11 (t, J=7.8 Hz, 1H), 6.92 (d, J=8.6 Hz, 2H), 5.64 (br s, 1H), 4.99 (s, 2H), 3.71 (apparent q, J=7.7, 13.0 Hz, 2H), 3.24 (q, J=7.0 Hz, 1H), 1.77 (br s, 1H), 1.34 (d, J=6.9 Hz, 3H) ppm. $^{13}$C NMR (75 MHz, CDCl$_3$): δ 177.9, 157.7, 139.3, 137.0, 132.1, 130.3, 129.3, 126.5, 114.9, 94.4, 69.0, 57.6, 51.9, 19.6 ppm.

Step 2. (S)-tert-Butyl (1-((tert-butoxycarbonyl)amino)-1-oxopropan-2-yl)(4-((3-iodobenzyl)oxy)benzyl)carbamate

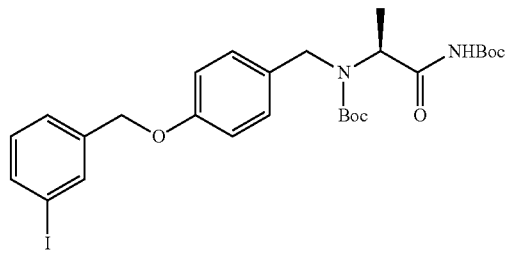 [SMILES: C[C@@H](C(=O)NC(=O)OC(C)(C)C)N(Cc1ccc(OCc2cccc(I)c2)cc1)C(=O)OC(C)(C)C]

Iododefluorosafinamide (500 mg, 1.2 mmol) was added to neat di-tert-butyl dicarbonate (5.24 g, 24 mmol), heated to 40° C. Triethylamine (1 mL, 7.2 mmol) and N,N-dimethylaminopyridine (74 mg, 0.6 mmol) were added and the reaction mixture heated to 80° C. for 30 min. The reaction mixture was diluted with ethyl acetate, and washed sequentially with water, 1 M HCl, and brine. The organic fraction was collected, dried with $Na_2SO_4$, filtered and concentrated. The product was then purified by flash chromatography (5-50% EA/Hex) to yield (S)-tert-butyl (1-((tert-butoxycarbonyl)amino)-1-oxopropan-2-yl)(4-((3-iodobenzyl)oxy)benzyl)carbamate as a colourless residue (400 mg, 0.66 mmol, 55%). $^1$H NMR (300 MHz, $CDCl_3$): δ 7.77 (s, 1H), 7.65 (d, J=7.8 Hz, 1H), 7.37 (d, J=7.8 Hz, 1H), 7.26 (d, J=8.6 Hz, 2H, obscured by solvent residual signal), 7.11 (t, J=7.8 Hz, 1H), 6.89 (d, J=8.6 Hz, 2H), 4.98 (s, 2H), 4.56 (d, J=15.3 Hz, 1H), 4.33 (d, J=15.3 Hz, 1H), 1.60 (s, 9H), 1.48 (s, 3H), 1.29 (s, 9H) ppm. $^{13}$C NMR (75 MHz, $CDCl_3$): δ 167.6, 164.9, 158.5, 152.2, 146.0, 139.3, 137.2, 136.3, 130.4, 130.3, 128.7, 126.6, 115.1, 94.6, 86.0, 84.6, 69.1, 68.3, 44.2, 28.0, 27.6 ppm.

Step 3. Precursor to [$^{18}$F]Safinamide

A solution of di-Boc-protected iododefluorosafinamide from Step 2 (183 mg, 0.3 mmol) in acetone and acetic acid (4:1, 2.2 mL) was cooled to 0° C. and treated with a solution of DMDO in acetone. The reaction mixture was stirred at 0° C. for 1 h, then warmed to room temperature and stirred for an additional 3 h. The reaction mixture was then concentrated, diluted with ethanol (1.2 mL), treated with (1r,3r,5r,7r)-spiro[adamantane-2,2'-[1,3]dioxane]-4',6'-dione (71 mg) in 10% aqueous sodium carbonate (0.9 mL) and the pH was adjusted to ~10 using 10% aqueous sodium carbonate. The reaction was then stirred for 2-4 h, and then diluted with water and extracted three times with dichoromethane. The pooled organics were dried using sodium sulfate, filtered concentrated and purified by flash chromatography ($SiO_2$, 50-100% EA/Hex) to yield the safinamide precursor as a colourless solid (SF-5, 78 mg, 31% yield). $^1$H NMR (300 MHz, $CDCl_3$): δ 7.92 (s, 1H), 7.81 (d, J=8.2 Hz, 1H), 7.61 (d, J=7.7 Hz, 1H), 7.43 (t, J=7.9 Hz, 1H), 7.27 (d, 2H, obscured by solvent residual signal), 6.88 (d, J=8.6 Hz, 2H), 5.04 (s, 2H), 4.60 (d, J=15.3 Hz, 1H), 4.28 (d, J=15.4 Hz, 1H), 2.43 (br s, 2H), 2.18 (br s, 2H), 2.14 (br s, 2H), 1.85 (br s, 2H), 1.71 (br s, 4H), 1.67 (br s, 2H), 1.59 (s, 9H), 1.48 (m, 3H), 1.32 (s, 9H) ppm. $^{13}$C NMR (75 MHz, $CDCl_3$): δ 164.9, 163.5, 158.1, 152.2, 146.0, 141.6, 132.8, 132.1, 131.7, 130.8, 130.4, 129.2, 115.1, 114.4, 107.8, 86.0, 84.6, 68.7, 68.4, 55.9, 44.3, 37.3, 35.7, 33.9, 28.0, 27.7, 26.6, 18.4 ppm. HRMS (m/z): [M+Na]$^+$ calc. for $C_{45}H_{57}IN_2NaO_{13}$ 983.2803, found 983.2805.

The $^{19}$F-standard safinamide was prepared according to known literature procedures.

Example 34. Preparation of 6-[$^{18}$F]Fluoro-Meta-Tyrosine Precursor

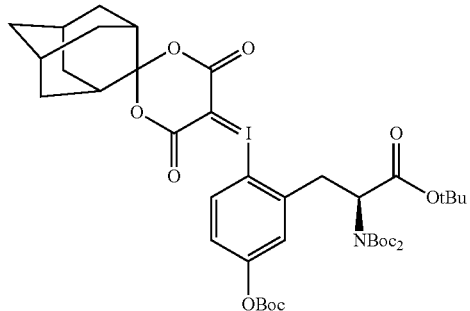

Step 1. (S)-tert-Butyl 2-amino-3-(3-hydroxyphenyl)propanoate

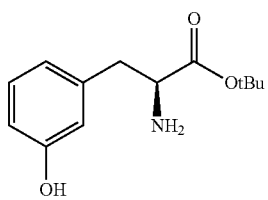 [SMILES: CC(C)(C)OC(=O)[C@@H](N)Cc1cccc(O)c1]

To a mixture of L-meta-tyrosine (1.0 g, 5.5 mmol) and tert-butyl acetate (11 mL) at 0° C. was slowly added perchloric acid (0.5 mL, 8.3 mmol).[23,24] The reaction mixture was then warmed to room temperature and stirred for 4 h, before sequential extraction with water and 1 M HCl. The aqueous fractions were then adjusted to pH 9 by addition of 10% $K_2CO_3$ and extracted three times with dichloromethane. The pooled organic fractions were dried with anhydrous sodium sulfate, filtered, and concentrated. The crude product, (S)-tert-butyl 2-amino-3-(3-hydroxyphenyl)propanoate, was used in the following step without further purification. $^1$H NMR (300 MHz, $CDCl_3$): δ 7.16 (t, J=7.6 Hz, 1H), 6.74 (d, J=7.6 Hz, 1H), 6.72-6.68 (m, 2H), 3.63 (t, J=5.4 Hz, 1H), 3.01 (dd, J=5.4, 13.6 Hz, 1H), 2.83 (dd, J=7.7, 13.6 Hz, 1H), 1.45 (s, 9H) ppm.

Step 2. (S)-tert-butyl 2-((ter-butoxycarbonyl)amino)-3-(3-((tert-butoxycarbonyl)oxy)phenyl)propanoate

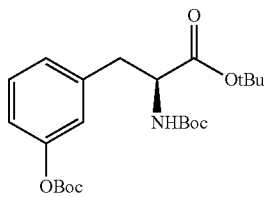

To a solution of L-meta-tyrosine tert-butyl ester (~5.5 mmol) in DMF (4 mL) was slowly added triethylamine (2.3 mL, 16.5 mmol). The reaction mixture was then cooled to 0°

C., and a solution of di-tert-butyl dicarbonate (3.00 g, 13.75 mmol) in DMF (4 mL) was added over 10 minutes. The reaction mixture was then warmed to room temperature and stirred for 48 h. The reaction mixture was then diluted with ethyl acetate and washed with brine (3×100 mL). The pooled organic phases were then extracted with ethyl acetate and then the combined organic phases were dried with sodium sulfate, filtered, and concentrated. The crude mixture was purified by flash chromatography (SiO$_2$, 5-25% EA/Hex) to yield (S)-tert-butyl 2-((tert-butoxycarbonyl)amino)-3-(3-((tert-butoxycarbonyl)oxy)phenyl)propanoate as a pale yellow oil (2 g, 4.6 mmol, 83% yield over two steps. $^1$H NMR (300 MHz, CDCl$_3$): δ 7.28 (t, J=7.7 Hz, 1H), 7.05-6.98 (m, 3H), 5.00 (d, J=7.7 Hz, 1H), 4.44 (dd, J=6.0, 13.6 Hz, 1H) 3.06 (d, J=6.0 Hz, 1H), 1.55 (s, 9H), 1.42 (s, 9H), 1.39 (s, 9H) ppm.

Step 3. (S)-tert-Butyl 2-((tert-butoxycarbonyl)amino)-3-(5-((tert-butoxycarbonyl)oxy))-2-iodophenyl)propanoate

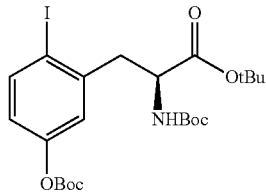

To a solution of (S)-tert-butyl 2-((tert-butoxycarbonyl)amino)-3-(3-((tert-butoxycarbonyl)oxy)phenyl)propanoate (2 g, 4.6 mmol) in dichloromethane (38 mL) at room temperature and under argon was added silver(I) trifluoroacetate (1.25 g, 5.7 mmol), followed by iodine (1.28 g, 5.1 mmol). The flask was sealed from light and vigorously stirred at room temperature for 48 h. The mixture was then filtered through a small pad of Celite over a glass frit to remove solids. The filtrate was concentrated and purified by flash chromatography (SiO$_2$, 10-25% EA/Hex) to yield a yellow oil (MT-4, 1.86 g, 3.3 mmol, 72% yield). $^1$H NMR (300 MHz, CDCl$_3$): δ 7.80 (d, J=8.4 Hz, 1H), 7.07 (d, J=2.8 Hz, 1H), 6.81 (d, J=8.4 Hz, 1H), 5.04 (d, J=8.7 Hz, 1H), 4.53 (dd, J=9.3, 15.3 Hz, 1H), 3.22 (dd, J=5.9, 14.2 Hz, 1H), 3.03 (dd, J=8.2, 13.6 Hz, 1H), 1.54 (s, 9H), 1.41 (s, 9H), 1.38 (s, 9H) ppm.

Step 4. (S)-tert-Butyl 2-(bis(tert-butoxycarbonyl)amino)-3-(5-((tert-butoxycarbonyl)oxy)-2-iodophenyl)propanoate

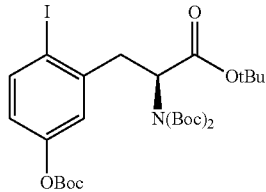

To a solution of (S)-tert-butyl 2-((tert-butoxycarbonyl)amino)-3-(5-((tert-butoxycarbonyl)oxy)-2-iodophenyl)propanoate (1.86 g, 3.3 mmol) in anhydrous THF (22 mL) under argon was added N,N-dimethylaminopyridine (2.02 g, 16.5 mmol). The solution was cooled to 0° C., and di-tert-buty dicarbonate (2.7 g, 12.4 mmol) was added and the reaction was stirred at room temperature overnight. The reaction mixture was then diluted with ethyl acetate, washed twice with water, and once with brine. The organic fractions were then dried over sodium sulfate, filtered, concentrated and purified by flash chromatography (SiO$_2$, 2-25% EA/Hex) to yield the desired product a yellow oil (87% yield). $^1$H NMR (300 MHz, CDCl$_3$): δ 7.75 (d, J=8.6 Hz, 1H), 6.99 (d, J=2.7 Hz, 1H), 6.77 (dd. J=2.7, 8.6 Hz, 1H), 5.16 (dd, J=4.4, 10.7 Hz, 1H), 3.52 (dd, J=4.4, 14.3 Hz, 1H), 3.36 (dd, J=10.7, 14.3 Hz, 1H), 1.53 (s, 9H), 1.47 (s, 9H), 1.40 (s, 18H) ppm. $^{13}$C NMR (75 MHz, CDCl$_3$): δ 169.0, 152.3, 152.2, 151.4, 151.3, 142.6, 140.2, 139.9, 124.0, 121.5, 96.6, 83.7, 82.9, 81.9, 81.1, 58.2, 28.1, 28.0, 27.8 ppm. HRMS (m/z): [M+Na]$^+$ calc, for C$_{28}$H$_{42}$INNaO$_8$ 686.1802, found 686.1805.

Step 5. Precursor to 6-[18F]Fluoro-Meta-Tyrosine

A solution of the product from Step 4 (199 mg, 0.3 mmol) in acetone and acetic acid (4:1, 2.2 mL) was cooled to 0° C. and treated with a solution of DMDO in acetone. The reaction mixture was stirred at 0° C. for 1 h, then warmed to room temperature and stirred for an additional 3 h. The reaction mixture was then concentrated, diluted with ethanol (1.2 mL), treated with (1r,3r,5r,7r)-spiro[adamantane-2,2'-[1,3]dioxane]-4',6'-dione (71 mg) in 10% aqueous sodium carbonate (0.9 mL) and the pH was adjusted to ~10 using 10% aqueous sodium carbonate. The reaction was then stirred for 2-4 h, and then diluted with water and extracted three times with dichoromethane. The pooled organics were dried using sodium sulfate, filtered concentrated and purified by flash chromatography (SiO$_2$, 10-50% EA/Hex) to yield the 6-[$^{18}$F]fluoro-meta-tyrosine precursor as a colourless solid (85 mg, 32% yield). $^1$H NMR (300 MHz, CDCl$_3$): δ 8.02 (d, J=8.8 Hz, 1H), 7.23 (d, J=2.8 Hz, 1H), 7.05 (dd, J=2.8, 8.8 Hz, 1H), 4.94 (dd, J=5.3, 9.1, 1H), 3.88 (dd, J=9.2, 14.2 Hz, 1H), 3.25 (dd, J=5.3, 14.2 Hz, 1H), 2.40 (br s, 2H), 2.18 (br s, 2H), 2.14 (br s, 2H), 1.83 (br s, 2H), 1.70 (br s, 4H), 1.65 (br s, 2H), 1.55 (s, 9H), 1.49 (s, 18H), 1.42 (s, 9H) ppm. $^{13}$C NMR (75 MHz, CDCl$_3$): δ 169.5, 164.2, 153.7, 152.4, 150.9, 141.6, 136.3, 124.4, 123.3, 119.2, 107.3, 84.5, 84.0, 83.3, 59.6, 56.5, 39.9, 37.4, 35.7, 33.9, 28.2, 28.0, 27.8, 26.7 ppm. HRMS (m/z): [M+Na]$^+$ calc, for C$_{41}$H$_{56}$INNaO$_{13}$ 920.2694, found 920.2699.

Example 35. Preparation of [$^{18}$F]Meta-Fluorobenzylguanidine Precursor

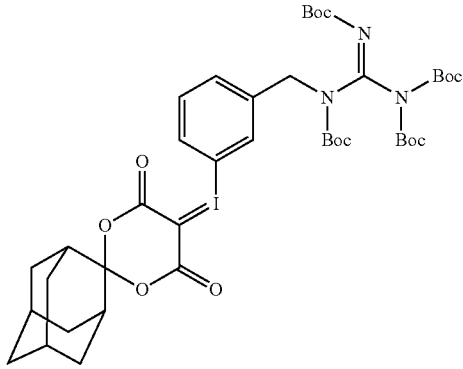 [SMILES: CC(C)(C)OC(=O)/N=C(\N(Cc1cccc(I=C2C(=O)OC3(OC2=O)C2CC4CC(C2)CC3C4)c1)C(=O)OC(C)(C)C)N(C(=O)OC(C)(C)C)C(=O)OC(C)(C)C]

Step 1

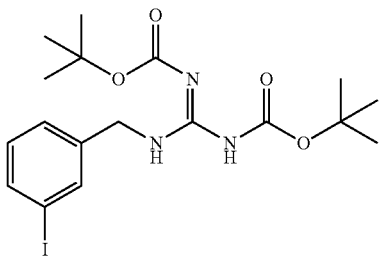 [SMILES: CC(C)(C)OC(=O)/N=C(\NCc1cccc(I)c1)NC(=O)OC(C)(C)C]

To a mixture of meta-iodobenzylamine hydrochloride (270 mg, 1.0 mmol), triethylamine (0.42 mL, 3.0 mmol), and dimethylformamide (0.5 mL) was added 1,3-bis(tert-butoxycarbonyl)-2-methyl-2-thiopseudourea (348 mg, 1.2 mmol) and an additional aliquot of dimethylformamide (0.5 mL). The heterogeneous reaction mixture was stirred at room temperature for 14 h, then diluted with ethyl acetate, and washed sequentially with water and brine. The pooled organic fractions were dried with sodium sulfate, filtered, and concentrated to yield a solid with a slight residual scent of methyl sulfide. The product was purified by flash chromatography to yield the desired product as a colourless solid (440 mg, 0.93 mmol, 93%). $^1$H NMR (300 MHz, CDCl$_3$): δ 11.53 (br s, 1H), 8.58 (br s, 1H), 7.66 (s, 1H), 7.61 (d, J=7.6 Hz, 1H), 7.27 (d, J=7.6 Hz, 1H), 7.07 (t, J=7.6 Hz, 1H), 4.57 (d, J=5.4 Hz, 2H), 1.51 (s, 9H), 1.48 (s, 9H) ppm. $^{13}$C NMR (75 MHz, CDCl$_3$): δ 163.5, 156.1, 153.2, 139.8, 136.9, 136.7, 130.4, 127.1, 94.5, 83.3, 79.5, 44.1, 28.3, 28.0, ppm.

Step 2

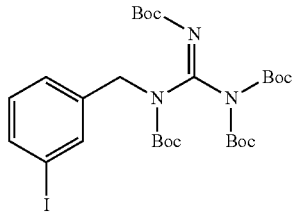 [SMILES: CC(C)(C)OC(=O)/N=C(\N(Cc1cccc(I)c1)C(=O)OC(C)(C)C)N(C(=O)OC(C)(C)C)C(=O)OC(C)(C)C]

To a solution of the product from Step 1 (238 mg, 0.5 mmol) in tetrahydrofuran (3.33 mL) under argon was added N,N-dimethylaminopyridine (305 mg, 2.5 mmol). The mixture was cooled to 0° C. and di-tert-butyl dicarbonate (409 mg, 1.88 mmol) was added over 10 minutes. The reaction was stirred at room temperature for 2 hours, diluted with ethyl acetate, and washed with water. The organic fraction was dried with anhydrous sodium sulfate, filtered, concentrated, and purified by flash chromatography (SiO$_2$, 2-20%/o EA/Hex) to yield the desired product as a colourless oil (316 mg, 0.47 mmol, 94% yield). $^1$H NMR (300 MHz, CDCl$_3$): δ 7.74 (s, 1H), 7.57 (d, J=7.9 Hz, 1H), 7.38 (d, J=7.7 Hz, 1H), 7.02 (t, J=7.8 Hz, 1H), 4.95 (s, 2H), 1.49 (s, 9H), 1.45 (s, 18H), 1.41 (s, 9H) ppm. $^{13}$C NMR (75 MHz, CDCl$_3$): δ 157.4, 151.2, 147.4, 144.5, 140.0, 136.9, 136.4, 130.1, 127.4, 94.1, 84.2, 83.9, 82.2, 49.5, 28.1, 28.0, 27.9 ppm. HRMS (m/z): [M+Na]$^+$ calc, for C$_{28}$H$_{42}$IN$_3$NaO$_8$ 698.1914, found 689.1917.

Step 3. [$^{18}$F]Meta-Fluorobenzylguanidine Precursor

A solution of the product from Step 2 (173 mg, 0.26 mmol) in acetone and acetic acid (4:1, 2.2 mL) was cooled to 0° C. and treated with a solution of DMDO in acetone. The reaction mixture was stirred at 0° C. for 1 h, then warmed to room temperature and stirred for an additional 3 h. The reaction mixture was then concentrated, diluted with ethanol (1.2 mL), treated with (1r,3r,5r,7r)-spiro[adamantane-2,2'-[1,3]dioxane]-4',6'-dione (71 mg) in 10% aqueous sodium carbonate (0.9 mL) and the pH was adjusted to ~10 using 10% aqueous sodium carbonate. The reaction was then stirred for 2-4 h, and then diluted with water and extracted three times with dichoromethane. The pooled organics were dried using sodium sulfate, filtered concentrated and purified by flash chromatography (SiO$_2$, 50-100% EA/Hex) to yield the [$^{18}$F]meta-fluorobenzylguanidine precursor as a colourless solid (106 mg, 45% yield). $^1$H NMR (300 MHz, CDCl$_3$): δ 7.89 (s, 1H), 7.74 (d, J=8.2 Hz, 1H), 7.66 (d, J=7.9 Hz, 1H), 7.35 (t, J=7.9 Hz, 1H), 5.02 (s, 2H), 2.43 (br s, 2H), 2.19 (br s, 2H), 2.15 (br s, 2H), 1.85 (br s, 2H), 1.72 (br s, 4H), 1.68 (br s, 2H), 1.49 (s, 9H), 1.46 (s, 18H), 1.42 (s, 9H) ppm. $^{13}$C NMR (75 MHz, CDCl$_3$): δ 163.4, 157.3, 151.1, 147.4, 144.6, 142.2, 132.6, 131.9, 131.5, 114.0, 107.7, 84.9, 84.2, 84.0, 82.5, 55.6, 49.7, 37.3, 35.8, 33.9, 33.6, 28.1, 28.0, 26.7 ppm. HRMS (m/z): [M+Na]$^+$ calc, for C$_{41}$H$_{56}$IN$_3$NaO$_{12}$ 932.2806, found 932.2807.

Example 36. Stability of Iodonium(II) Ylides Under Radiolabeling Conditions in Absence of $^{18}$F The stability of iodonium(III) ylides were evaluated by reaction monitoring with $^1$H NMR under conditions designed to closely mimic those of radiofluorination, in the absence of $^{18}$F. Specifically, 3.5 μmol of iodonium(III) ylide (1.4-1.9 mg) was added to 700 μL of a stock solution of N,N,N',N'-tetraethylammonium bicarbonate (4.8 mg·mL$^{-1}$, 25 mM) in DMF-d$_7$ to produce a 5 mM solution in an NMR tube. No fluoride source was added to the reaction mixture. A baseline $^1$H NMR spectrum (300 MHz, 8 scans) was acquired. The NMR tubes were heated to 120° C. for 1 min, rapidly cooled to room temperature, and a $^1$H NMR spectrum acquired (t=1 min). This process was repeated to acquire $^1$H NMR spectra for 2, 3, 5, and 10 minute time points. Each spectrum underwent Fourier transform, phase correction, and was referenced to the solvent residual formyl proton signal at 8.01 ppm. Integral regions were applied as follows: 5.36-5.42 (parent compound), 5.24-5.27 and 5.09-5.17 (products) ppm. The parent fraction of the total of all regions was corrected for baseline and used to evaluate precursor stability. Experiments were conducted with each of the substrates in parallel, and repeated with freshly prepared stock solution. In the absence of heating, no measurable decomposition was observed in solution over 1 h. In the absence of base, dioxodione-based ylides (e.g., SPIAd, Meldrum's) did not show appreciable levels of decomposition, as evaluated by $^1$H NMR, over 1 h at 120° C. Analytical HPLC (stationary phase: Eclipse Plus C18, 3.5 μm, 4.6×100 mm; mobile phase: 50% CH$_3$CN/0.1% NH$_4$OH$_{(aq)}$, 1 min, linear gradient to 90% CH$_3$CN, 8 min, 90% CH$_3$CN, 3 min, 1 mL·min$^{-1}$) was conducted on the terminal samples (i.e., after the 10 min time point was acquired). Independently prepared samples of various benzyloxyphenyl species were then evaluated by $^1$H NMR and analytical HPLC to determine their presence in the decomposition of iodonium ylides.

Example 37. General Procedure for Radioisotope Production and Preparation

A GE PETtrace 16.5 MeV cyclotron was used for [$^{18}$F] fluoride production by the $^{18}$O(p,n)$^{18}$F nuclear reaction to irradiate $^{18}$O-enriched water. [$^{18}$F]fluoride was delivered to a lead-shielded hot cell in $^{18}$O-enriched water by nitrogen gas pressure. [$^{18}$F]Fluoride was prepared for radiofluorination of aromatics by one of two methods:

Method (A)

A solution of base (e.g., tetraethylammonium bicarbonate, 7 mg) in acetonitrile and water (1 mL, 7:3) was added to an aliquot of target water (≤1 mL) containing the appropriate amount of [$^{18}$F]fluoride in a V-shaped vial sealed with a teflon-lined septum. The vial was heated to 110° C. while nitrogen gas was passed through a P$_2$O$_5$-Drierite™ column followed by the vented vial. When no liquid was visible in the vial, it was removed from heat, anhydrous acetonitrile (1 mL) was added, and the heating was resumed until dryness. This step was repeated an additional three times. The vial was then cooled at room temperature under nitrogen pressure. The contents were resolubilized in the desired solvent (e.g. DMF).

Method (B)

An aliquot of target water containing the appropriate amount of [$^{18}$F]fluoride was slowly passed through an anion exchange cartridge (MPI, ORTG, Tennessee, USA), preactivated by flushing with NaHCO$_3$(aq (8%, 1 mL) and water (2-3 mL, until neutral by pH indicator). [$^{18}$F]Fluoride was eluted using a solution of base (e.g., tetraethylammonium bicarbonate, 7 mg) in acetonitrile and water (1 mL, 7:3) into a V-shaped vial sealed with a teflon-lined septum. Drying and resolublization were then performed as described above. For preparations involving crypt-222, drying was conducted at 95° C.

Example 38. General Procedure for Radiofluorination of Arenes

Azeotropically dried [$^{18}$F]Et$_4$NF (typically 50-500 µCi, 2-20 MBq), resolubilized in DMF (400 µL), was added to a V-vial containing iodonium(III) ylide precursor (2 mg). The reaction was heated at 120° C. for 10 min, and quenched with HPLC buffer (e.g., 60:40 CH$_3$CN:H$_2$O+0.1 N ammonium formate, 1 mL). Fluorine incorporation and product identities were determined by radioTLC and radioHPLC (n≥3).

Example 39. General Procedure for Analysis of Radiofluorination Reactions

Radioactivity was quantified using a Capintec Radioisotope Calibrator (CRC-712M) ion chamber. Radiochemical incorporation yields were determined by radioTLC. EMD TLC Silica gel 60 plates (10×2 cm) were spotted with an aliquot (1-5 µL) of crude reaction mixture approximately 1.5 cm from the bottom of the plate (baseline). Unless otherwise noted, TLC plates were developed in a chamber containing ethyl acetate until within 2 cm of the top of the plate (front). Analysis was performed using a Bioscan AR-2000 radio-TLC imaging scanner and WinScan software. Radiochemical identity and purity were determined by radioHPLC with a Waters 1515 Isocratic HPLC Pump equipped with a Waters 2487 Dual λ Absorbance Detector, a Bioscan Flow-Count equipped with a NaI crystal, and Breeze software or a Shimadzu LC-10AD binary variable pump equipped with an SPD-10AD single wavelength UV detector, a Carroll-Ramsey 105S-1 single-channel high sensitivity radiation detector, and Clarity software.

To account for immobilized radioactivity (which would not be accounted for by radioTLC), reaction vessels were decanted after quenching and residual and solution radioactivity were separately quantified. In all cases, ≥95% of radioactivity remained in solution.

Example 40. General Procedures for Measurement of Time-Course of Radiofluorination To evaluate the extent of radiofluorination over time, reactions were constructed under the specified conditions and based on the procedure described above. Upon addition of resolubilized [$^{18}$F]fluoride salts to the vial containing precursor, an aliquot (1-10 µL) was removed and quenched in a test tube containing water or aqueous buffer (50-100 µL). This sample represented t$_0$. The vials were then heated to the prescribed temperature in heating blocks and additional samples withdrawn at predetermined times and immediately quenched in the same way. For reactions conducted at ambient temperature, samples were withdrawn at predetermined times after addition of [$^{18}$F]fluoride. Quenched samples were analyzed by rTLC and rHPLC, if suitable. In cases where time-courses were used for direct comparison of precursors or radiofluorination conditions, a common batch of dried and resolubilized [$^{18}$F]fluoride was used simultaneously for each condition. All time-course experiments were conducted in triplicate.

Examples 41-44. Radiofluorination of Naphthalene Scaffolds

Examples 41-44 were prepared according to the general fluorination procedures provided herein; Radiochemical conversion of Examples 41-44 is shown below in Table 1.

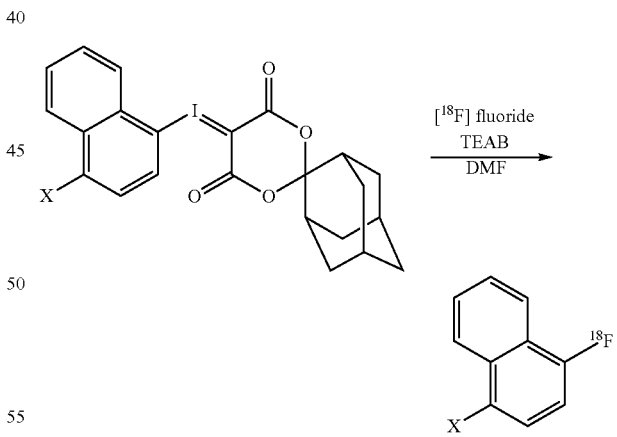

TABLE 1

| Example No. | X | Radiochemical Conversion (RCC) |
|---|---|---|
| 41 | OMe | 49 ± 5% (5 min) |
| 42 | H | 30 ± 5% (2 min) |
| 43 | CN | 59 ± 14% (20 min) |
| 44 | NO$_2$ | 11 ± 5% (20 min) |

Examples 45-47. Radiofluoination of Quinoline Scaffolds

Examples 45-47 were prepared according to the general fluorination procedures provided herein. Radiochemical conversion of Examples 45-47 is shown below in Table 2.

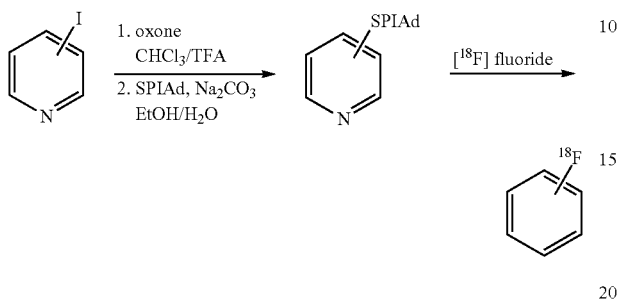

TABLE 2

| Example No. | Structure | Radiochemical Conversion (RCC) |
|---|---|---|
| 45 | [18F]-quinoline (6-position) | 73 ± 17% |
| 46 | [18F]-quinoline (3-position) | 62 ± 6% |
| 47 | [18F]-isoquinoline (4-position) | 80 ± 7% |

Examples 48-50. Radiofluorination of Indole Scaffolds

Examples 48-50 were prepared according to the general fluorination procedures provided herein; Radiochemical conversion of Examples 48-50 is shown below in Table 3.

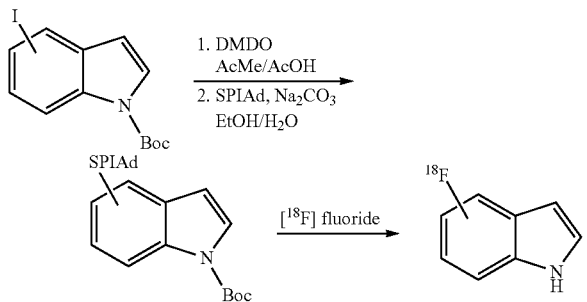

TABLE 3

| Example No. | Structure | Radiochemical Conversion (RCC) |
|---|---|---|
| 48 | 6-[18F]-indole | 23 ± 5% |
| 49 | 5-[18F]-indole | 8 ± 4% |
| 50 | 4-[18F]-indole | 36 ± 8% |

Example 51. Radiofluorination and Characterization of Labeled Drug Fragments $^{18}$F-radiolabeled drug fragments were prepared using the drug precursors described in Example 31 according to the following procedures:

A. Filorexant

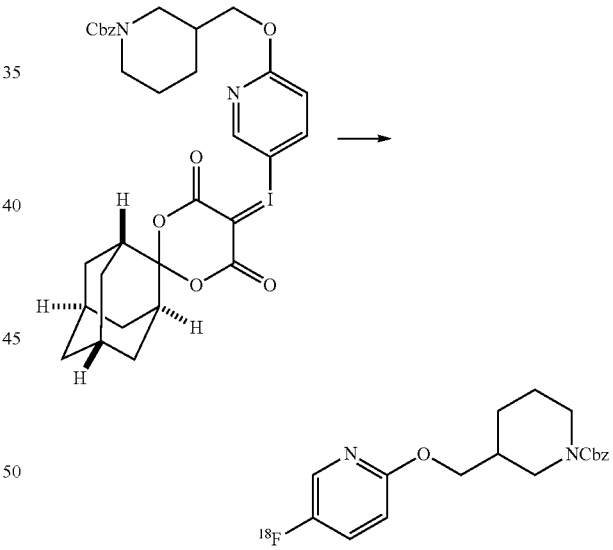

TEAB (3 mg) was used to dry [$^{18}$F]fluoride. A solution of precursor (6 mg) in DMF (0.4 mL) was added in the vial. The mixture was heated at 150° C. for 10 min, and then quenched with HPLC mobile phase (75% CH$_3$CN, 25% 0.1 M NH$_4$·HCO$_2$(aq), 0.2 mL). TLC plate was spotted with crude mixture (2 μL) and developed with 100% EtOAc to determine the radiochemical conversion (RCC). Then the solution was diluted with water (15 mL), passed through C18 cartridge, washed with water (24 mL), and eluted with acetonitrile (1.5 mL) into a new vial. The mixture (20 μL) was injected into the radio-HPLC to determine the identity via coinjection with the [$^{19}$F]-filorexant standard. Radiochemical conversion: 45±4%.

B. Mosapride

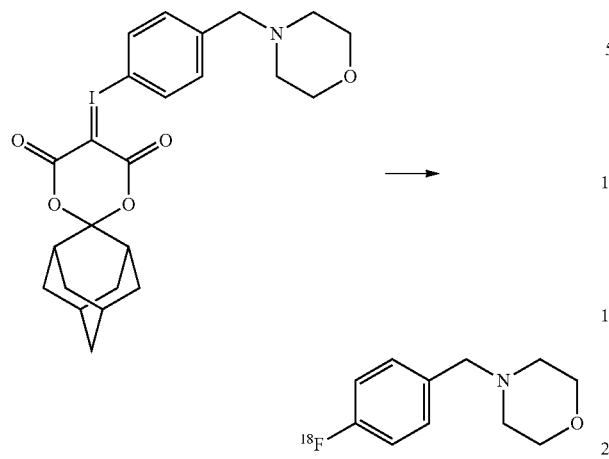

TEAB (2 mg) was used to dry [$^{18}$F]fluoride. A solution of precursor (2 mg) in DMF (0.4 mL) was added to the vial and the mixture heated to 120° C. for 10 min, then quenched with water. A silica gel TLC plate was spotted with the crude mixture and developed with 100% EtOAc to determine radiochemical conversion (RCC). The identity of the product was confirmed by coinjection with the nonradioactive standard [$^{19}$]-mosapride standard by HPLC and in-line UV and radiation detectors. Radiochemical conversion: 35±6%.

C. Lapatinib

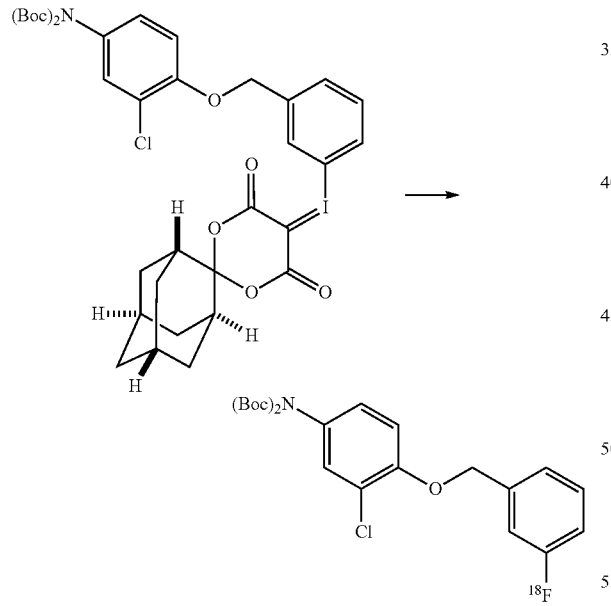

TEAB (3 mg) was used to dry [$^{18}$F]fluoride. A solution of precursor (4 mg) in DMF (0.4 mL) was added in the vial. The mixture was heated at 95° C. for 11 min, and then quenched with HPLC mobile phase (75% CH$_3$CN, 25% 0.1 M NH$_4$.HCO$_2$(aq), 0.2 mL). TLC plate was spotted with crude mixture (2 μL) and developed with 100% EtOAc to determine the radiochemical conversion (RCC). The mixture (20 μL) was injected into the radio-HPLC to determine the identity via coinjection with [$^{19}$F]-lapatinib standard. Radiochemical conversion: 66±8%.

D. Risperidone

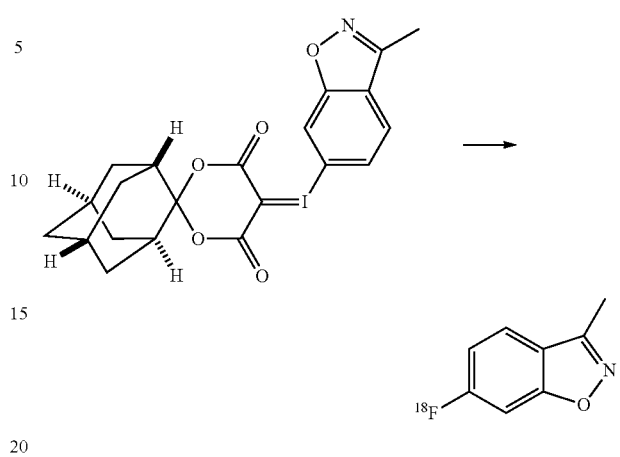

TEAB (2 mg) was used to dry [$^{18}$F]fluoride. A solution of precursor (2.5 mg) in DMF (0.4 mL) was added in the vial. The mixture was heated at 120° C. for 15 min, and then quenched with HPLC mobile phase (60%0/CH$_3$CN, 40% 0.1 M NH$_4$.HCO$_2$(aq), 0.2 mL). TLC plate was spotted with crude mixture (2 μL) and developed with 100% EtOAc to determine the radiochemical conversion (RCC). The mixture (20 μL) was injected into the radio-HPLC to determine the identity via coinjection with [$^{19}$F]-risperidone standard. Radiochemical conversion: 25±4%.

E. Ezetimibe

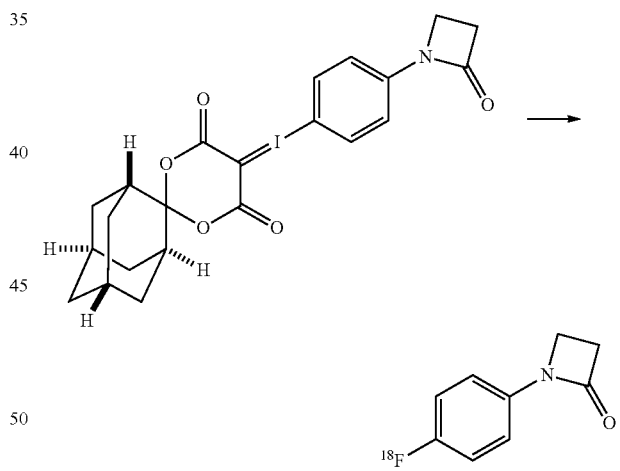

TEAB (3 mg) was used to dry [$^{18}$F]fluoride. A solution of precursor (5 mg) in DMF (0.4 mL) was added in the vial. The mixture was heated at 130° C. for 12 min, and then quenched with HPLC mobile phase (40% CH$_3$CN, 60% 0.1 M NH$_4$.HCO$_2$(aq), 0.2 mL). TLC plate was spotted with crude mixture (2 μL) and developed with 100% EtOAc to determine the radiochemical conversion (RCC). Then the solution was diluted with water (15 mL), passed through C18 cartridge, washed with water (24 mL), and eluted with acetonitrile (1.5 mL) into a new vial. The mixture (20 μL) was injected into the radio-HPLC to determine the identity via coinjection with [$^{19}$F]-ezetimibe standard. Radiochemical conversion: 71±13%.

F. Astemizole

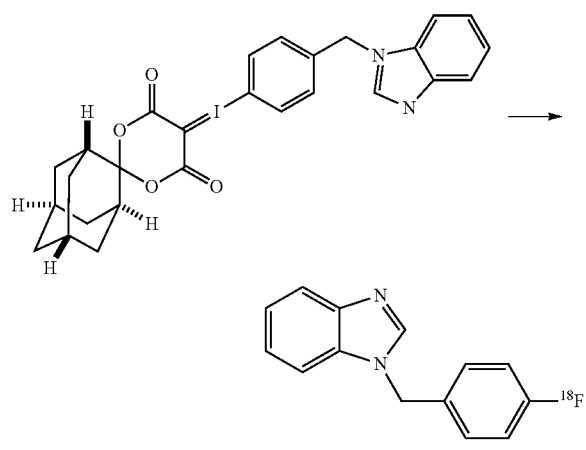

TEAB (3 mg) was used to dry [$^{18}$F]fluoride. A solution of precursor (6 mg) in DMF (0.4 mL) was added in the vial. The mixture was heated at 140° C. for 11 min, and then quenched with HPLC mobile phase (50% CH$_3$CN, 50% 0.1 M NH$_4$.HCO$_2$(aq), 0.2 mL). TLC plate was spotted with crude mixture (2 μL) and developed with 100% EtOAc to determine the radiochemical conversion (RCC). Then the solution was diluted with water (15 mL), passed through C18 cartridge, washed with water (30 mL), and eluted with acetonitrile (1.5 mL) into a new vial. The mixture (20 μL) was injected into the radio-HPLC to determine the identity via coinjection with [$^{19}$F]-astemizole standard. Radiochemical conversion: 51 f 7%.

G. Paroxetine

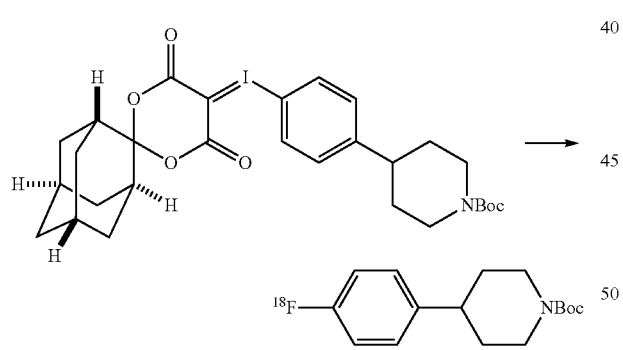

TEAB (3 mg) was used to dry [$^{18}$F]fluoride. A solution of precursor (5.4 mg) in DMF (0.4 mL) was added in the vial. The mixture was heated at 110° C. for 12 min, and then quenched with HPLC mobile phase (70% CH$_3$CN, 30% 0.1 M NH$_4$.HCO$_2$(aq), 0.2 mL). TLC plate was spotted with crude mixture (2 μL) and developed with 100% EtOAc to determine the radiochemical conversion (RCC). Then the solution was diluted with water (15 mL), passed through C$_{18}$ cartridge, washed with water (30 mL), and eluted with acetonitrile (1.5 mL) into a new vial. The mixture (20 μL) was injected into the radio-HPLC to determine the identity via coinjection with [$^{19}$F]-paroxetine standard. Radiochemical conversion: 41±4%.

H. Pitavastatin

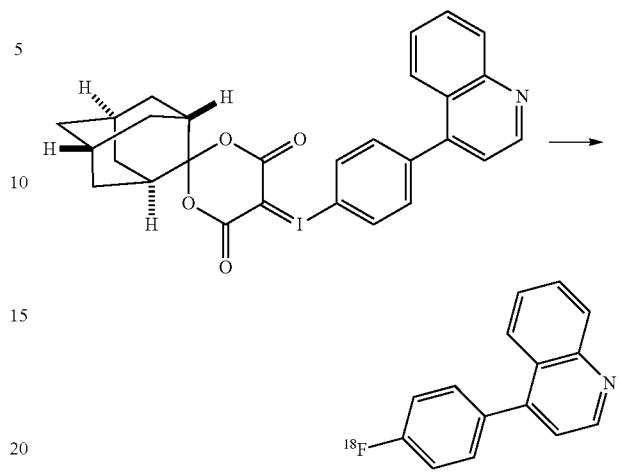

TEAB (2.5 mg) was used to dry [$^{18}$F]fluoride. A solution of precursor (5.2 mg) in DMF (0.4 mL) was added in the vial. The mixture was heated at 110° C. for 12 min, and then quenched with HPLC mobile phase (70% CH$_3$CN, 30% 0.1 M NH$_4$.HCO$_2$(aq), 0.2 mL). TLC plate was spotted with crude mixture (2 μL) and developed with 100% EtOAc to determine the radiochemical conversion (RCC). Then the solution was diluted with water (15 mL), passed through C$_{18}$ cartridge, washed with water (10 mL), and eluted with acetonitrile (1.5 mL) into a new vial. The mixture (20 μL) was injected into the radio-HPLC to determine the identity via coinjection with [$^{19}$F]-pitavastatin standard. Radiochemical conversion: 57±9%.

I. Crizotinib

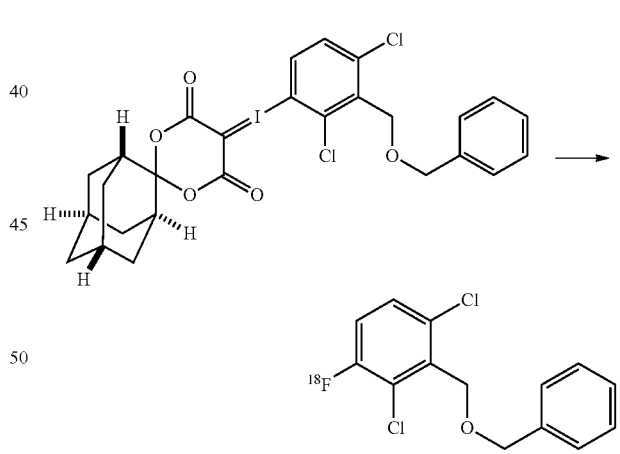

TEAB (2.0 mg) was used to dry [$^{18}$F]fluoride. A solution of precursor (1.4 mg) in DMF (0.4 mL) was added in the vial. The mixture was heated at 100° C. for 12 min, and then quenched with HPLC mobile phase (80% CH$_3$CN, 20% 0.1 M NH$_4$.HCO$_2$(aq), 0.2 mL). TLC plate was spotted with crude mixture (2 μL) and developed with 100% EtOAc to determine the radiochemical conversion (RCC). Then the solution was diluted with water (15 mL), passed through C$_{18}$ cartridge, washed with water (20 mL), and eluted with acetonitrile (1.5 mL) into a new vial. The mixture (20 μL) was injected into the radio-HPLC to determine the identity via coinjection with [$^{19}$F]-crizotinib standard. Radiochemical conversion: 82±6%.

Example 52. Preparation of [$^{18}$F]Safinamide

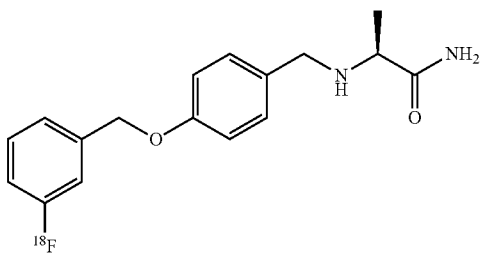 [SMILES: C[C@H](NCc1ccc(OCc2cccc([18F])c2)cc1)C(N)=O]

[$^{18}$F]Fluoride was dried by iterative azeotropic evaporation of anhydrous acetonitrile in the presence of N,N,N,N-tetraethylammonium bicarbonate (TEAB). The residue was diluted with anhydrous N,N-dimethylformamide to produce a 10 mg·mL$^{-1}$ solution of TEAB. A 400 µL aliquot of this solution was added to V-vial containing 2 mg of [$^{18}$F]-safinamide precursor. The mixture was heated to 120° C. for 10 min, and then cooled to room temperature. An aliquot of 12 N HCl (0.2 mL) was added to the vial, which was then heated to 90° C. for 3 minutes. A sample of the crude reaction mixture was withdrawn and neutralized with aqueous sodium bicarbonate. The sample was analyzed by radioTLC (SiO$_2$, developed with EtOAc) to determine the radiochemical conversion (RCC), and radioHPLC coinjection with the nonradioactive standard to confirm identity. Radiochemical conversion: 15%.

Example 53. Preparation of 6-[$^{18}$F]fluoro-meta-tyrosine ([$^{18}$F]FMT)

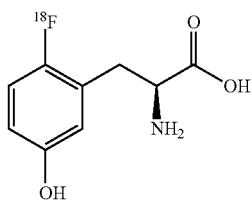 [SMILES: N[C@@H](Cc1cc(O)ccc1[18F])C(=O)O]

An aliquot (0.1-0.5 mL) of cyclotron target water containing [$^{18}$F]fluoride (0.5-1.5 mCi, measured in a dose calibrator, to) was added to a V-vial containing N,N,N,N-tetraethylammonium bicarbonate (TEAB, 2.0 mg). Acetonitrile (1 mL) was added and the mixture heated to 110° C. with nitrogen gas flowing through the vial until no bulk liquid was visible. This drying step was then repeated three more times using anhydrous acetonitrile. The vial was cooled for 2 minutes in a room temperature water bath, before addition of a solution of [$^{18}$F]FMT-precursor (4.0 mg) in anhydrous DMF (0.2 mL). The vial was then sealed and heated to 120° C. for 20 minutes, after which it was again cooled in a room temperature water bath. A sample of the reaction mixture (1-2 µL) was withdrawn and spotted on a silica-coated TLC plate that was then developed using ethyl acetate to quantify radioactive incorporation. A solution of 6 N HCl (0.2 mL) was added to the reaction vial, which was then heated to 100° C. for 3 minutes, followed by cooling to room temperature. Again, a sample of the reaction mixture was withdrawn and radioTLC conducted as described above to determine the extent of deprotection. The reaction mixture was partially neutralized with 5 N NaOH (0.2 mL), and diluted with HPLC mobile phase (5% MeOH, 0.1% HCO$_2$H, 1.0 mL). The contents of the reactor were then loaded into an injector loop and purified by semi-preparative HPLC (stationary phase: Luna C18, 250×10 mm, 100 Å, 5 µm: mobile phase as described above, 5 mL·min$^{-1}$: t$_R$=~8 min). Fractions containing product were collected and radioactivity measured in a dose calibrator to determine isolated yield (EOS). The total time from t$_0$ to EOS was 60±1 min. Radiochemical yield: 12%.

Example 54. Preparation of [$^{18}$F]Meta-Fluorobenzylguanidine ([$^{18}$F]mFBC)

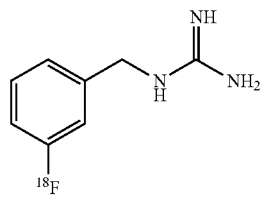 [SMILES: N=C(N)NCc1cccc([18F])c1]

An aliquot (0.1-0.5 mL) of cyclotron target water containing [$^{18}$F]fluoride (0.5-1.5 mCi, measured in a dose calibrator, t$_0$) was added to a V-vial containing N,N,N,N-tetraethylammonium bicarbonate (TEAB, 4.0 mg). Acetonitrile (1 mL) was added and the mixture heated to 110° C. with nitrogen gas flowing through the vial until no bulk liquid was visible. This drying step was then repeated three more times using anhydrous acetonitrile. The vial was cooled for 2 minutes in a room temperature water bath, before addition of a solution of [$^{18}$F]mFBG precursor (4.0 mg) in anhydrous DMF (0.2 mL). The vial was then sealed and heated to 120° C. for 20 minutes, after which it was again cooled in a room temperature water bath. A sample of the reaction mixture (1-2 µL) was withdrawn and spotted on a silica-coated TLC plate that was then developed using ethyl acetate to quantify radioactive incorporation. A solution of 6 N HCl (0.2 mL) was added to the reaction vial, which was then heated to 100° C. for 10 minutes, followed by cooling to room temperature. Again, a sample of the reaction mixture was withdrawn and radioTLC conducted as described above to determine the extent of deprotection. The reaction mixture was partially neutralized with 5 N NaOH (0.2 mL), and diluted with HPLC mobile phase (10% EtOH, 28 mM HCl, 20 mM NH$_4$OAc, pH 2, 0.5 mL). The contents of the reactor were then loaded into an injector loop and purified by semi-preparative HPLC (stationary phase: Hamilton PRP-1, 250×10 mm, 10 µm; mobile phase as described above, 3.5 mL·min$^{-1}$; t$_R$=~17 min). Fractions containing product were collected and radioactivity measured in a dose calibrator to determine isolated yield (EOS). The total time from t$_0$ to EOS was 75±2 min. Radiochemical yield: 14%.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A process for fluorodeiodination of an aromatic iodide compound comprising:
   (a) oxidizing an aromatic iodide compound (Ar—I) to form an iodonium compound;
   (b) reacting the iodonium compound with a compound of formula (A):

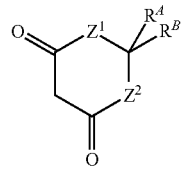

A to form an iodonium ylide; and
   (c) reacting the iodonium ylide with a fluoride source to form an aromatic fluoride compound (Ar—F);
wherein:
   $Z^1$ is selected from the group consisting of $NR^{Z1}$, O, and S;
   $Z^2$ is selected from the group consisting of $NR^{Z2}$, O, and S;
   $R^{Z1}$ is selected from the group consisting of H, $C_{1-6}$ alkyl, $C_{3-10}$ cycloalkyl, $C_{6-10}$ aryl, 4-10 membered heterocycloalkyl, and 5-10 membered heteroaryl, wherein said $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;
   $R^{Z2}$ is selected from the group consisting of H, $C_{1-6}$ alkyl, $C_{3-10}$ cycloalkyl, $C_{6-10}$ aryl, 4-10 membered heterocycloalkyl, and 5-10 membered heteroaryl, wherein said $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;
   $R^A$ and $R^B$ in combination, together with the carbon atom to which $R^A$ and $R^B$ are attached, form an 8, 9, or 10-membered carbocyclic or heterocyclic ring containing 8 to 10 carbon atoms and 0, 1, or 2 ring heteroatoms, each independently selected from N, O, and S, wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo; and
   each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino.

2. The process of claim 1, wherein step (a) is performed in the presence of an oxidizing agent selected from the group consisting of sodium perborate, urea-hydrogen peroxide adduct, 1-chloromethyl-4-fluoro-1,4-diazoniabicyclo[2.2.2]octane bis(tetrafluoroborate), potassium peroxymonosulfate, dimethyldioxirane, or meta-chloroperoxybenzoic acid, and a carboxylate salt that is an acetate source or a trifluoroacetate source.

3. The process of claim 1, wherein step (b) is carried out in the presence of a carbonate base.

4. The process of claim 1, wherein said iodonium ylide formed in step (b) is an iodonium ylide of Formula D:

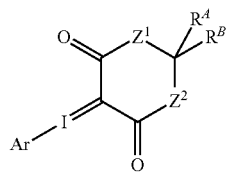

D wherein $Z^1$ is O and $Z^2$ is O.

5. The process of claim 1, wherein the compound of Formula A is selected from compounds of the following formulae:

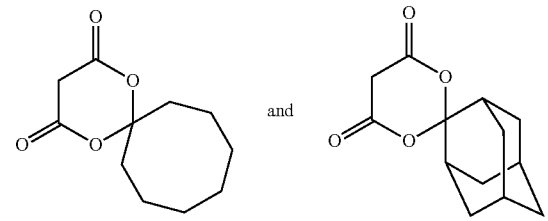

6. The process of claim 1, wherein the compound of Formula A is a compound of the following formula:

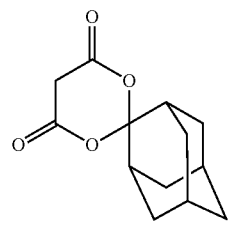

7. The process of claim 1, wherein the compound of Formula D is selected from compounds of the following formulae:

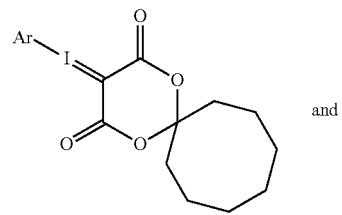

and

-continued

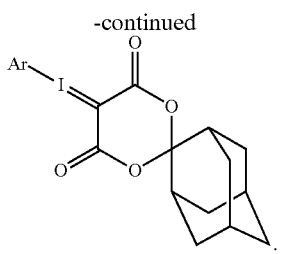

8. The process of claim 1, wherein said fluoride source comprises [$^{18}$F] fluoride.

9. The process of claim 1, wherein step (a) is performed in the presence of an oxidizing agent selected from the group consisting of sodium perborate, urea-hydrogen peroxide adduct, 1-chloromethyl-4-fluoro-1,4-diazoniabicyclo[2.2.2] octane bis(tetrafluoroborate), potassium peroxymonosulfate, dimethyldioxirane, or meta-chloroperoxybenzoic acid, and a carboxylate salt that is an acetate source or a trifluoroacetate source, and step (b) is carried out in the presence of a carbonate base.

10. The process of claim 9, wherein the compound of Formula A is a compound of the following formula:

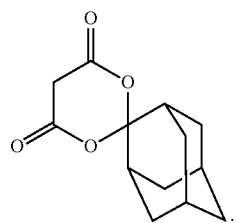 [SMILES: O=C1CC(=O)OC2(O1)C1CC3CC(C1)CC2C3]

11. The process of claim 10, wherein said fluoride source comprises [$^{18}$F] fluoride.

12. A compound of Formula D:

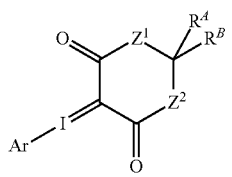

D wherein:
Ar is an aromatic group;
$Z^1$ is selected from the group consisting of $NR^{Z1}$, O, and S;
$Z^2$ is selected from the group consisting of $NR^{Z2}$, O, and S;
$R^{Z1}$ is selected from the group consisting of H, $C_{1-6}$ alkyl, $C_{3-10}$ cycloalkyl, $C_{6-10}$ aryl, 4-10 membered heterocycloalkyl, and 5-10 membered heteroaryl, wherein said $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;
$R^{Z2}$ is selected from the group consisting of H, $C_{1-6}$ alkyl, $C_{3-10}$ cycloalkyl, $C_{6-10}$ aryl, 4-10 membered heterocloalkyl, and 5-10 membered heteroaryl, wherein said $C_{1-6}$ alkyl, $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^{20}$ groups;

$R^A$ and $R^B$ in combination, together with the carbon atom to which $R^A$ and $R^B$ are attached, form an 8, 9, or 10-membered carbocyclic or heterocyclic ring containing 8 to 10 carbon atoms and 0, 1, or 2 ring heteroatoms, each independently selected from N, O, and S, wherein the ring formed by the combination of $R^A$ and $R^B$ is unsubstituted or substituted by 1, 2, or 3 substituents independently selected from halogen, $C_{1-6}$ alkyl, $C_{2-6}$ alkenyl, $C_{2-6}$ alkynyl, $C_{1-6}$ haloalkyl, $C_{1-6}$ hydroxyalkyl, and oxo;

and each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino; and wherein Ar is connected to the iodonium group through an aromatic ring carbon atom.

13. The compound of claim 12, wherein $Z^1$ is O and $Z^2$ is O.

14. The compound of claim 12, wherein the compound of Formula D is selected from compounds of the following formulae:

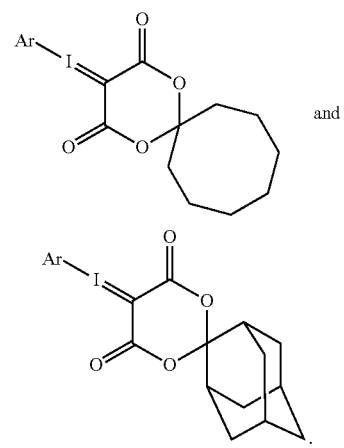

and

15. The compound of claim 12, wherein the compound of Formula D is a compound of the following formula:

105
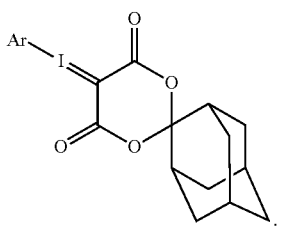
16. The compound of claim 12, selected from compounds of the following formulae:
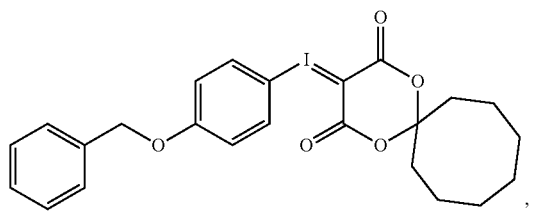
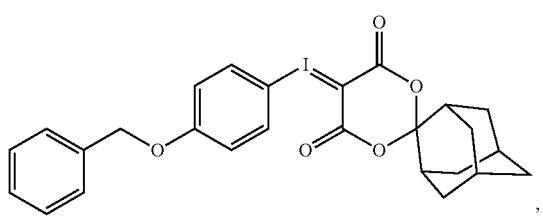
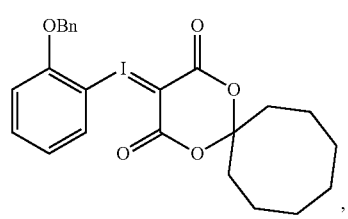
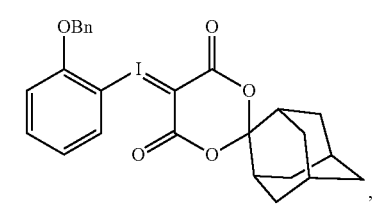
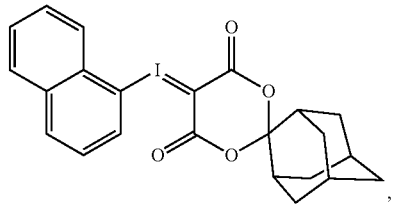
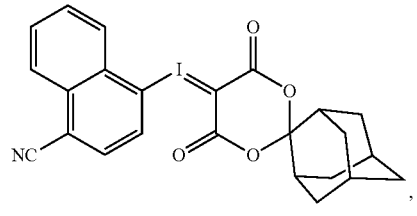
106
-continued
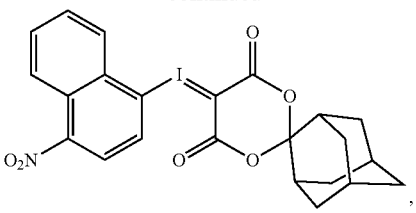
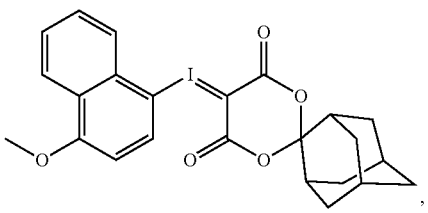
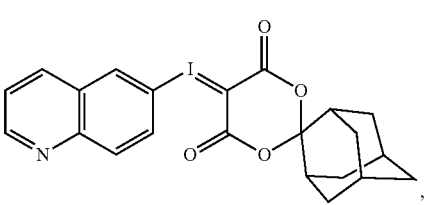
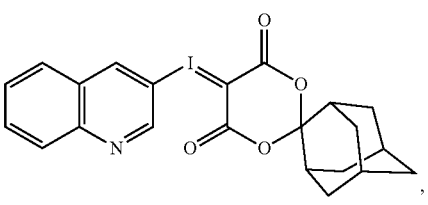
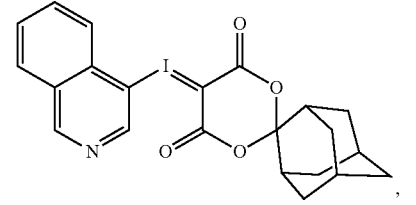
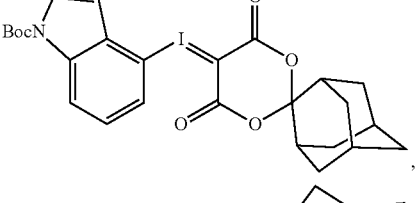
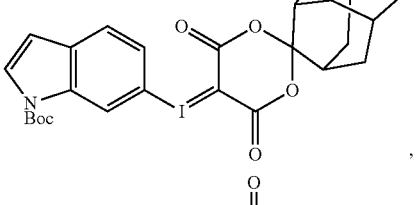
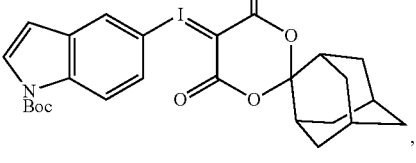

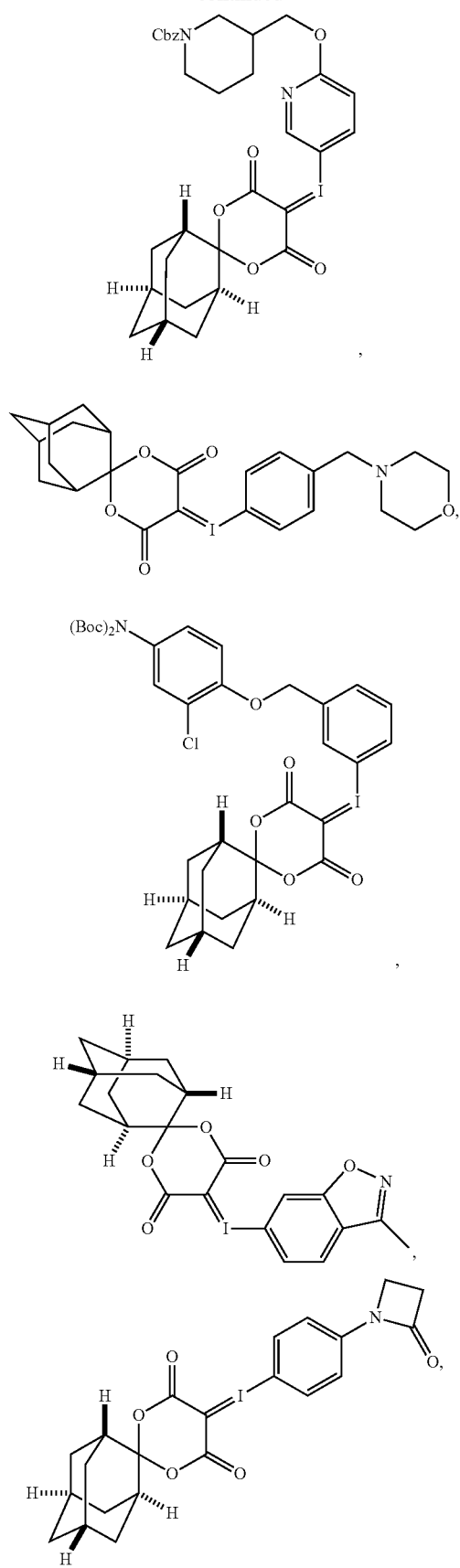

-continued

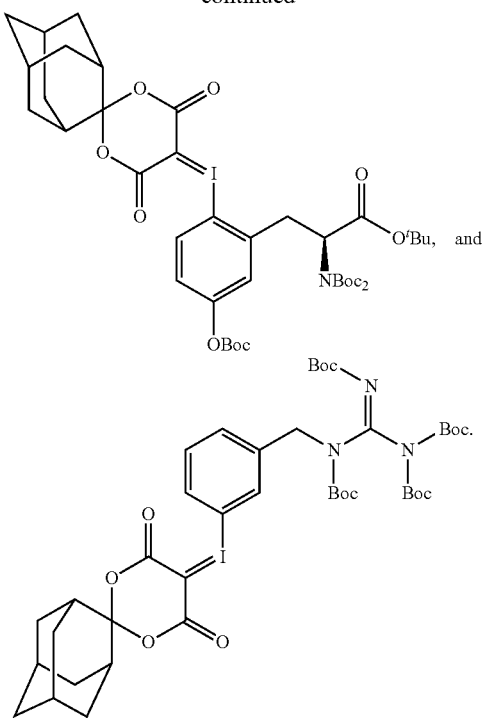

17. A process for preparing a compound according to claim 12, comprising:
    (a) oxidizing an aromatic iodide compound (Ar—I), to form an iodonium compound; and
    (b) reacting the iodonium compound with a compound of formula (A):

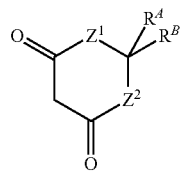

A wherein $Z^1$, $Z^2$, $R^A$ and $R^B$ are as defined in claim 12, to form the compound according to claim 12.

18. A process for preparing an aromatic fluoride compound (Ar—F) comprising:
    reacting a compound according to claim 12 with a fluoride source to form an aromatic fluoride compound (Ar—F).

19. The process of claim 18, wherein said fluoride source comprises [$^{18}$F] fluoride.

20. An [$^{18}$F] radiolabelled compound, wherein the compound is selected from filorexant, mosapride, risperidone, ezetimibe, astemizole, crizotinib, and safinamide.

* * * * *